(12) United States Patent
Suffin et al.

(10) Patent No.: US 7,489,964 B2
(45) Date of Patent: Feb. 10, 2009

(54) ELECTROENCEPHALOGRAPHY BASED SYSTEMS AND METHODS FOR SELECTING THERAPIES AND PREDICTING OUTCOMES

(75) Inventors: Stephen C. Suffin, Sherman Oaks, CA (US); W. Hamlin Emory, Malibu, CA (US); Leonard J. Brandt, Laguna Hills, CA (US)

(73) Assignee: CNS Response, Inc., Costa Mesa, CA (US)

( * ) Notice: Subject to any disclaimer, the term of this patent is extended or adjusted under 35 U.S.C. 154(b) by 5 days.

(21) Appl. No.: 11/605,585

(22) Filed: Nov. 29, 2006

(65) Prior Publication Data

US 2008/0125669 A1    May 29, 2008

Related U.S. Application Data

(62) Division of application No. 10/193,735, filed on Jul. 11, 2002, now Pat. No. 7,177,675.

(60) Provisional application No. 60/304,628, filed on Jul. 11, 2001.

(51) Int. Cl.
*A61B 5/04* (2006.01)
*A61K 49/00* (2006.01)

(52) U.S. Cl. .................. 600/544; 600/545; 424/9.2

(58) Field of Classification Search .......... 600/544, 600/545; 424/9.2
See application file for complete search history.

(56) References Cited

U.S. PATENT DOCUMENTS

| 6,223,074 B1 * | 4/2001 | Granger ........... 600/544 |
| 6,622,036 B1 * | 9/2003 | Suffin ............ 600/544 |
| 2003/0135128 A1 * | 7/2003 | Suffin et al. ...... 600/544 |

* cited by examiner

*Primary Examiner*—Patricia C Mallari
(74) *Attorney, Agent, or Firm*—Medlen & Carroll, LLP

(57) ABSTRACT

A method and system for utilizing neurophysiologic information obtained by techniques such as quantitative electroencephalography (QEEG), electrode recordings, MRI in appropriately matching patients with therapeutic entities is disclosed. The present invention enables utilization of neurophysiologic information, notwithstanding its weak correlation with extant diagnostic schemes for mental disorders, for safer and expeditious treatment for mental disorders, discovering new applications for therapeutic entities, improved testing of candidate therapeutic entities, inferring the presence or absence of a desirable response to a treatment, and deducing the mode of action of one or more therapeutic entities. In particular, methods for effectively comparing neurophysiologic information relative to a reference set are disclosed along with database-based tools for deducing therapeutic entity actions on particular patients such that these tools are readily accessible to remote users.

13 Claims, 15 Drawing Sheets

ELECTROENCEPHALOGRAPHY BASED SYSTEMS AND METHODS FOR SELECTING THERAPIES AND PREDICTING OUTCOMES

CROSS-REFERENCE TO RELATED APPLICATIONS

This application is a divisional of U.S. patent application Ser. No. 10/193,735 filed on Jul. 11, 2002, now U.S. Pat. No. 7,177,675, and which has priority to U.S. Provisional Application No. 60/304,628 filed on Jul. 11, 2001.

FIELD OF THE INVENTION

The present invention relates to the field of electroencephalography (EEG), and more specifically includes methods and systems for selecting therapies for behaviorally-diagnosed psychiatric conditions and for predicting outcomes from therapies. This invention also includes methods of treating patients with the selected therapies.

BACKGROUND OF THE INVENTION

Conventional treatment for mental disorders follows a diagnosis in accordance with a standard followed by selection of a treatment reported to be effective for that particular diagnosis. Typically there are several treatment options available. The selection of a particular treatment depends on the judgement of a physician. The soundness of this judgement, in turn, depends on the information available to the physician. The information available to the physician often includes risk of allergic responses and the like in the event a substance is administered as part of the treatment. However, little else is at hand to help the physician avoid prescribing a treatment to which the patient is non-responsive or worse, a treatment that aggravates the mental illness rather than control it. Thus, physicians attempt numerous treatment modalities in order to determine an effective treatment in a given case.

Heterogeneity of treatment response of diagnosed mental illness is well known. Accordingly, there have been attempts to improve the diagnostic methods to identify more homogeneously responsive groupings of particular mental disorders. Yet, despite the increased homogeneity of diagnosed mental illness within and across practitioners, response to treatment of mental disorders continues to be markedly heterogeneous.

Presently, the Diagnostic and Statistical Manual of Mental Disorders ("DSM") provides definitive guidelines for diagnosing and treating mental disorders. See, e.g., Nathan et al.: "Psychopathology: Description and Classification" in *Annual Reviews of Psychology,* 50:79-107 (1999). The DSM manual, presently in its fourth edition, commonly referred to as "DSM-IV," is organized along various axes. For instance, axis I disorders include major depression and schizophrenia; axis II includes personality disorders; while axis III addresses physical disorders contributing to psychological symptoms. A convenient view of the DSM entries is in accordance with its chapters since they are topically organized to avoid excessive details. Such details are within the plurality of diagnoses described in each of the chapters. Example chapters include those on 'childhood disorders,' 'eating disorders,' 'substance-related disorders,' 'anxiety,' 'mood disorders' and the like.

Another, alternative standard for diagnosing mental disorders is the set of criteria maintained by the World Health Organization ("WHO") as the International Classification of Diseases ("ICD"). ICD is employed more extensively in Europe than North America, although, DSM-UV remains the predominant international standard for allowing independent health providers to make similar diagnoses of a particular patient despite the inherently subjective nature of the underlying observations.

Applying the aforesaid standard diagnostic techniques requires data collection. At present there are available various methods of data collection, such as objective measures of brain activity or patient interviews and observations of subject's stimulated or natural behavior. For instance, objective measures such as recordings from the electrodes attached to the head of a subject, termed electroencephalograms ("EEG"), have long been available. However, they have had very limited use outside the context of monitoring and controlling seizures or studying sleep related disorders.

Notably, known systems for diagnosing mental disorders, such as DSM-UV, do not employ EEG recordings to aid in either diagnosis or treatment of a mental disorder other than in the context of seizures, brain death, intraoperative monitoring or dementia. For instance, a committee of experts in an article, Hoffman et al., J. of Neuropsychiatry and Clinical Neurosciences, 11:3 (1999), cites the American Academy of Neurology ("AAN") as recommending quantitative EEG ("QEEG") as being of no clinical value in 1987 and in 1997 as being of limited clinical use in (a) stroke, (b) dementia, (c) intraoperative monitoring, and (d) epilepsy. However, clinical utility was not accepted by AAN for application in (a) traumatic brain injury, (b) psychiatric disorders including learning disabilities, and (c) medical-legal use. While Hoffman et al. disagree with the AAN's limited recommendations for use of QEEG, they do not offer concrete alternatives for therapeutic application of QEEG in treating mental disorders. This is illustrative of the challenges posed by objective data such as neurometric/neurophysiologic information in general and EEG data in particular in treating mental disorders.

The neurophysiologic technique of EEG measures the electrical activity of the brain as a function of time varying spontaneous potentials (SP) through a number of electrodes placed at standard locations on the scalp. The neurophysiologic information obtained through EEG analysis is recorded as sets of traces of the amplitude of SP over time for scalp electrodes that are variably referenced. This analog EEG information can then be visually analyzed and interpreted for signal abnormalities.

In the 1970's, quantitative analysis of the EEG signal provided rapid easy access to measurements that extended the EEG method beyond qualitative visual detection of signal abnormality. Quantitative EEG (QEEG) studies involve the multi-channel acquisition, processing, and analysis of brain activity often but not exclusively by computers. An example of an EEG/QEEG instrument is the Easy Writer II system, available from Caldwell Laboratories, Inc. (Kennewick, Wash.).

In one version of EEG/QEEG recordings electrodes (at least one electrode, preferably nineteen electrodes and most preferably 21 electrodes) are commonly placed at standard locations on the scalp using the International 10/20 Placement System. A multi-channel recording of the brain's activity in an alert, awake, eyes-closed, or "background" state is then recorded and analyzed often by use of Fast Fourier Transform (FFT) signal processing. FFT processing of the raw EEG permits measurement and quantification of multiple characteristics of brain electrical activity. In this process, optionally, signals due to muscle or eye movement or environmental noise are rejected, leaving information related to neurophysiology for further analysis.

EEG recordings are typically of uncertain quality and often require the aid of an experienced technician. See, e.g., Nuwer, Marc, "Assessment of digital EEG, quantitative EEG, and EEG brain mapping: Report of the American Academy of Neurology and the American Clinical Neurophysiology Society" in *Neurology,* 49:277-292 at 279 (1997). Still, there are known methods for obtaining EEG data reliably by placing electrodes (satisfying specified impedance limits) relative to well-defined landmarks on the skull such as the International 10/20 system. U.S. Pat. No. 5,730,146 issued to Itil et al. on Mar. 24, 1998 discloses an apparatus for reproducibly placing electrodes, in accordance with the International 10/20 system, on the head of a subject and transmitting EEG data to a remote location over a telephone connection. U.S. Pat. No. 5,816,247 issued to Douglas E. Maynard on Oct. 6, 1998 discloses an apparatus and method for collecting EEG signals from a subject and subjecting the signals to sorting with the aid of a suitably trained neural network.

Not everyone with an abnormal EEG has an associated disorder—mental or otherwise. While EEG reveals gross changes such as spikes and disturbances accompanying seizures or the lack of brain activity associated with death, it is less than successful in providing a correlation with known mental disorders as defined by DSM-UV or its other editions. Similar difficulties are associated with correlating EEG/QEEG findings with other mental disorder diagnosis systems, such as the ICD.

DSM-IV manual has many detractors who disagree with various methodological details or conclusions therein as well as the basic strategy underlying the manual. However, in view of the reality of mental disorders and the therapeutic benefit possible with administration of substances and therapy to a subject to treat mental disorders such criticism does not provide practical alternatives to prescribing substances or treatment other than DSM-IV or a comparable diagnostic scheme. The previously mentioned lack of reliance on EEG recordings in making diagnosis reflects the lack of correlation between a diagnosis in accordance with the known systems for diagnosing mental disorders, such as DSM-IV, and EEG recordings. In the few instances when there is possible a correlation, such as advanced schizophrenia, there are obvious overt disease indicators that eliminate the need for EEG recordings in view of the added expense and technical demands made by EEG.

In addition to EEG, objective measures of brain activity include techniques such as magnetic resonance imaging (MRI), functional magnetic resonance imaging (FMRI), positron emission tomography (PET), single photon emission computerized tomography (SPECT), magnetoencephalography (MEG), quantitative magnetoencephalography (QMEG) and many others. All of these techniques are of limited significance in actual treatment of mental disorders for reasons similar to those discussed in the case of EEG recordings or cost issues or due to ease of use or a combination thereof.

Consequently, known attempts at integrating neurophysiologic information with treatment start with a definitive DSM, or similar, diagnosis followed by an attempt to identify variations in QEEG or EEG that correlate with the known diagnosis. An example of such an approach in the context of a diagnosis of chronic fatigue syndrome is provided by the U.S. Pat. No. 5,267,570 issued to Myra S. Preston on Dec. 7, 1993 for a "Method of Diagnosing and Treating Chronic Fatigue Syndrome." Similarly, in the context of a diagnosis of Alzheimer's dementia use of EEG data is disclosed by the U.S. Pat. No. 5,230,346 issued to Leuchter et al. on Jul. 27, 1993 for "Diagnosing Brain Conditions by Quantitative Electroencephalography." Another U.S. Pat. No. 5,873,823 issued to David-Eidelberg on Feb. 23, 1999 discloses a more generalized approach to detect markers to aid in screening patients for traditional diagnosis and treatment. The U.S. Pat. No. 5,083,571 granted to Leslie S. Prichep on Jan. 28, 1992 discloses discriminant and cluster analysis of EEG data in diagnosing mental disorders.

None of the aforementioned patents teaches integration of behavioral definitions of psychiatric disorders with objective data in view of the response of a subject to treatment of the mental state of the patient independent of the diagnosis. Instead, they focus on refining the diagnosis of traditional behavioral psychiatric disorders with the aid of objective data.

It is not unusual for a therapeutic entity prescribed for a particular mental disorder to entirely fail to alleviate the symptoms or to even result in additional or different symptoms. In other words, in addition to weak correlation between traditional diagnostic systems and objective data, the correlation between traditional diagnosis and treatments is also significantly less than desirable.

The absence of a strong correlation between objective data collected from a subject and the known analytic techniques, such as DSM-IV, makes it difficult to discover and utilize the likely utility of a given substance or therapy upon administration to a subject. Indeed, identifying a subject as having an abnormal neurological profile needs a more objective basis than that afforded by subjective data to reduce errors in treatment and improve the likelihood of a successful outcome for a course of treatment.

Moreover, many known substances and currently available therapeutic entities have yet unknown useful effects on the mental state. Reliance on more subjective observational data based on narrated case history or observations often masks useful properties of many known substances. Often, in providing information to modify behavior it is difficult to prospectively persuade a subject that the risk of harm or addiction is greater in the subject's case compared to the general population. Thus, the generation of neurophysiologic information provides a useful tool for designing and implementing outreach programs.

Some substances are of considerable social and political import since the users of such substances are a very small fraction of the general population, and consequently their needs are easily overshadowed by the cost of servicing and locating such users. While the present laws encourage such users through provisions such as identifying "orphan drugs" for special treatment, the cost of identifying even the condition to be targeted by a putative orphan drug poses a challenge. Better identification of orphan drugs would not only improve treatment availability, but actually provide customized treatment to a wide spectrum of subjects.

Moreover, additional substances have addiction associated with their administration. Examples include nicotine, typically self-administered by inhaling fumes, and many other substances whose sale is restricted or prohibited by law. However, educating the public to the dangers posed by such substances is difficult in the absence of a customized risk assessment of deleterious responses and the propensity to exhibit addiction. Presently, there is no method or system for providing such customized yet prospective information as part of public education campaigns and preventive care.

The aforementioned shortcomings are overcome by the present invention, described below, in addition to new capabilities enabled in its various embodiments.

SUMMARY OF THE INVENTION

The invention provides a system and method for choosing a treatment independent of a diagnosis based on a treatment-response database of responses to treatment. Evaluation of a subject includes obtaining neurophysiologic information in an initial state of the subject. Active-treatment neurological information of the subject is, then, obtained along with an evaluation of whether the subject exhibited improvement, non-responsiveness or adverse reactions to the treatment. Statistical techniques isolate factors in the initial state shared by a group of subjects exhibiting similar responses in a treatment-response database of responses from several subjects.

Searching this treatment-response database to find treatments associated with a desirable response in a subject having a particular initial neurophysiologic state enables evaluation of the likely effect of a proposed treatment on a subject with concomitant reduction in unnecessary experimentation.

Active-treatment neurological information coupled with pretreatment and/or initial state neurological information is also useful in drug-abuse programs by identifying candidates for adverse effects of therapeutic entity. These candidates can then be provided individually tailored information prior to actually experiencing the full range of the adverse effects as an effective and specific warning of the consequences resulting from drug abuse.

The techniques for building the treatment-response database are extended to enable, for instance, discovering if a particular therapeutic entity having failed to exhibit a positive outcome in testing is nevertheless effective in a smaller subset of patients.

Similarly, design of clinical trials is improved by selection of a set of subjects most likely to respond in a desirable manner to a proposed therapeutic entity. This both lowers the development costs and makes the testing safer with superior guidelines for actual clinical use of the candidate therapeutic entity.

In still another aspect of the invention objective data is further applied to discover new candidate therapeutic entities and new uses for known therapeutic entities. Moreover, a subject and a method of treatment are matched objectively to reduce the likelihood of deleterious or undesired side effects due to treatment in clinical practice or clinical trials. Furthermore, the embodiment of the invention includes designing clinical trials with a better defined set of subjects to increase the likelihood of discovering both the beneficial and deleterious side effects of a therapeutic entity along with an analytic frame work to identify and correct for non-responsive subjects.

Thus, a therapeutic entity deemed to have marginal efficacy on an undefined pool of subjects is evaluated for its effect on subjects who can be differentiated with the aid of prospective and/or retrospective analysis to determine whether they are likely to be responsive, adversely affected or non-responsive. This, in turn, enables better use of a candidate therapeutic entity in actual treatment subsequent to the clinical trials by identifying condition precedent for successful use of the therapeutic entity in clinical practice.

In another aspect, the invention enables screening subjects for a common response to a treatment as indicated by neurophysiologic information. Such patients, then are an enriched set for identifying a common underlying mechanism at the molecular level and genetic level. In particular, shared family history for a particular response pattern to one or more therapeutic entities enables identification of common genetic determinants underlying the response to the treatment.

In another aspect the invention discloses techniques for construction and maintenance of useful databases for making treatment recommendations for modulating brain function.

In still another aspect, the present invention enables remote assessment and treatment of physiologic brain imbalances using objective data such as quantified neurophysiologic information. The treatment-response database enabled by the invention can be accessed either directly or from a remote location, thus providing high quality information to practicing physicians via electronic or wireless links as well.

The invention further provides effective user-interfaces, portable devices, computer software, computer programming techniques, and algorithms for conducting the neurophysiologic analysis, remote transmission, and treatment methods described herein.

DETAILED DESCRIPTION OF THE INVENTION

Figure 1:
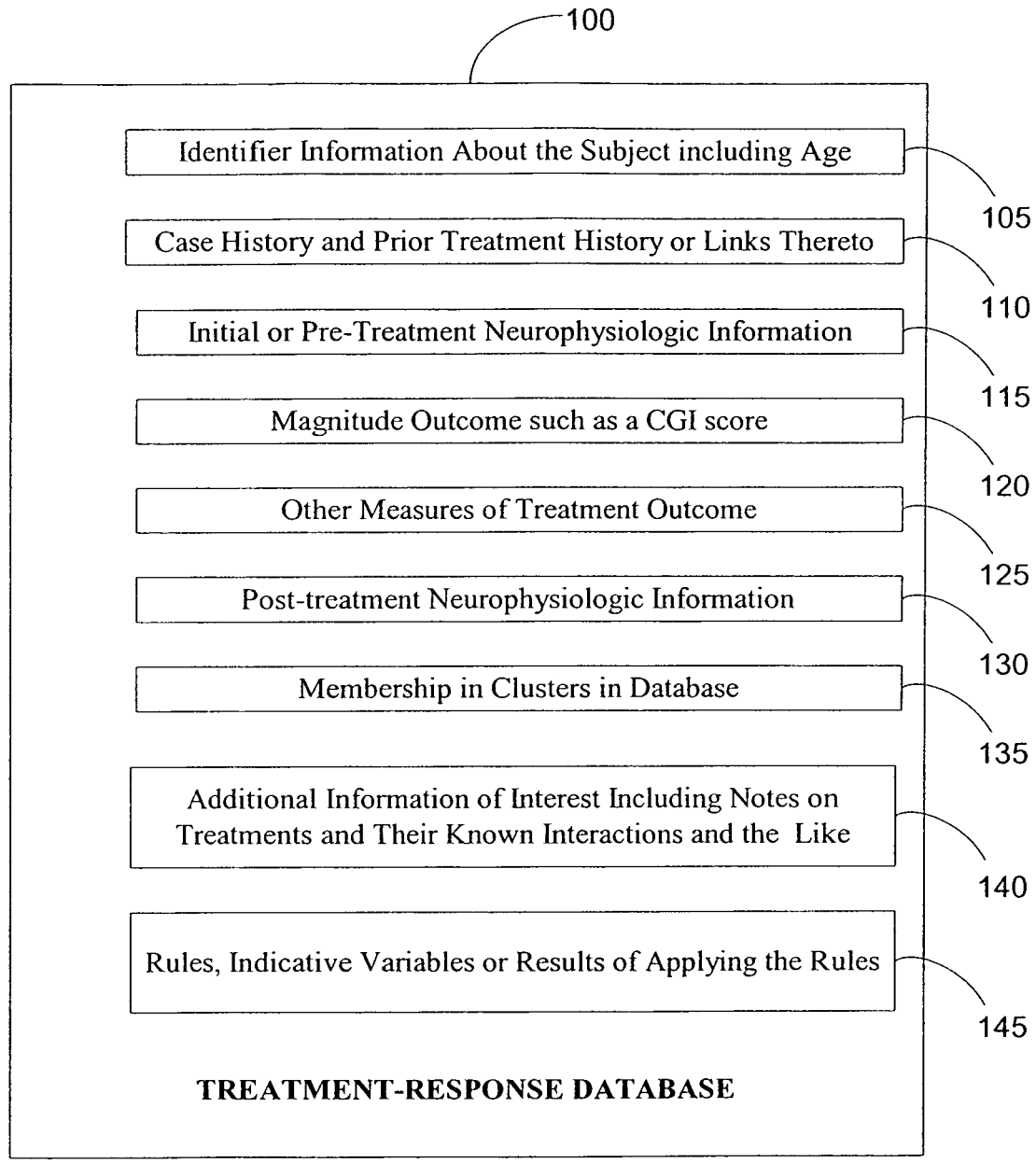
FIG. 1 is a schematic of a treatment response database taught by the invention.

The present invention is directed to a method and system for modulating a subject's brain physiology. The invention enables integration of neurophysiologic information and behavioral data for predicting the outcome of treatment of a subject. In an important respect, the prediction is independent of the traditional diagnosis, and, thus is not limited by the accuracy of the clinical diagnosis or the behavioral data underlying the clinical diagnosis.

The present invention is based, in part, upon the inventors' discoveries that quantitative neurophysiologic information, preferably including quantitative electrophysiologic information, is a reliable indicator by which to choose therapies for individuals with behaviorally-diagnosed psychiatric conditions and to predict outcomes from selected therapies. It has been discovered that such quantitative information is more reliable and useful for guiding treatment of mental disorders than traditional diagnostic classifications arrived at by standard qualitative psychiatric procedures known in the art, which are largely based on interview, observation, and the like. In fact, according to the present invention, effective therapy is administered with little if any attention to the particular behavioral diagnosis.

The inventors believe, without limitation, that quantitative electrophysiologic information, such as than obtained from quantitative electroencephalogram recordings (QEEG), reflects more closely underlying central nervous system (or, more specifically, brain) physiological functioning upon which therapies, specially therapeutic entity therapies, directly act. Indeed, QEEG data provides regional information (anterior, central, posterior, left, and right) on CNS functioning which reflects the well-known regionalization and lateralization of CNS functioning. In contrast, qualitatively reported or observed behavior is believed to be a net result of many factors so that any given behavior may be the single outcome of at least several different constellations of CNS physiological functioning, each constellation best addressed by different therapies. Accordingly, it is believed that quantitative neurophysiologic information is more reliable for selecting therapy than is traditional behavioral diagnosis alone.

Therefore, according to the present invention, therapies for behaviorally-diagnosed psychiatric conditions are selected according to the indications of quantitative neurophysiologic information. Prior to the present invention, therapies were selected primarily solely on the basis of the behavioral diagnosis, such as a diagnosis according to a standard like the DSM-IV. It is well known, however, that therapies so selected are often ineffective, or less than sufficiently effective, or may actually exacerbate the original complaint. Therefore, practitioners expected significant trial and error, unpleasant side-effects, cost, patient effort, and so forth in arriving at an effective therapy. Thus, this invention provides a method and system for improving the likelihood of selecting an effective treatment the first time, with or without a preceding traditional diagnosis of a mental disorder.

Until the present invention, quantitative neurophysiologic and QEEG data was not thought to be useful for treatment selection because the great complexity of this data effectively hid the information that the present invention is able to discern. Originally, EEG data was presented only as analog waveforms, which were useful only to detect striking abnormalities in the time domain. Thus, EEG data has long been used to diagnose prominent epilepsies. Analog data could not be used to detect subtle changes in physiological functioning of the CNS. Although quantitative EEG techniques produced numerical measures of EEG activity, QEEG data also hid useful information in the many hundreds to substantially more than a thousand separate measures of EEG structure. These measures include principally Fourier transforms, amplitudes, and correlations of unipolar data, which is derived from signals recorded from single EEG leads, and bipolar data, which is derived from combinations of signals from two EEG leads.

In view of the basic discoveries underlying the present invention, the inventors have further discovered methods and systems for extracting information useful for therapy selection from this mass of formerly impenetrable quantitative neurophysiologic data. These novel methods are now briefly and generally described in order to prepare for the specific descriptions of particular embodiments and applications of these methods and systems which occurs subsequently. The present description is a non-limiting summary, while the subsequent specific descriptions present actual details of the various embodiments and applications consistently and completely.

Therefore, generally, the methods of the present invention begin with data collection for a number of individuals, where for each individual the data (collectively named, for example, a therapy-response database) includes at least an initial QEEG data, a therapy which is then administered, and a quantitative assessment of the response to therapy. Preferably (and not limiting), the individuals in the database have a behaviorally-diagnosed psychiatric condition; their initial QEEG is taken in a therapeutic entity-free condition; QEEG data is transformed to reflect a relative deviation from observations made in individuals without any psychiatric symptoms; and a single therapy is then administered. The database, of course, can include additional data on each individual, for example, the traditional behavioral diagnosis.

For the purposes of description only (and without limitation as to implementation), the methods of this invention can be described and visualized in spatial terms. Thus, the therapy-response database can be represented as points in a space (QEEG space). QEEG space has a large number of dimensions, typically substantially more than one thousand dimensions, one dimension recording the values of each (normalized and "raw") QEEG measure. Each point represents an individual in the database, the point positioned according to the individual's QEEG measures and labeled both by the individual's therapy and whether or not the individual was responsive to the therapy administered. Next, as discovered by the inventors, points (that is, individuals) that are responsive to particular therapies tend to be arranged in "clusters," or in "localized" groups in QEEG space. Although, these clusters or groups may be thought of as, for example, "galaxies" of responsive individuals, the shapes of these galaxies are not limited to compact regions, but are most often highly, even unimaginably, complex regions in this thousand-plus dimension space.

However complex, in an embodiment of the invention the boundaries of these clusters of responsive points define the QEEG measures, that is the structures of a new patient's EEG, which predict likely response of that patient to the therapies defining the clusters. In other words, if the point representing the new patient's QEEG is in or near a cluster defined by a particular therapy, then that therapy is selected for the new patient according to the invention.

It is important, and one principal aspect of this invention, that this clustering is largely independent of behavioral diagnosis. The clusters are preferably defined by being responsive only to particular therapies; other clustering conditions, such as diagnosis, are preferably not used. If, in an embodiment, diagnosis is part of the clustering, only the most general diagnostic information is useful. For example, it may be useful to cluster separately individuals whose behaviorally-diagnosed psychiatric condition depends on other medical conditions from those not having such identifiable conditions. Such conditions might include metabolic abnormalities due to renal or hepatic disease, tumor, trauma, and the like. In contrast, the prior art teaches just the opposite, namely "clustering" individuals according to their diagnosis (that is "diagnosing" individuals) and then using such diagnostic clusters to select therapies in a conventional manner. To the extent QEEG data has been objectively used in psychiatry prior to the present invention, it has been to diagnose, with therapy selection dependent on diagnosis. The present inventors have discovered that methods opposite to the prior art are considerably more effective.

The methods of this invention now proceed by finding and representing the boundaries of the clusters or groups of points (individuals in the database) responsive to a particular therapy. In one embodiment, identification and representation of groups is performed directly in the thousand-plus dimension QEEG space. This is advantageous in that clusters are most accurately represented without approximation in this space defined by the full complement of measures representing the structure of a patient's EEG. It is less advantageous in that representing shapes and boundaries in such a high dimensional space is laborious. In this space, cluster boundaries may be represented by functions of the thousand-plus dimensions. For example, a cluster for therapy T may have a boundary represented by function, f, so that for a patient point, p, if f(p)>0 then p is in the cluster. In this case, T is indicated for patient p, and not indicated for patients q with f(q)<0. Thus, f=0 may be considered as defining a ":hyper-plane" dividing patients for which T is indicated from other patients. However, even if for a patient q, f(q)<0, for example, therapy T may still be considered if the point q is sufficiently "close" to the defined cluster. As most generally understood, such functions, which mark out the boundaries of clusters, define "indicative variables," that is variables indicating, or not, particular therapies.

Therefore, in preferred embodiments, QEEG space is projected, or more generally, mapped (or both projected and mapped) into a "reduced" QEEG space (simply, a reduced space) of lower dimensions in such a manner that clusters or groups of responsive patients are substantially preserved. Preferably, the reduced space has between 50 and 200 dimensions, and more preferably, the reduced space has between 50 and 100 dimensions, while less preferably the reduced space has more than 200 hundred dimensions. The actual number of dimensions in an implementation is limited by the effectiveness of the available clustering techniques and the computational resources for performing this clustering. Projections are preferably defined by dropping QEEG measures that are determined to make little contribution to clustering in the reduced space, where the contribution of a measure may be determined by analyzing the sensitivities of clusters in the reduced space to the particular measure.

A mapping is preferably defined by combining disjoint sets of multiple QEEG measures into single variables that define the coordinates in the reduced space (for example, combining sets of 10 QEEG measures into single variables reduces 1000 dimensions to 100 dimensions). Preferably, the disjoint sets include QEEG measures having related physiological significance. For example, monopolar signals are combined to represent the power spectrum (divided in the standard frequency bands of alpha, beta, delta, and theta) in the standard anatomic regions (anterior, central, posterior, left, and right). Bipolar signals are combined to represent the power spectrum of simultaneous activity between various brain regions, for example, across the midline. Measures in the sets are generally combined according to functions monotonic in all variables, such as linear combinations, non-linearly normalized linear combinations, sigmoidal functions, or so forth.

In the following detailed descriptions, QEEG measures are often called "univariate measures," or "univariates," or "univariables," or so forth. The variables defining the reduced space are called "multivariate measures," or "multivariates," or "multivariables," or so forth. In preferred alternatives certain dimensions of the reduced space are defined by single univariables, or by raw QEEG measures, such as absolute power. Preferred actual mapping/projections are presented as tables defining the multivariables into terms of the univariables. Further, actual mappings (as well as the number of reduced space dimensions) may be iteratively improved by comparing clustering or groups in QEEG space with the mapped clusters in the reduced QEEG space, and adjusting the mapping so that mapped clusters reproduce the original clusters with substantial fidelity.

Thus, in preferred embodiments, cluster boundaries are determined and represented in a reduced QEEG space. Here, as in QEEG space, cluster boundaries may be represented by functions, or "indicative" variables, which are more manageable being functions of, preferably, 100 or fewer variables. In both spaces, clusters or groups defined by therapy responsiveness may be determined by known clustering methods, for example, statistical methods such as tree clustering, k-means clustering, and the like. Alternatively, cluster boundaries (and indicative variables) may be found and represented by neural networks. Also, cluster boundaries are typically approximate, or "fuzzy." Preferably, a boundary is chosen so that a determined percentage of the individuals responsive to the therapy being clustered are within the boundary, while a similar determined percentage of all the individuals responsive to the therapy are within the boundary. A practical determined percentage has been found to be 80%; other percentages may also be used, for example, 55%, 60%, 70%, 90%, 95% or higher.

In a further preferred embodiment, a reduced QEEG space may be further simplified, without essential loss of clustering, into what can be conceptualized as a multi-dimensional binary cube (a "binary" reduced QEEG space), that is as the space $\{0, 1\}^N$ ("0" and "1" may represent, for example, "true" and "false"). In a particular preferred embodiment described subsequently, N=72. This binary space is realized by, for example, dividing the range of each coordinate, or parent multivariable, defining a reduced space into two portions so that a corresponding "reduced" multivariable has the value 1 if the value of the parent multivariable is in the first portion, and is 0 otherwise. Thus a reduced space may be further mapped into a binary reduced space. A preferred method for dividing the range multivariables is to select a first portion with more probable values, or more normal values, and a second portion with less probably, or more abnormal values. For example, more and less probably may be systematically chosen as 1 or 2 standard deviations from a normal average. In this embodiment, reduced multivariable are called "rules" in the following, and the value 1 or true (or 0 or false) is assigned to the less (or more) probable values. In alternate embodiments, parent multivariable ranges may be divided into three or more portions.

It has been found possible, through an iterative process or trial and improvement, that the multivariable and their ranges defining a binary reduced space may be chosen so that cluster boundaries have a particularly compact representation, which is most conveniently illustrated by example. Thus, consider that $R_i$ (i=1, ..., N) are reduced multivariables, or rules, defining a reduced space; and also that, for example ($R_1$=0) is 1, or true if $R_i$ is in fact "0," and is 0 or false if $R_1$ is in fact "1" (and conversely for ($R_1$=0)). Then cluster boundaries might be represented by exemplary Boolean functions. For example, an exemplary Boolean function is $f(R_1, R_2, R_3, ..., R_N)$=($R_1$=1) & ($R_1$=0) & ($R_K$=0) & ($R_L$=1), which might define the cluster f>0 (with f<=0 being not in the cluster). Boolean functions, which represent rule combinations are a particularly preferred representation of an "indicative" variables. For example, general Boolean functions, perhaps expressed in conjunctive or disjunctive normal forms, are capable of representing general decision trees of rules. Certain subsequently described particular embodiments, which express clusters in decision trees, may thus be alternatively expressed with Boolean indicative variables.

Although this invention has been described in terms of clustering according to outcomes of individual therapies, considerations of statistical significance and computational complexity may make clustering of lower resolution preferable. For example, a particular therapy-response database may have an insufficient number of symptomatic individuals to allow clusters for all individual therapies to be determined with reasonable significance. Certain therapies are simply rare in or absent from the database. Alternatively, the computational cost of finding, defining, and mapping all such clusters may be too high even if sufficient individuals were present. In these, cases therapies may be grouped, and clusters of individuals responsive to any therapy of the group are determined. Typically, therapies group according physiological similarity. For example, all therapies known to effect a particular neurotransmitter system in a particular manner group together. Thus, clustering is of varying degrees of resolution.

Now summarizing this general description, according to the present invention therapies are selected, and therapeutic outcomes are selected, for patients with behaviorally-diagnosed psychiatric conditions not according to behavioral diagnosis, but instead by comparison to a database of symptomatic individuals who have had positive responses to various therapies or classes of therapies. Therapies are then selected for a patient that have been successful in similar individuals. According to the invention, similarity is assessed by comparison of the patient's quantitative neurophysiologic information with that of the individual in the database. Preferably, the quantitative neurophysiologic information compared includes QEEG data, and the comparison proceeds by first clustering the quantitative information into clusters or groups predictive of response to the various therapies represented in the database.

This clustering and comparison proceeds in the original QEEG data space. More preferably, the original QEEG space is mapped into reduced spaces that permit simpler clustering and comparison while preserving the group structures present in the original data space. Such a mapping is, for instance, made by combining the univariate measures defining the original data space into multivariate variables, where each multivariate variable is a combination (linear or non-linear) of data measures reflecting similar CNS physiological activities. Further, a reduced space is "discretized" by specifying ranges for the multivariate variables that correspond, for example, to normal and abnormal (for example, in a statistical sense) and assigning discrete values to the reduced multivariate variables, known as "rules" in this embodiment. Discretization preferably results in a space similar to a high-dimensional binary cube. In whatever space, the boundaries of therapeutic clusters define characteristics of a patient's quantitative neurophysiologic information predicting a responsive outcome to the associated therapy. These boundaries are defined by functions, known as indicative variables. In a binary reduced space, indicative functions are rules and Boolean combinations of rules.

This general description is not limiting at least in that these methods are applied to arrive at results other than selection of a therapy for a patient. For example, as described subsequently, these methods are used to select multi-therapies; or they are further be used to select patients likely to respond to a therapy under test. Further, a cluster contains further information. Since clustering or grouping is independent of diagnosis, a cluster associated with a likely response to a particular therapy usually contains individuals having many diagnoses, even though they have similar quantitative neurophysiologic characteristics. Accordingly, the methods of the present invention lead naturally to the use of therapies for new diagnoses, i.e., for patients with diagnoses that heretofore were not treated with the now indicated therapies. The therapeutic armamentarium of the health professional is thereby broadened.

Lastly, before a more detailed description of particular embodiments and aspects of the present invention, the meaning of certain common useful terms are explained. Typically, these meanings are clear from the context, and correspond to the understanding of one of ordinary skill in the art. Use of these terms in a contrary fashion is indicated when appropriate.

"Behaviorally diagnosed" is taken to refer to individuals who have psychiatric complaints that are classified according to a system of psychiatric diagnosis, preferably according to a standard system. Preferably, the psychiatric complaints and the behavioral diagnosis are primary, and not secondary to other medical conditions such as metabolic abnormalities or anatomic lesions. The present invention is applicable to those with other conditions. However, it is preferably to group such patients separately from those without other conditions.

In more detail, behavioral diagnosis is diagnosis of mental illness based on behavioral indicia, as observed by psychiatrists and other health care professionals and codified by the DSM-IV, or its other editions (American Psychiatric Association. Diagnostic and Statistical Manual of Mental imbalances. *DSM IV, Fourth Edition*. Washington, D.C.: American Psychiatric Association), or the International Classification of Diseases (ICD) (posted at http://cedr.lb1.gov/icd9.html, last visited Jan. 26, 2000) or similar classification systems.

"Neurophysiologic information" is the quantitative information measured from the brain or from the CNS generally. It may includes quantitative measures of anatomic information concerning the CNS generally, such as that obtained by magnetic resonance imaging (MRI) or computerized tomography (CT). It also may include information measuring metabolic or other biological processes occurring in the CNS, such as that obtained by functional MRI, positron/electron tomography (PET), or single photon emission computer tomography (SPECT). This quantitative neurophysiologic information is distinguished from behavioral information, relied upon for making traditional diagnosis, obtained from interviews, observation of behavior, impressions and reports of impressions of delusion, confusion, responsiveness, dexterity and the like.

The nature of the quantitative neurophysiologic information. especially the conditions during its recording, has been found to be important so that selected therapies or predicted responses will accurately reflect what will be observed during the routine daily functioning of patients. Simply, it is preferable that data be recorded from patients undisturbed and in a normal state of consciousness. For example, consciousness should not be impaired by sedative agents, hypnotic agents, anaesthetic agents, or the like; also, patients should not be asleep or drowsy. Patients should be normally alert and awake during data collection. Further, since it has been found that background functioning of the entire CNS reflects treatment outcomes, patients should not be disturbed during data collection.

Preferably, therefore, quantitative neurphysiologic information includes electronic or magnetic impulses reflecting ongoing CNS activity in a patient in a comfortable, resting, but alert state without sensory stimuli. The eyes should be closed and the environment free from disturbance. Information so recorded has been found to reflect the background functioning useful in the present invention.

Most preferred in current embodiments is data from EEG or magnetoencephalography experiments where the patient is resting, with eyes closed, but alert. Currently, most preferred is QEEG information, which is EEG information which have been digitized and Fourier transformed, and, possibly, expressed as deviations from observations in patients without psychiatric or medical conditions. Naturally, information useful in this invention typically does not include bispectral indicia, special sensory evoked potentials or nocturnal polysomnographic data. However, this is not intended to indicate that the methods of the present invention are not useful in enhancing the analysis of such information.

This quantitative neurophysiologic information is distinguished from behavioral information, relied upon for making traditional diagnosis, obtained from interviews, observation of behavior, impressions and reports of impressions of delusion, confusion, responsiveness, dexterity and the like.

"Reference distribution" is a distribution or a set of values useful for measuring significant deviations from normalcy as opposed to random variations. A reference distribution need not always be obtained from data taken from exclusively asymptomatic subjects. In an embodiment of the invention, a reference comprises data points, corresponding to "normal" or asymptomatic age-matched controls, exhibiting a Gaussian distribution.

"Z-scores," a type of normalization transformation, are uniform differential probability scores. The difference between an observed neurophysiologic value and the expected reference mean, such as "age-adjusted normal" mean divided by the expected reference standard deviation, such as "age-adjusted normal" standard deviation yields a Z-score corresponding to the observed neurophysiologic value.

A "magnitude-outcome" (or a quantitative or objective outcome) of a treatment is a score of the relative magnitude of the change in a patient's psychiatric condition, rather than a description of its details. Quantitative outcomes permit comparison of the same therapy in different conditions or of difference therapies for the same condition. An illustrative example is the clinical global improvement scores ("CGI") providing a numerical score in the range [−1, 3] to indicate the effect of a treatment. Of course, binary state changes are included in such an outcome indicator. Moreover, magnitude outcome includes reliance on a steady state for a prescribed period of time or use of tests that yield information that can be compared to that from prior to administering a treatment.

A "multivariable" is a combination of univariate variables identified as being significant in describing or characterizing a cluster of subjects. The univariate variables are often scaled in the course of making the combination to ensure reference to a uniform scale with requisite sensitivity. In particular multivariables define a mapping or transformation from a typically very high dimensionality data space to a more tractable lower dimensionality space for performing the methods of this invention.

A "treatment" or "therapy" may include any known psychiatric therapy, including for example therapeutic entity therapy, talk therapy, convulsive therapy, photo therapy, and so forth. Preferably, the present invention is applied to therapies including the administration of a therapeutic entity or combination of therapeutic entities. In one sense a treatment includes a class of therapeutic entities and therapy while in another sense it includes a specific agent.

A "paroxysmal event" is a brief sudden disturbance in the background EEG easily visualized in the time domain. It often consists of short duration spikes and waves, which are often but not always accompanied by a sudden voluntary or involuntary muscle movement.

A "nonparoxysmal event" is an artifact-free background EEG, the artifacts being the short duration spikes and waves indicative of a paroxysmal event.

"Approved practice" (or "approved clinical practice" or "approved therapeutic practice") refers to the uses of therapies, in particular of therapeutic entities, approved by the relevant regulatory body, which in the United States is the Food and Drug Administration (FDA). Such regulatory bodies typically approve therapies for use only after their safety has been established, and usually also only after their efficacy has been proven in clinical trials. In the United States, approved practice is indicated on FDA approved labeling, which for therapeutic entities, is gathered in the Physician's Desk Reference.

Returning to the description of the invention, the invention is based, in part, upon the discovery that neurophysiologic information can and needs to be relied upon to greater extent than the customary practice in treating patients. It is typical for a subject diagnosed in accordance with a standard like DSM-IV to undergo a treatment only to discover that the treatment is ineffective. Moreover, many treatments recommended for the same DSM-IV diagnosis may actually exacerbate the original complaint resulting in significant trial and error with its unpleasant side effects. In an aspect, the invention provides a method and system for improving the likelihood of selecting an effective treatment with or without a preceding traditional diagnosis of a mental disorder.

More particularly, the method of the invention employs neurophysiologic information for assessing, classifying, analyzing and generating treatment recommendations for modulating brain function. Neurophysiologic information used independently of a traditional diagnosis enables an independent estimation of the likely response of a particular subject to a treatment of, among other things, mental disorders. Notably, the invention has broad utility in providing a method for modulating brain function in general.

Now, detailed aspects and embodiments of the present invention are described. Each such embodiment or aspect is intended for separate application. In an embodiment of the invention, neurophysiologic information collected from a subject is transformed to enable its comparison with like data from other subjects. The neurophysiologic information employed in the present invention is collected with the aid of instruments. Such information yields objective information in the form of EEG/QEEG signals, MRI signals, PET signals, SPECT signals, and the like that are distinguishable from the traditional behavioral observations of a subject to diagnose a mental disorder.

More particularly, the methods of the invention employ neurophysiologic information for assessing, classifying, analyzing and generating treatment recommendations for modulating brain function. Neurophysiologic information used independently of a traditional diagnosis enables an independent estimation of the likely response of a particular subject to a treatment of, among other things, mental disorders. Notably, the invention has broad utility in providing a method for modulating brain function in general.

Although the invention is described herein in its various embodiments enabling a broad range of neurophysiologic data, most preferably including EEG data, to select therapy or predict therapeutic outcomes, the present invention is to be understood to have application to disease categories in addition to behaviorally diagnosed psychiatric conditions. A first category includes central nervous system (CNS) conditions that are considered on the boundary of psychiatry and neurology, being considered either psychiatric or neurologic. For example, central pain syndromes are such conditions. The techniques of the present invention, in particular selecting therapy based on a comparison of a patient's neurophysiologic data with a database of similar patients having successful outcomes to a variety of treatments, may be successfully applied to this category.

A second category is patients having primarily neurological disorders with a psychiatric component. Depression secondary to loss of function due to stroke is such a condition. For this category it is preferably to focus attention on a patient's, and on comparable individuals', EEG data. Here, the techniques of the present invention are applied to EEG data by comparing a patient's EEG data to a database of the EEG data from successfully treated individuals (the comparison being preferably expressed also as rules, as explained subsequently). Finally, the present invention is applicable to patients with frankly neurologic conditions. By focusing on EEG data for these patients, centrally acting therapies are recommended to alleviate part, or a substantial part, of their symptoms.

Briefly, in an embodiment of the invention, neurophysiologic information collected from a subject is transformed to enable its comparison with like data from other subjects. The neurophysiologic information employed in the present invention, collected with the aid of instruments, yields objective information in the form of EEG/QEEG signals, MRI signals, PET signals, SPECT signals, and the like that are distinguishable from the traditional behavioral observations of a subject to diagnose a mental disorder. In an embodiment of the invention, the neurophysiologic information is transformed relative to a reference distribution, e.g., a Z-transform to gauge deviation from the reference distribution and permit comparison among various measures comprising neurophysiologic information.

In an illustrative embodiment of the invention, EEG information is collected from electrodes placed at standard locations on a subject's scalp using, by convention, the International 10/20 System for electrode placement. The information is digitized and then undergoes fast Fourier transform (FFT) signal processing to yield a QEEG spectrum. In addition to quantifying the power at each frequency averaged across the QEEG spectrum for each electrode, FFT signal processing of the raw EEG signal provides measurement and quantification of other characteristics of brain electrical activity.

The QEEG spectrum is presently divided into four frequency bands: delta (0.5-3.49 Hz); theta (3.5-7.49 Hz); alpha (7.5-12.49 Hz); and beta (12.5-35 Hz). The spectrum also includes the results from each of the EEG electrodes represented as quantitative output measurements for each frequency band. These include absolute power in each band ($\mu V^2$); relative power in each band (percentage power in each channel); coherence (a measure of synchronization between activity in two channels); and symmetry (the ratio of power in each band between a symmetrical pair of electrodes). It should be noted that alternative band descriptions, including new standards being debated, are intended to be within the scope of the invention.

Although not intended as a limitation of the invention, the relationship between these univariate measurements and brain activity is as follows. Absolute power is the average amount of power in each frequency band and in the total frequency spectrum of the artifact-free EEG information from each electrode, and is believed to be a measure of the strength of brain electrical activity. Relative power is the percentage of the total power contributed for a respective electrode and a respective frequency band, and is believed to be a measure of how brain activity is distributed. Symmetry is the ratio of levels of activity measured between corresponding regions of the two brain hemispheres or regions within an hemisphere in each frequency band and is believed to be a measure of the balance of the observed brain activity. Coherence is the degree of synchronization of electrical events in given regions of the two hemispheres or regions within an hemisphere and is believed to be a measure of the coordination of the observed brain activity. For instance, Using the aforementioned univariate measures, univariate Z scores, or uniform differential probability scores are calculated. Univariate Z-scores for a quantitative output measurement are calculated, by dividing the difference between an observed value and the mean for the expected "normal" value by the standard deviation of the expected "normal" value. The "normal" values are provided by a commercially available database such as the "Neurometric Analysis System" manufactured by NxLink, Ltd., of Richland, Wash. Information regarding this product is presently accessible at the web-site (http://www.biof.com/nxlink.html; last visited Jan. 25, 2000). The Z-transformation process scales all relevant information into units of probability (or units reflecting probability), yielding a uniform scale in all dimensions that can simplify further comparisons and evaluations of relationships between features.

An EEG/QEEG instrument, such as the Spectrum 32, manufactured by Caldwell Laboratories, Inc. (Kennewick, Wash.), readily executes these univariate neurometric Z transformations. This instrument contains age-defined norms in databases of age regression expressions defining a distribution of features as functions of age in a normal/asymptomatic population. The instrument extracts from the database the mean value and the standard deviation to be expected for each feature of a group of "normal" subjects the same age as a patient. It, then, automatically evaluates the difference between the value of each feature observed in the patient and the age-appropriate value predicted by the database age regression expressions. The instrument subsequently evaluates the probability that the observed value in the patient belongs to the "normal" group, taking into account the distribution of values in the "normal" group. A completely analogous process can be accomplished using a family of different digital EEG machines and commercially available neurometric software, such as that available from NxLink, Inc.

The example asymptomatic neurophysiologic information database includes the QEEGs, i.e., neurophysiologic information, of individuals from 6 to 92 years of age incorporating information from electrodes placed in accordance with the international 10/20 System. The asymptomatic database contains over 1000 quantitative univariate EEG measures. The Z-score, obtained by comparing an individual patient's QEEG information with the information for the reference asymptomatic population, represents the patient's statistical deviation from the reference-asymptomatic database. Thus, if a patient's Z-score for a particular measure does not statistically deviate from the reference asymptomatic population, the patient would be determined to be "asymptomatic" for that measure. However, if a patient's Z-score statistically deviates from the reference population for a particular measure, the patient is determined to be symptomatic for that measure. Notably, mere examination of a Z-score reveals the extent of deviation since a value of greater than one indicates a deviation of more than one standard deviation from the expected mean.

A treatment-response database of symptomatic individuals is created in accordance with the invention or a readily available treatment-response database, such as the outcome database owned by CNS Response of Long Beach, Calif. USA, accessed to generate one or more indicative variables. Alternatively, in an exemplary embodiment of the invention, the indicative variables are provided directly to enable analysis of univariate data with the aid of rules. An exemplary embodiment is implemented as a hand-held or portable device, or software for execution on computing machines such as personal organizers, personal computers or workstations, or even software accessible over the internet. The generation of the rules and the identification of indicative variables, such as multivariables, underlying the practice of the invention is described next.

In an embodiment of the invention, an indicative variable is determined from neurophysiologic information. A multivariable obtained by combining various univariate variables describing a cluster of neurophysiologic information is an example of such an indicative variable. Such multivariables enable searching a database, for instance, for identifying responses to a particular treatment, or a group of subjects having similar multivariable values (and their associated treatments) and the like. Or alternatively, testing the multivariable by applying rules enables evaluating a treatment's outcome in a particular subject. Typically, more than one multivariable is generated and the result of applying various rules to the values of respective multivariables is compared to the expected result for a particular treatment or outcome. Thus, the outcome of a particular treatment can be estimated as well as possible treatments ranked or merely listed to provide a practitioner with a prediction of the efficacy of various options.

Initial or pretreatment neurophysiologic information, classified as abnormal based on comparison to the neurophysiologic data from a reference population, enables generation of a treatment-response database, e.g., an outcome database in an embodiment of the invention. This example outcome database contains neurophysiologic information from symptomatic individuals exhibiting clinical manifestations of psychiatric disorders and an indicator of their response to treatment as indicated by active-treatment neurophysiologic information.

A typical treatment-response database 100 illustrated in FIG. 1 comprises entries containing identification information 105, case history of the subject including prior treatment history 110, initial or pre-treatment neurophysiologic information 115, magnitude-outcome of at least one of the treatments 120, other measure of treatment outcome 125, active-treatment neurophysiologic information 130, membership in clusters 135, additional information such as notes on different therapeutic entities and their known or suspected interactions 140, and rules, indicative variables or results of applying the rules 145. Of course, not every embodiment of treatment-response database 100 need have all of the possible entries listed in a non-exhaustive manner in FIG. 1. It is expected that typically treatment-response database 100 will have entries corresponding to at least twenty-five subjects, preferably entries corresponding to at least one hundred subjects and even more preferably entries corresponding to at least three hundred subjects. In an exemplary embodiment of the invention treatment-response database 100 is dynamic and distributed. For instance, interconnection of several small databases on different computers, each possibly compiled in the course of various otherwise independent studies, provides an embodiment of treatment-response database 100 taught by the invention. Each of the entries depicted in FIG. 1 is briefly discussed next to further illustrate the nature and purpose of treatment-response database 100.

Identification information 105 includes a label or mechanism to connect together different information about the same subject. Example identification information 105 includes name, address, social security number, driver license number and the like. Prior treatment history 110 preferably includes enough information to enable a determination to be made as to whether the subject is adequately therapeutic entity-free. This is significant not only from the perspective of avoiding harmful cross-reactions between different therapeutic entities, but also to increase the accuracy of the evaluations made possible by the invention. For instance, the outcome database of CNS Response includes only those subjects who have been drug-free for at least seven half-lives of previously administered therapeutic entities. Such subjects provide pre-treatment neurophysiologic information as opposed to an initial neurophysiologic information. In some applications, in view of long-term effects of some therapeutic entities, it is desirable to make predictions of response to a treatment made with the aid of pre-treatment neurophysiologic information. In addition, using initial neurophysiologic information in alternative embodiments of the invention will further take into account prior therapeutic entity history.

Initial or pre-treatment neurophysiologic information 115 discussed above is one of the core components of the treatment-response database 100. Predictions of treatment outcome are made based on matching such information. Typically, EEG based neurophysiologic information includes univariate measures of brain activity discussed previously. These may be in the form of a set of composite traces or in the form of Z-transformed values reflecting relative distribution with respect to a reference distribution.

Another core component is magnitude-outcome of a treatment 120 reflecting a clinical judgment of the consequences of a course of treatment. For instance, clinical global index (CGI) assigns a score in the interval $[-1, 3]$ to a treatment. A value of $-1$ indicates worsening of the condition, 0 indicates no change, 1 indicates a minimal improvement, 2 indicates a moderate improvement while 3 indicates absence of the original symptoms, a recovery, or total remission. Many alternative schemes that represent changes in several factors into a single or few scores can be advantageously employed to provide a common measure of the efficacy of different treatments.

Active-treatment neurophysiologic information 130 is not necessarily required for predicting a response to a treatment since the response to a treatment 125 is typically included as magnitude-outcome. However, it is a convenient alternative to magnitude-outcome 125 or a concurrent indicator of response to treatment. Active-treatment neurophysiologic information 130 provides another measure of a response to treatment, for instance, after comparison to initial or pre-treatment neurophysiologic information 115. In some embodiments of the invention, active-treatment neurophysiologic information 130 may suffice to generate a measure similar to magnitude-outcome 125, reflecting normalization of the EEG signals following treatment. However, the normalization is of some selected univariate variables rather of all univariate variables.

Membership in clusters 135 is another feature of the treatment-response database 100 that is advantageously included rather than rederived each time treatment-response database 100 is used. In an aspect of the invention, pre-treatment or initial neurophysiologic information 115 is clustered by various techniques so that each cluster corresponds to a selected one or set of outcomes and one or more selected treatments. Additionally, measures are taken to reduce the false negatives in each cluster while ensuring maximal coverage of pretreatment or initial neurophysiologic information 115 of subjects having similar outcomes of treatments. Storing the results of a clustering analysis saves effort since a fresh analysis is required only upon addition of significant number of subjects to the treatment-response database 100.

Notes on different therapeutic entities and their known or suspected interactions 140 is yet another useful but optional entry. Such information allows the treatment recommendations generated by the treatment-response database 100 to be checked to rule out deleterious interactions at the outset rather than have a physician or pharmacy flag such potential mishaps, or worse incur the risk of cross-reaction between therapeutic entities. Such information may be in a separate set of records or only of records pertinent to the treatments received or to be received by a particular subject or group of subjects.

Finally, advantageously, in a manner similar to membership in clusters 130, treatment-response database 100 includes rules, indicative variables or results of applying the rules 145 to provide a ready reference to significant results of a cluster analysis. While not required for practicing the invention, such information enables rapid database searches and evaluation of treatment recommendations.

Figure 13:
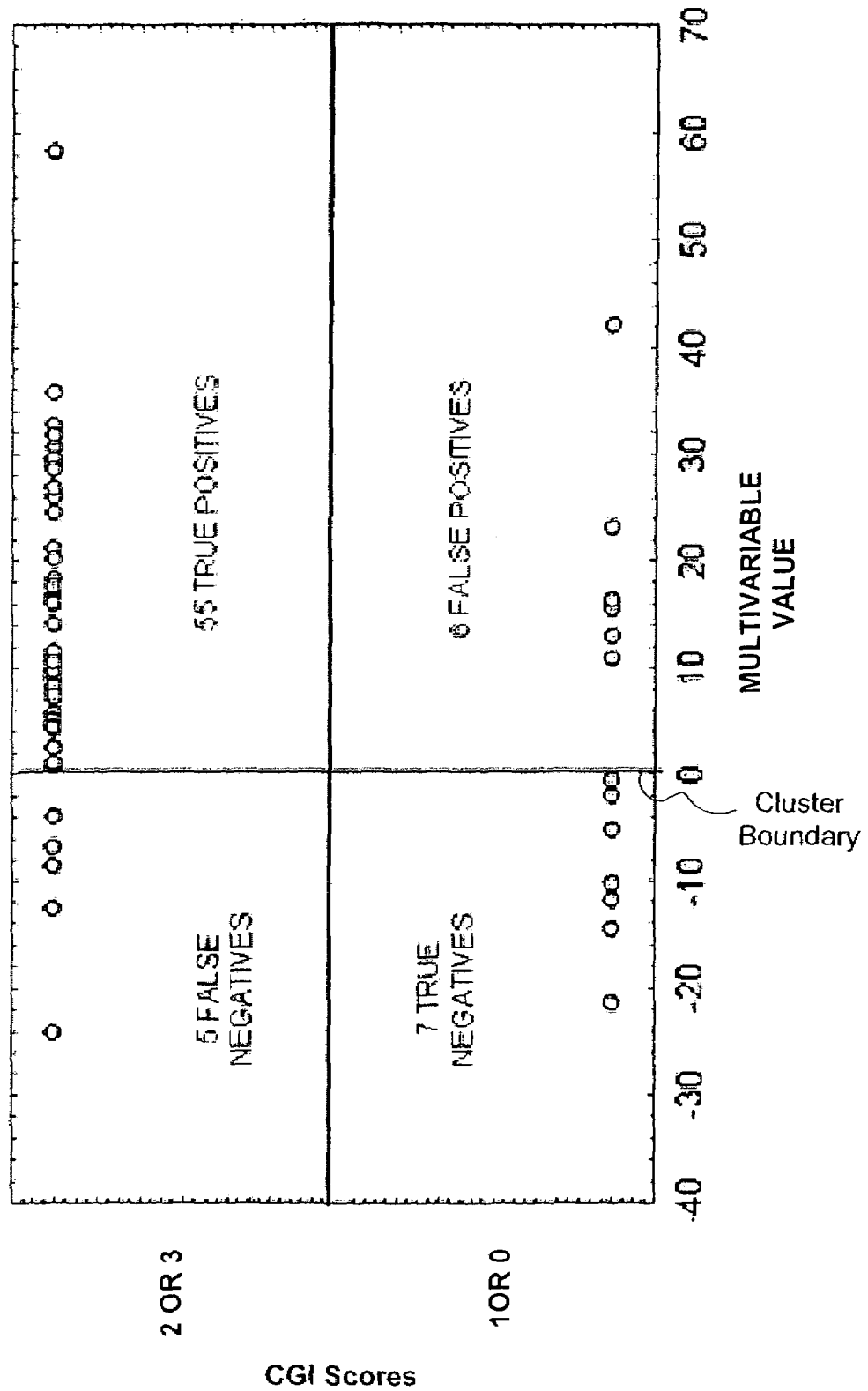
FIG. 13 illustrates a multivariable and clustering of data in its context.

FIG. 13 illustrates a cluster boundary along with a two dimensional representation of a rule. FIG. 13 also illustrates the utility of the clustering strategy in generating treatment strategies prospectively. A multivariable is plotted against the CGI outcome for eighty-three (83) patients treated with D-amphetamine. The fifty-five (55) patients in a cluster of sixty-one (61) patients, as described below, were assigned various DSM diagnosis including Adjustment Disorder With Anxiety; Adjustment Disorder With Disturbance of Conduct; Anorexia Nervosa; Attention-Deficit/Hyperactivity Disorder Combined Type; Attention-Deficit/Hyperactivity Disorder Predominantly Inattentive Type; Depressive Disorder NOS; Dysthymic Disorder; Major Depressive Disorder Recurrent; Major Depressive Disorder Single Episode; Obsessive-Compulsive Disorder; Oppositional Defiant Disorder; and Trichotillomania. Subsequent analysis of the EEG data revealed that sixty-one (61) of the eighty-three (83) patients exhibited values for a multivariable that defined a cluster with a boundary at '0'. Of these sixty-one (61) patients, fifty-five (55) exhibited a positive response while six (6) were false positives. On the other hand there were five (5) false negatives and seven (7) of the eighty-three (83) patients were correctly distinguished by the multivariable as not belonging to the cluster.

Figure 2:
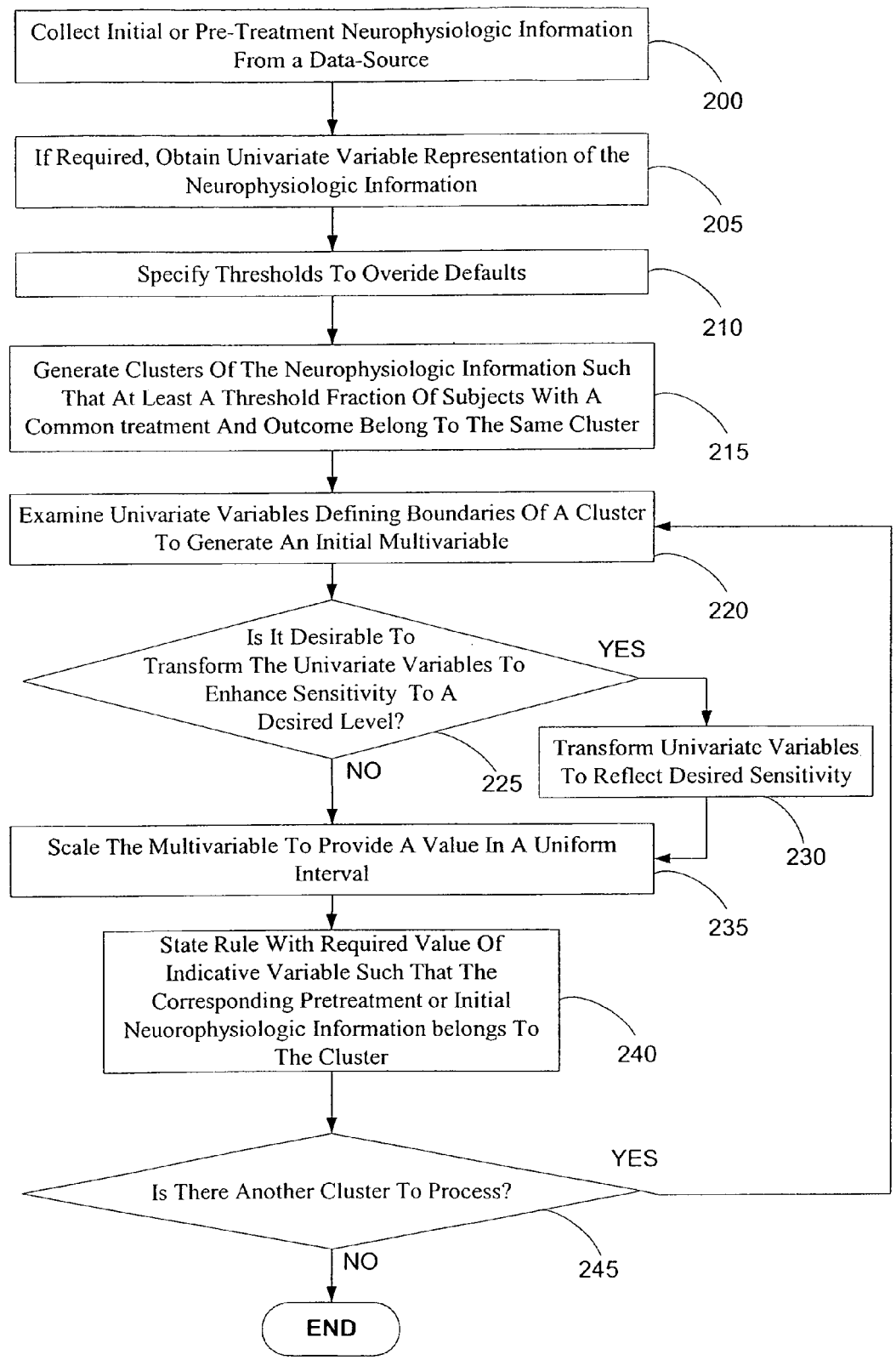
FIG. 2 illustrates an exemplary method for using a treatment-response database.

FIG. 2 illustrates an illustrative exemplary method for using a treatment-response database in accordance with the invention. During step 200 neurophysiologic information is collected from a data-source. The data-source could be a patient being evaluated or stored/transmitted data. Although, such data is likely to be EEG/QEEG data due to its ready availability in a suitable form, this is not a requirement for practicing the invention. Next, during step 205, the neurophysiologic information is represented as univariate variables. As is apparent, this is a convenient choice rather than a necessary condition since any other representation reflects merely a different choice of resolution and coordinate transformation.

In the event a cluster is required to satisfy thresholds different from those either presumed or provided as default for both including true positives and excluding false positives, such thresholds are specified during step 210. A convenient threshold requires that at least eighty percent of pre-treatment neurophysiologic information of subjects subsequently displaying a specified outcome to a treatment should be included in a cluster.

During step 215, one or more clusters are generated to form aggregates of pre-treatment neurophysiologic information. In alternative embodiments of the invention initial neurophysiologic information is clustered. The clusters are generated with an input of either an educated guess at the number of clusters or data in the multidimensional space defined by the univariate variables is clustered with no such a priori assumptions.

Notably, many therapeutic entities correspond to adjacent clusters within a common region of the multidimensional space. Moreover, different related therapeutic entities can then be thought of as defining a class of therapeutic entities or treatments that are suitable for similar initial or pre-treatment neurophysiologic information.

Interestingly, many therapeutic entities that would otherwise not be considered to be similar, and that are typically prescribed for different traditional diagnosis actually cluster together while therapeutic entities commonly prescribed for the same traditional diagnosis do not cluster together. Thus, the observed heterogeneity encountered in treating traditional diagnosis is also reflected in the clustering. Therefore, the clusters enable prediction of the response of a subject based on whether the pre-treatment neurophysiologic information falls within a cluster, and thus reducing trial-and-error strategies presently forced upon physicians with its (now avoidable) risks. Similar results are made possible in an exemplary embodiment of the invention with the use of suitable initial neurophysiologic information.

During step 220, the boundary defining one of the clusters is examined to identify univariate variables of interest. This process can be illustrated by analogy to the familiar three-dimensional space with embedded therein a plurality of two-dimensional planes, one dimensional lines and points lacking dimensions. For instance, in three-dimensional space, $y=0$ specifies a plane including the origin, the x-axis and the z-axis in the familiar notation. In this example 'y' is a variable of interest. Similarly, univariate variables of interest are identified. If there are several univariate variables then it is convenient to represent them in an indicative variable, e.g., a single multivariable. This is easily done with Z-transformed univariate variables by, for instance, merely adding them together or computing a function having the different univariate variables as its arguments. Some examples of indicative variables or multivariables deduced in this manner are presented in TABLE 1 (below) while TABLE 2 presents the corresponding customary electrode positions for EEG/QEEG based neurophysiologic information. Alternative electrode placements and modes of data collection in other embodiments of the invention are treated in an analogous manner. The underlying univariate variables are further modified in actual usage to adjust for sensitivity and ease of use as described next.

For instance, if the number of univariate variables is large, it is possible that the combined multivariable is not sensitive to changes that include or exclude a small number of subjects from the cluster. This addresses possible concerns stemming from the intended prospective use of the cluster to provide superior treatment. Moreover, the cluster is identified using retrospective data (and data as it is collected) that is susceptible to modification by addition of new data. However, alternative choices of multivariables can just as easily address a perceived need for greater certainty.

Accordingly, the multivariable combination of the univariate variables need not be a simple sum and instead is chosen to be a function exhibiting the requisite sensitivity. The detailed form of the function is advantageously determined empirically although some simple forms can be arrived at analytically. TABLE 3 shows some useful illustrative transformations that should not be interpreted to be a limitation on the scope of the invention.

Accordingly, during step 225 if a decision is made to transform the univariate variables, then control flows to step 230, during which a transformation, for instance one of the transformations presented in TABLE 3, is carried out. Then control moves to step 235. Alternatively, if the indicative variable has one univariate variable then control flows to step 235 from step 225. The multivariables are presented in TABLE 1 while TABLE 3 lists some of the functions that have been actually used. These non-exhaustive lists are primarily illustrative of the invention in the context of the described embodiment.

The variables in TABLE 1 are represented by four letter abbreviations. The first two or three letters of the abbreviations are primary designators. The primary designators RB, RM, CA, CE, FM, AA, and AE indicate what type of QEEG measurement is referenced. For example, the primary designator "RM" represents relative monopolar power. "RB" is relative bipolar power. "CA" is intrahemispheric coherence. "CEB" represents interhemispheric bipolar coherence. "FM" represents monopolar frequency. "AA" represents intrahemispheric asymmetry. And, "AE" represents interhemispheric asymmetry.

The one or last two letters of the multivariable abbreviations are secondary designators. The secondary designators indicate the groups of electrodes and frequency bands from which the measurements are drawn. Measurements are drawn from electrodes in the anterior or ("A"), posterior ("P") regions of the scalp, the left ("L") or right ("R") sides of the scalp. Measurements are made in the delta ("D"), theta ("T"), alpha ("A"), or beta ("B") frequency bands.

According to TABLE 1, "RMAD" (relative power monopolar anterior delta) is the relative monopolar power in the delta frequency measured at the electrodes located on the front half of the scalp. Similarly, "RBDL" is the relative bipolar power measured by the electrodes in the left half of the scalp for the delta frequency band. "CABL" is intrahemispheric coherence measured from the electrodes in the left region of the scalp in the beta frequency band. "CADR" is the intrahemispheric coherence measured at the electrodes in the right region of the scalp for the delta frequency band. "AED" is monopolar asymmetry measured interhemispherically in the delta frequency band.

TABLE 1

| NAME | DESCRIPTION | NAME | DESCRIPTION |
|------|-------------|------|-------------|
| RMAD | Relative power Monopolar Anterior Delta | CABL | Beta - Left |
| RMPD | Posterior Delta | CABR | Beta - Right |
| RMAT | Anterior Theta | FMAD | Frequency Monopolar Anterior Delta |
| RMPT | Posterior Theta | FMPD | Posterior Delta |
| RMAA | Anterior Alpha | FMAT | Anterior Theta |
| RMPA | Posterior Alpha | FMPT | Posterior Theta |
| RMAB | Anterior Beta | FMAA | Anterior Alpha |
| RMPB | Posterior Beta | FMPA | Posterior Alpha |
| CEAD | Coherence interhemispheric Anterior Delta | FMAB | Anterior Beta |
| CEPD | Posterior Delta | FMPB | Posterior Beta |
| CEAT | Anterior Theta | AADL | Asymmetry Intrahemispheric Delta - Left |
| CEPT | Posterior Theta | AADR | Delta - Right |
| CEAA | Anterior Alpha | AATL | Theta - Left |
| CEPA | Posterior Alpha | AATR | Theta - Right |
| CEAB | Anterior Beta | AAAL | Alpha - Left |
| CEPB | Posterior Beta | AAAR | Alpha - Right |
| AEMD | Asymmetry interhemispheric Monopolar Delta | AABL | Beta - Left |
| AEMT | Theta | AABR | Beta - Right |
| AEMA | Alpha | CEBD | Coherence interhemispheric Bipolar Delta |
| AEMB | Beta | CEBT | Theta |
| AEBD | Asymmetry interhemispheric Bipolar Delta | CEBA | Alpha |
| AEBT | Theta | CEBB | Beta |
| AEBA | Alpha | RBDL | Relative power Bipolar Delta Left |
| AEBB | Beta | RBDR | Delta - Right |
| CADL | Coherence intrahemispheric Delta - Left | RBTL | Theta - Left |
| CADR | Delta - Right | RBTR | Theta - Right |
| CATL | Theta - Left | RBAL | Alpha - Left |
| CATR | Theta - Right | RBAR | Alpha - Right |
| CAAL | Alpha - Left | RBBL | Beta - Left |
| CAAR | Alpha - Right | RBBR | Beta - Right |

TABLE 2

| INDICATIVE VARIABLE | ELECTRODES | | | | | | | | | | |
|---|---|---|---|---|---|---|---|---|---|---|---|
| | 1 | 2 | 3 | 4 | 5 | 6 | 7 | 8 | 9 | 10 | 11 |
| RMAD | Fp1 | Fpz | Fp2 | F3 | FZ | F4 | F7 | F8 | C3 | Cz | C4 |
| RMPD | T3 | T4 | T5 | T6 | P3 | Pz | P4 | O1 | Oz | O2 | |
| RMAT | Fp1 | Fpz | Fp2 | F3 | FZ | F4 | F7 | F8 | C3 | Cz | C4 |
| RMPT | T3 | T4 | T5 | T6 | P3 | Pz | P4 | O1 | Oz | O2 | |
| RMAA | Fp1 | Fpz | Fp2 | F3 | FZ | F4 | F7 | F8 | C3 | Cz | C4 |
| RMPA | T3 | T4 | T5 | T6 | P3 | Pz | P4 | O1 | Oz | O2 | |
| RMAB | Fp1 | Fpz | Fp2 | F3 | FZ | F4 | F7 | F8 | C3 | Cz | C4 |
| RMPB | T3 | T4 | T5 | T6 | P3 | Pz | P4 | O1 | Oz | O2 | |
| CEAD | FP1/ FP2 | F3/ F4 | F7/ F8 | C3/ C4 | | | | | | | |
| CEPD | T3/ T4 | T5/ T6 | P3/ P4 | O1/ O2 | | | | | | | |
| CEAT | FP1/ FP2 | F3/ F4 | F7/ F8 | C3/ C4 | | | | | | | |
| CEPT | T3/ T4 | T5/ T6 | P3/ P4 | O1/ O2 | | | | | | | |

TABLE 2-continued

| INDICATIVE VARIABLE | ELECTRODES | | | | | | | | | | |
|---|---|---|---|---|---|---|---|---|---|---|---|
| | 1 | 2 | 3 | 4 | 5 | 6 | 7 | 8 | 9 | 10 | 11 |
| CEAA | FP1/FP2 | F3/F4 | F7/F8 | C3/C4 | | | | | | | |
| CEPA | T3/T4 | T5/T6 | P3/P4 | O1/O2 | | | | | | | |
| CEAB | FP1/FP2 | F3/F4 | F7/F8 | C3/C4 | | | | | | | |
| CEPB | T3/T4 | T5/T6 | P3/P4 | O1/O2 | | | | | | | |
| FMAD | Fp1 | Fpz | Fp2 | F3 | FZ | F4 | F7 | F8 | C3 | Cz | C4 |
| FMPD | T3 | T4 | T5 | T6 | P3 | Pz | P4 | O1 | Oz | O2 | |
| FMAT | Fp1 | Fpz | Fp2 | F3 | FZ | F4 | F7 | F8 | C3 | Cz | C4 |
| FMPT | T3 | T4 | T5 | T6 | P3 | Pz | P4 | O1 | Oz | O2 | |
| FMAA | Fp1 | Fpz | Fp2 | P3 | FZ | F4 | F7 | F8 | C3 | Cz | C4 |
| FMPA | T3 | T4 | T5 | T6 | P3 | Pz | P4 | O1 | Oz | O2 | |
| FMAB | Fp1 | Fpz | Fp2 | F3 | FZ | F4 | F7 | F8 | C3 | Cz | C4 |
| FMPB | T3 | T4 | T5 | T6 | P3 | Pz | P4 | O1 | Oz | O2 | |
| AEMD | FP1/FP2 | F3/F4 | F7/F8 | C3/C4 | T3/T4 | T5/T6 | P3/P4 | O1/O2 | | | |
| AEMT | FP1/FP2 | F3/F4 | F7/F8 | C3/C4 | T3/T4 | T5/T6 | P3/P4 | O1/O2 | | | |
| AEMA | FP1/FP2 | F3/F4 | F7/F8 | C3/C4 | T3/T4 | T5/T6 | P3/P4 | O1/O2 | | | |
| AEMB | FP1/FP2 | F3/F4 | F7/F8 | C3/C4 | T3/T4 | T5/T6 | P3/P4 | O1/O2 | | | |
| AADL | F3/T5 | F7/O1 | F3/O1 | F7/O1 | | | | | | | |
| AADR | F4/T6 | F8/T6 | F4/O2 | F8/O2 | | | | | | | |
| AATL | F3/T5 | F7/T5 | F3/O1 | F7/O1 | | | | | | | |
| AATR | F4/T6 | F8/T6 | F4/O2 | F8/O2 | | | | | | | |
| AAAL | F3/T5 | F7/T5 | F3/O1 | F7/O1 | | | | | | | |
| AAAR | F4/T6 | F8/T6 | F4/O2 | F8/O2 | | | | | | | |
| AABL | F3/T5 | F7/T5 | F3/O1 | F7/O1 | | | | | | | |
| AABR | F4/T6 | F8/T6 | F4/O2 | F8/O2 | | | | | | | |
| CADL | Fp1/F3 | T3/T5 | C3/P3 | F3/O1 | | | | | | | |
| CADR | Fp2/F4 | T4/T6 | C4/P4 | F4/O2 | | | | | | | |
| CATL | Fp1/F3 | T3/T5 | C3/P3 | F3/O1 | | | | | | | |
| CATR | Fp2/F4 | T4/T6 | C4/P4 | F4/O2 | | | | | | | |
| CAAL | Fp1/F3 | T3/T5 | C3/P3 | F3/O1 | | | | | | | |
| CAAR | Fp2/F4 | T4/T6 | C4/P4 | F4/O2 | | | | | | | |
| CABL | Fp1/F3 | T3/T5 | C3/P3 | F3/O1 | | | | | | | |
| CABR | Fp2/F4 | T4/T6 | C4/P4 | F4/O2 | | | | | | | |
| RBDL | C3/Cz | T3/T5 | P3/O1 | F7/T3 | | | | | | | |
| RBDR | C4/Cz | T4/T6 | P4/O2 | F8/T4 | | | | | | | |
| RBTL | C3/Cz | T3/T5 | P3/O1 | F7/T3 | | | | | | | |
| RBTR | C4/Cz | T4/T6 | P4/O2 | F8/T4 | | | | | | | |
| RBAL | C3/Cz | T3/T5 | P3/O1 | F7/T3 | | | | | | | |
| RBAR | C4/Cz | T4/T6 | P4/O2 | F8/T4 | | | | | | | |
| RBBL | C3/Cz | T3/T5 | P3/O1 | F7/T3 | | | | | | | |
| RBBR | C4/Cz | T4/T6 | P4/O2 | F8/T4 | | | | | | | |
| AEBD | C3Cz/C4Cz | T3T5/T4T6 | P3O1/P4O2 | F7T3/F8T4 | | | | | | | |
| AEBT | C3Cz/C4Cz | T3T5/T4T6 | P3O1/P4O2 | F7T3/F8T4 | | | | | | | |
| AEBA | C3Cz/C4Cz | T3T5/T4T6 | P3O1/P4O2 | F7T3/F8T4 | | | | | | | |
| AEBB | C3Cz/C4Cz | T3T5/T4T6 | P3O1/P4O2 | F7T3/F8T4 | | | | | | | |
| CEBD | C3Cz/C4Cz | T3T5/T4T6 | P3O1/P4O2 | F7T3/F8T4 | | | | | | | |
| CEBT | C3Cz/C4Cz | T3T5/T4T6 | P3O1/P4O2 | F7T3/F8T4 | | | | | | | |
| CEBA | C3Cz/C4Cz | T3T5/T4T6 | P3O1/P4O2 | F7T3/F8T4 | | | | | | | |
| CEBB | C3Cz/C4Cz | T3T5/T4T6 | P3O1/P4O2 | F7T3/F8T4 | | | | | | | |

TABLE 3

| Name | Description | Transform & Weighting Function |
|------|-------------|-------------------------------|
| RMAX[a] | Relative power Monopolar Anterior | $12/10 \sum_{10} \frac{1}{} Electrode_1 \ldots Electrode_{10}$ |
| RMPX[a] | Relative power Monopolar Posterior | $12/11 \sum_{11} \frac{1}{} Electrode_1 \ldots Electrode_{11}$ |
| FMAX[a] | Frequency Monopolar Anterior | $12/10 \sum_{10} \frac{1}{} Electrode_1 \ldots Electrode_{10}$ |
| FMPX[a] | Frequency Monopolar Posterior | $12/11 \sum_{11} \frac{1}{} Electrode_1 \ldots Electrode_{11}$ |
| CEAX[a] | Coherence interhemispheric Anterior | $\sqrt[3.6]{\sum_4^1 Electrode_1^3 \ldots Electrode_4^3}$ |
| AEMX[a] | Asymmetry interhemispheric Monopolar | $\sqrt[3.6]{\sum_8^1 Electrode_1^3 \ldots Electrode_8^3}$ |
| AEBX[a] | Asymmetry interhemispheric Bipolar | $\sqrt[3.6]{\sum_4^1 Electrode_1^3 \ldots Electrode_4^3}$ |
| AAYX[a] | Asymmetry intrahemispheric | $\sqrt[3.6]{\sum_4^1 Electrode_1^3 \ldots Electrode_4^3}$ |
| CEBX[a] | Coherence interhemispheric | $\sqrt[3.6]{\sum_4^1 Electrode_1^3 \ldots Electrode_4^3}$ |
| RBYX[a] | Relative power Bipolar | $\sqrt[3.6]{\sum_4^1 Electrode_1^3 \ldots Electrode_4^3}$ |
| CAYX[a] | Coherence intrahemispheric | $\sqrt[3.6]{\sum_4^1 Electrode_1^3 \ldots Electrode_4^3}$ |

[a]X = D, T, A, B; [a]X = D, T, A, B; Y = L, R

During step 235 the multivariable is scaled to provide a uniform scale of reference for all multivariables. For instance, in the described embodiment to provide a value in the interval [−40, 40] such that four standard deviations are spanned on each side of the mean. Alternative scaling strategies, e.g., using the interval [−10, 10] or variant number of standard deviations are employed in alternative exemplary embodiments of the invention. Moreover, the transformation and scaling operations can be carried out in a single step if desired as is illustrated in TABLE 4.

TABLE 4 illustrates the transformation depicted in TABLE 3 for the multivariable CEAD (represented as entry CEAX). TABLE 4 includes both the transformation and the subsequent scaling. The weighting function depicts the transformation while the rows below describe a possible scaling operation. For instance, the components are paired by addition, squared separately and then added to get a positive whole number. This number is made negative if the sum of the terms generated by the transformation is negative, else it is made positive. Typically, a number between −40 and 40 is obtained with truncation of values exceeding these limits. Since the likelihood of multivariable CEAD having a value outside the range is rather small the truncation operation is rarely invoked.

TABLE 4

|  | Component 1 | Component 2 | Component 3 | Component 4 |
|---|---|---|---|---|
| Electrode pair | Fp1/Fp2 | F3/F4 | F7/F8 | C3/C4 |
| Univariate Z Score | −0.982 | −1.036 | −1.230 | −0.249 |
| Weighting Function, $\sqrt[3.6]{\sum_{i=1}^4 Electrode_i^3}$ | 0.985 | −1.030 | −1.188 | −0.314 |
| Fp1/Fp2 + F3/F4 |  | −2.015 |  |  |
| F7/F8 + C3/C4 |  |  |  | −1.502 |
| Square Collected Terms |  |  | 4.060 | 2.256 |
| Sum of Squares | 6.316 |  |  |  |
| Sign Correction[a] | −1 |  |  |  |
| CEAD | 6 |  |  |  |

TABLE 5, below, illustrates an alternative scheme:

TABLE 5

|  | Component 1 | Component 2 | Component 3 | Component 4 |
|---|---|---|---|---|
| Electrode pair | Fp1/Fp2 | F3/F4 | F7/F8 | C3/C4 |
| Univariate Z | −0.982 | −1.036 | −1.230 | −0.249 |
| Weighting Function, $C^3$ Collect Terms | −0.947 | −1.112 | −1.861 | −0.015 |
| Fp1/Fp2 + F3/F4 |  | −2.059 |  |  |
| F7/F8 + C3/C4 |  |  |  | −1.876 |

TABLE 5-continued

|  | Component 1 | Component 2 | Component 3 | Component 4 |
|---|---|---|---|---|
| Square Collected |  | 4.239 |  | 3.520 |
| Sum of Squares | 7.760 |  |  |  |
| Sign Correction[a] | −1 |  |  |  |
| CEAD | −8 |  |  |  |

[a]negative if sum of terms is negative

TABLE 5 indicates that the CEAD multivariable is calculated from readings collected at four electrode pairs, designated by their names under the International 10/20 system. The electrode pairs are referred to as components 1-4. Z scores are calculated for each electrode pair. The Z scores are transformed by a weighting function, $C^3$, as indicated in TABLE 3. The process of transformation makes it possible to mathematically combine the Z scores. The square is calculated for the sum of each of the components of CEAD. The values are then mapped into a "clinical decision" interval ranging from −40 to +40. This mapping creates an integer scale of uniform change for each of the multivariable descriptors. Thus, the weighted Z scores calculated for the electrode pairs within the same brain hemisphere were summed (Fp1/Fp2+F3/F4=−2.059; F7/F8+C3/C4=−1.876), squared, ($-2.059^2=4.239$; $-1.876^2=3.520$), and added together (4.239+3.520=7.760). The sign of the final product was corrected and rounded off to the nearest whole number (−7.760→−8).

As is readily evident, many alternative schemes, such as squaring all terms following transformation and adding them, are possible and are intended to be included within the scope of the invention.

Following scaling, control passes to step 240 although the ordering of the steps is clearly arbitrary and does not imply a limitation on the scope of the invention. During step 240 a rule is generated, typically describing the boundary of the cluster, so that membership in a cluster is tested easily by applying a set of rules to a corresponding set of multivariables/indicative variables. This aspect of the invention enables analysis without requiring a fresh clustering step or access to an overloaded database. Moreover, handheld devices, portable devices and various grades of software providing evaluation of therapeutic entities, treatments or design of therapeutic entity testing studies are made possible with the identification of such rules. If there is another cluster to process then control passes to step 220 from step 245. Otherwise, the method terminates.

Additionally, the invention enables using clusters with 'fuzzy' boundaries. Following the generation of rules in step 240 of FIG. 2, if a substantial fraction of the rules defining a cluster associated with a treatment are satisfied by a subject's pre-treatment neurophysiologic information, then it is likely that that the pre-treatment neurophysiologic information might belong to the cluster. Thus, a prediction is possible for the effect of the treatment in accordance with the cluster although not every rule defining the boundary of the cluster is satisfied. Some example rules are provided in TABLE 6, using the multivariables depicted in TABLES 1-3.

TABLE 6

| Index | RULE |
|---|---|
| 1 | EEG ABSOLUTE POWER AVERAGE = >300 microvolts squared |
| 2 | EEG ABSOLUTE POWER AVERAGE = <300 & >40 microvolts sq. |
| 3 | EEG ABSOLUTE POWER AVERAGE = <40 microvolts squared |
| 4 | FRONTAL MIDLINE PROGRESSION INDEX Fpz/Cz (Alpha Band) $\geq 2.5$ |
| 5 | FRONTAL MIDLINE PROGRESSION INDEX Fpz/Cz (Alpha Band) $\leq 2.5$ |
| 6 | FRONTAL MIDLINE PROGRESSION INDEX Fpz/Cz (Alpha Band) $\geq 1$ |
| 7 | FRONTAL MIDLINE PROGRESSION INDEX Fpz/Cz (Alpha Band) $\leq 1$ |
| 8 | RATIO OF FRONTAL/POSTERIOR ALPHA INDICES $\geq 4$ |
| 9 | RATIO OF FRONTAL/POSTERIOR ALPHA INDICES $\leq 4$ |
| 10 | AVERAGE MIDLINE (Fpz$\theta$/Fpz$\beta$ + Fz$\theta$/Fz$\beta$ + Cz$\theta$/Cz$\beta$)/3 THETA/BETA RATIO $\geq 2.5$ |
| 11 | AVERAGE MIDLINE (Fpz$\theta$/Fpz$\beta$ + Fz$\theta$/Fz$\beta$ + Cz$\theta$/Cz$\beta$)/3 THETA/BETA RATIO $\leq 2.5$ & $>1.5$ |
| 12 | AVERAGE MIDLINE (Fpz$\theta$/Fpz$\beta$ + Fz$\theta$/Fz$\beta$ + Cz$\theta$/Cz$\beta$)/3 THETA/BETA RATIO $\leq 1.5$ |
| 13 | RMAD $\geq 10$ OR RMPD $\geq 10$ |
| 14 | RMAD $\leq -10$ OR RMPD $\leq -10$ |
| 15 | RMAT $\geq 10$ OR RMPT $\geq 10$ |
| 16 | RMAT $\leq -10$ OR RMPT $\leq -10$ |
| 17 | RMAA $\geq 10$ OR RMPA $\geq 10$ |
| 18 | RMAA $\leq -10$ OR RMPA $\leq -10$ |
| 19 | RMAB $\geq 10$ OR RMPB $\geq 10$ |
| 20 | RMAB $\leq -10$ OR RMPB $\leq -10$ |
| 21 | CEAD $\geq 10$ OR CEPD $\geq 10$ |
| 22 | CEAD $\leq -10$ OR CEPD $\leq -10$ |
| 23 | CEAT $\geq 10$ OR CEPT $\geq 10$ |
| 24 | CEAT $\leq -10$ OR CEPT $\leq -10$ |
| 25 | CEAA $\geq 10$ OR CEPA $\geq 10$ |
| 26 | CEAA $\leq -10$ OR CEPA $\leq -10$ |
| 27 | CEAB $\geq 10$ OR CEPB $\geq 10$ |
| 28 | CEAB $\leq -10$ OR CEPB $\leq -10$ |
| 29 | FMAD $\geq 10$ OR FMPD $\geq 10$ |
| 30 | FMAD $\leq -10$ OR FMPD $\leq -10$ |

TABLE 6-continued

| Index | RULE |
|---|---|
| 31 | FMAT ≧10 OR FMPT ≧10 |
| 32 | FMAT ≦−10 OR FMPT ≦−10 |
| 33 | FMAA ≧10 OR FMPA ≧10 |
| 34 | FMAA ≦−10 OR FMPA ≦−10 |
| 35 | FMAB ≧10 OR FMPB ≧10 |
| 36 | FMAB ≦−10 OR FMPB ≦−10 |
| 37 | AADL ≧10, OR AADR ≧10 |
| 38 | AADL ≦−10, OR AADR ≦−10 |
| 39 | AATL ≧10, OR AATR ≧10 |
| 40 | AATL ≦−10, OR AATR ≦−10 |
| 41 | AAAL ≧10, OR AAAR ≧10 |
| 42 | AAAL ≦−10, OR AAAR ≦−10 |
| 43 | AABL ≧10, OR AABR ≧10 |
| 44 | AABL ≦−10, OR AABR ≦−10 |
| 45 | AED ≦−10, OR AED ≧10 |
| 46 | AET ≦−10, OR AET ≧10 |
| 47 | AEA ≦−10, OR AEA ≧10 |
| 48 | AEB ≦−10, OR AEB ≧10 |
| 49 | AEBD ≧10 OR AEBD ≦−10 |
| 50 | AEBT ≧10 OR AEBT ≦−10 |
| 51 | AEBA ≧10 OR AEBA ≦−10 |
| 52 | AEBB ≧10 OR AEBB ≦−10 |
| 53 | CADL ≧10, OR CADL ≦−10 |
| 54 | CADR ≧10, OR CADR ≦−10 |
| 55 | CATL ≧10, OR CATL ≦−10 |
| 56 | CATR ≧10, OR CATR ≦−10 |
| 57 | CAAL ≧10, OR CAAL ≦−10 |
| 58 | CAAR ≧10, OR CAAR ≦−10 |
| 59 | CABL ≧10, OR CABL ≦−10 |
| 60 | CABR ≧10, OR CABR ≦−10 |
| 61 | CEBD ≧10, OR CEBD ≦−10 |
| 62 | CEBT ≧10, OR CEBT ≦−10 |
| 63 | CEBA ≧10, OR CEBA ≦−10 |
| 64 | CEBB ≧10, OR CEBB ≦−10 |
| 65 | RBDL ≧10, OR RBDR ≧10 |
| 66 | RBDL ≦−10, OR RBDR ≦−10 |
| 67 | RBAL ≧10, OR RBAR ≧10 |
| 68 | RBAL ≦−10, OR RBAR ≦−10 |
| 69 | RBTL ≧10, OR RBTR ≧10 |
| 70 | RBTL ≦−10, OR RBTR ≦−10 |
| 71 | RBBL ≧10, OR RBBR ≧10 |
| 72 | RBBL ≦−10, OR RBBR ≦−10 |

The example method of the present invention augments established diagnostic and treatment regimens. Therapeutic entity correlation with the outcomes database of the present invention is a useful adjunct to clinical management that helps rule out treatments that are unlikely to be useful. Consequently, patients are spared experimentation and the risk accompanying experimentation due to both human errors and therapeutic entity interactions. For instance, a patient on a first therapeutic entity that is contra-indicated in conjunction with a second therapeutic entity for treating the same DSM-IV diagnosis cannot be switched over to the second therapeutic entity. A suitable intervening time period, typically measured in half-lives of the first therapeutic entity, is required to allow the first therapeutic entity to be eliminated from the system. However, half-life of a therapeutic entity may depend on the age, race, prior history and the like of the subject as well as the form in which the first therapeutic entity was administered. Thus, there is considerable risk of errors such as due to the patient re-ingesting leftover drug or an error in calculating the required intervening time period and the like.

Matching neurophysiologic information from individual subjects to the neurophysiologic data of individuals with known therapeutic entity response outcomes generates a probabilistic treatment recommendation. Notably, this recommendation does not depend on the details of the initial traditional diagnosis. Indeed, a recommendation can be generated based on the existence of a mental disorder that has not yet been diagnosed behaviorally.

Illustratively, when expressed in Z-scores the mean value of the neurophysiologic information approaches zero for asymptomatic individuals. It should be noted that Z-scores approaching zero are not always the only outcome of a successful treatment. For instance, while the Z-scores for a particular set of variables approach zero, the Z-scores for other variables may manifest greater deviations from the reference all the while accompanied by overall clinical improvement. Notably, current therapeutic entities need not be evaluated with an eye on bring about a desired change in the EEG of a subject.

A method for identifying indicative variables is to identify clusters of initial or pre-treatment neurophysiologic information such that each cluster, if possible, corresponds to an outcome of a treatment. The boundaries of these clusters identify univariate variables for forming multivariables and appropriate rules for identifying appropriate clusters. In effect, each cluster corresponds to a group of subjects sharing a common response to a treatment.

The distributions of features of two groups of subjects (where the groups, i.e., clusters, are believed to differ in some way, e.g., to belong to different categories) can be thought of as two clouds of points in a multidimensional space in which each dimension corresponds to a feature such as a univariate variable. There may be no significant differences between the two groups in some dimensions (i.e., in some features) but there may be significant differences in other dimensions. If these clouds of points overlap (i.e., when there is no apparent significant difference between the two groups with respect to some features) it may be possible to define a boundary through the clouds.

In an embodiment of the invention, following a determination that a subject is likely to be afflicted with a behaviorally diagnosed brain disorder results in evaluating whether the subject also manifests neurophysiologic deviations from a reference such as an age-adjusted reference distribution of asymptomatic individuals. Corresponding Z-scores facilitate detection and representation of such deviations. It should be noted that the traditional behaviorally diagnosed brain disorder is of reduced significance in detecting abnormal neurophysiologic information.

Primarily, it is the existence of conditions leading to such a diagnosis rather than the actual diagnosis itself that conveniently triggers a detection of abnormal neurophysiologic information. Thus, the reliance on the elaborate traditional diagnostic system, such as that of DSM-IV, is greatly reduced in arriving at an effective treatment strategy.

The well-known heterogeneity of therapeutic entity response associated with major psychiatric illnesses supports the hypothesis that variable neurophysiology underlies what is apparently the same disorder. Moreover, apparently different disorders share one or more common neurophysiologic determinants susceptible to a common treatment. To this end it is useful to consider initial or pre-treatment neurophysiologic information to deduce the efficacy of potential treatment(s) rather than focus on classifying the behavioral symptoms of disease.

Figure 3:
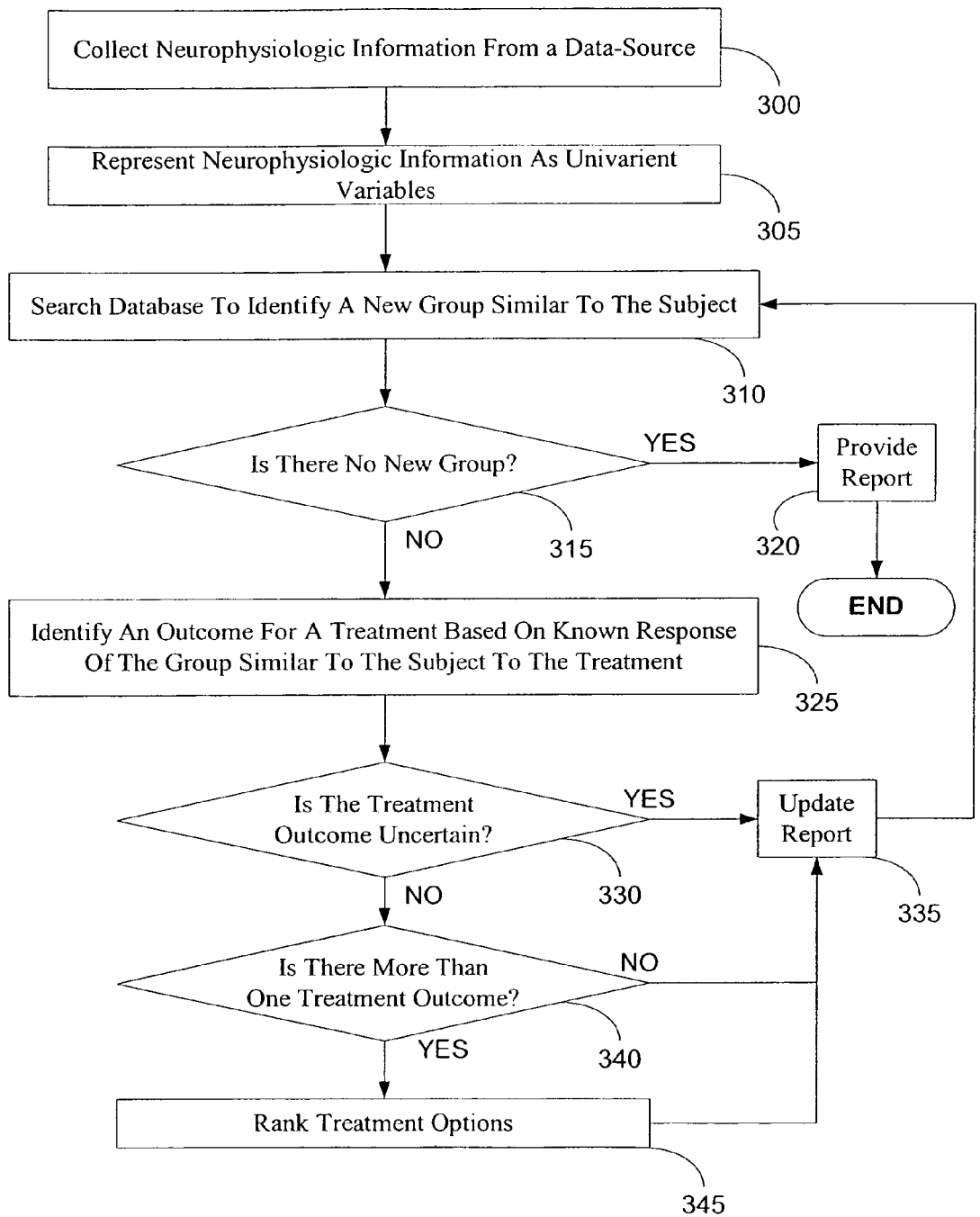
FIG. 3 illustrates the treatment-response database in prospectively evaluating and generating treatments.

FIG. 3 is an illustration of a treatment-response database in use for evaluating and generating treatments. Following collection of neurophysiologic information from a subject during step 300, it is represented in the form of univariate variables during step 305. During step 310 a treatment-response database is searched to identify a new cluster, i.e., new group of subjects having similar neurophysiologic information. If during step 315, if no new group is identified then control flows to step 320 with the outputting of a report listing identified treatments, if any, during step 320. Alternatively, control flows to step 325 from step 315. During step 325 at least one treatment outcome associated with the group is identified. Typically, the clustering step used to form the group includes specification of the outcome, although this is not required for practicing the invention. The treatment outcome is used to rank treatments during step 330 followed by the control flowing to step 335 for updating a report. The control then flows back to step 310 from step 335 to identify a new group associated with the neurophysiologic information collected from the subject during step 300.

Figure 4:
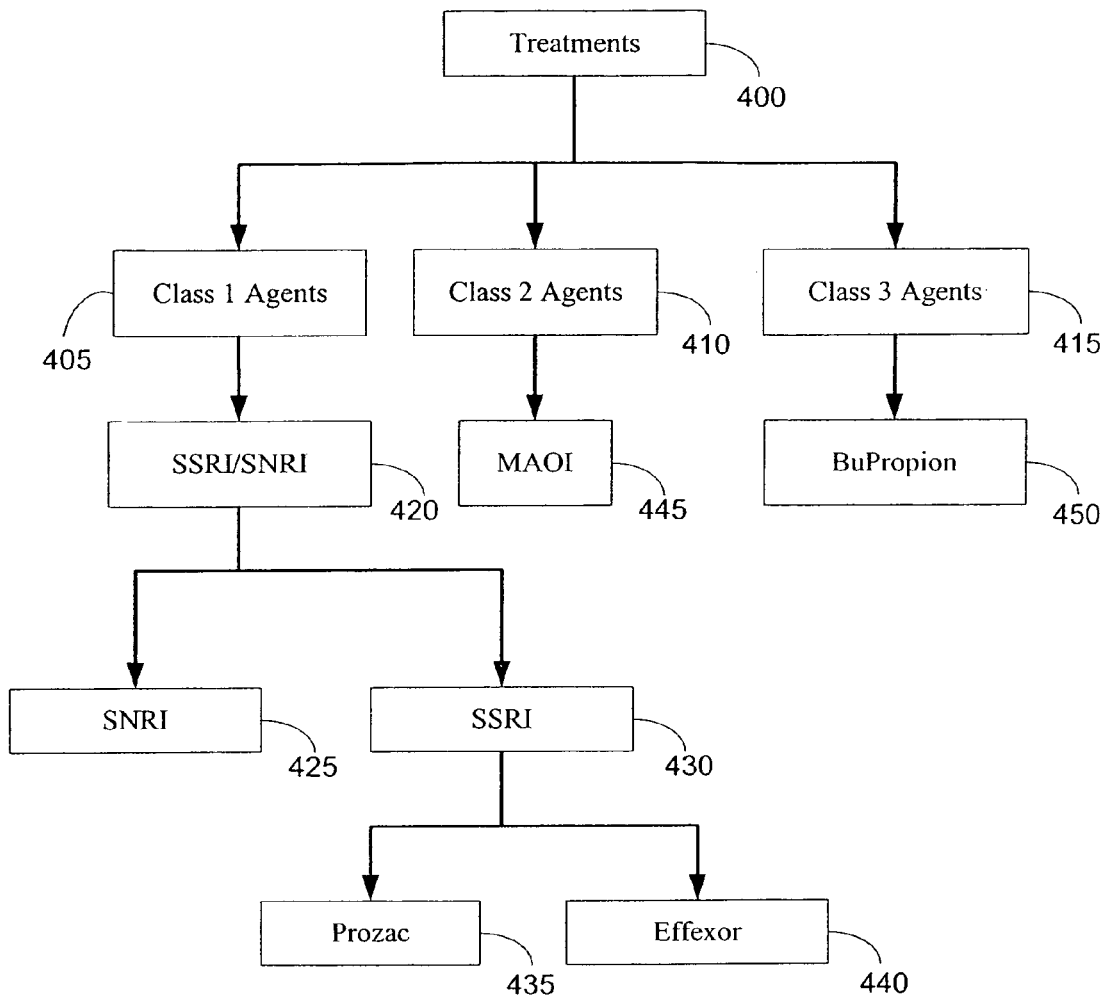
FIG. 4 depicts the relationship between therapeutic entities based on the rules shared by their respective clusters.

FIG. 4 illustrates the relationships between some therapeutic entities. As previously explained, advantageously the rules correspond to a boundary specifying a cluster. Thus, therapeutic entities related by virtue of occupying the same or adjacent regions of the univariate multidimensional space also share common boundaries although this is not an absolute requirement. Moreover, the same traditional condition is often susceptible to various therapeutic entities that are quite different in their clustering properties. The agents listed in FIG. 4 are commonly relied upon to treat depression although they are in at least three different classes of clusters.

Treatments 400, occupy a non-contiguous region of univariate space, having classes defined by regions such as Class 1 agents 405, class 2 agents 410 and class 3 agents 415. Within Class 1 405 is sub-classes SSRI/SNRI 420 further comprising SNRI 425 and SSRI 430. SSRI further include the familiar therapeutic entities PROZAC 435 and EFFEXOR 440. Similarly, Class 2 410 include MAOI 445 and Class 3 includes Bupropion 450.

Examining the Physicians Desk Reference, $55^{th}$ edition (2001), published by Medical Economics Company at Montvale, N.J., for PROZAC 435 reveals that (1) it has a half-life that is as long as 16 days after chronic administration (with as many as 7% of users being even slower metabolizers, i.e., having even longer half-lives for the active ingredient fluoxetine hydrochloride), and (2) it is contraindicated with administration of MAOI 445 requiring an intervening period of at least 14 days after MAOI 445 therapy and five weeks following administration of PROZAC 435. Thus, without additional information if a subject administered PROZAC 435 is non-responsive or has an adverse response to it, then another therapeutic entity such as an agent known to be a MAOI cannot be prescribed for a significant length of time. This requires long-term experimentation while the invention provides a predictive strategy for choosing an effective agent. Similarly, WELLBUTRIN, an agent in the sub-class bupropion 450 is also contraindicated with MAOI 445 agents. Thus, the ability to prospectively distinguish between such agents enables effective care and treatment with lower risks of deleterious effects.

Prescreening is particularly important due to the presence of cross-reactivity, switching a subject to an alternative therapeutic entity often requires waiting for the original therapeutic entity to be eliminated from the subjects' system. This requires the subject to suffer unnecessarily or imposes a schedule for trying various therapeutic entities on the patient in the order of their half-lives. Furthermore, in view of the uncertainties inherent in medicine, the likelihood of error and serious complications also increases without the benefit of prescreening.

Figure 5:
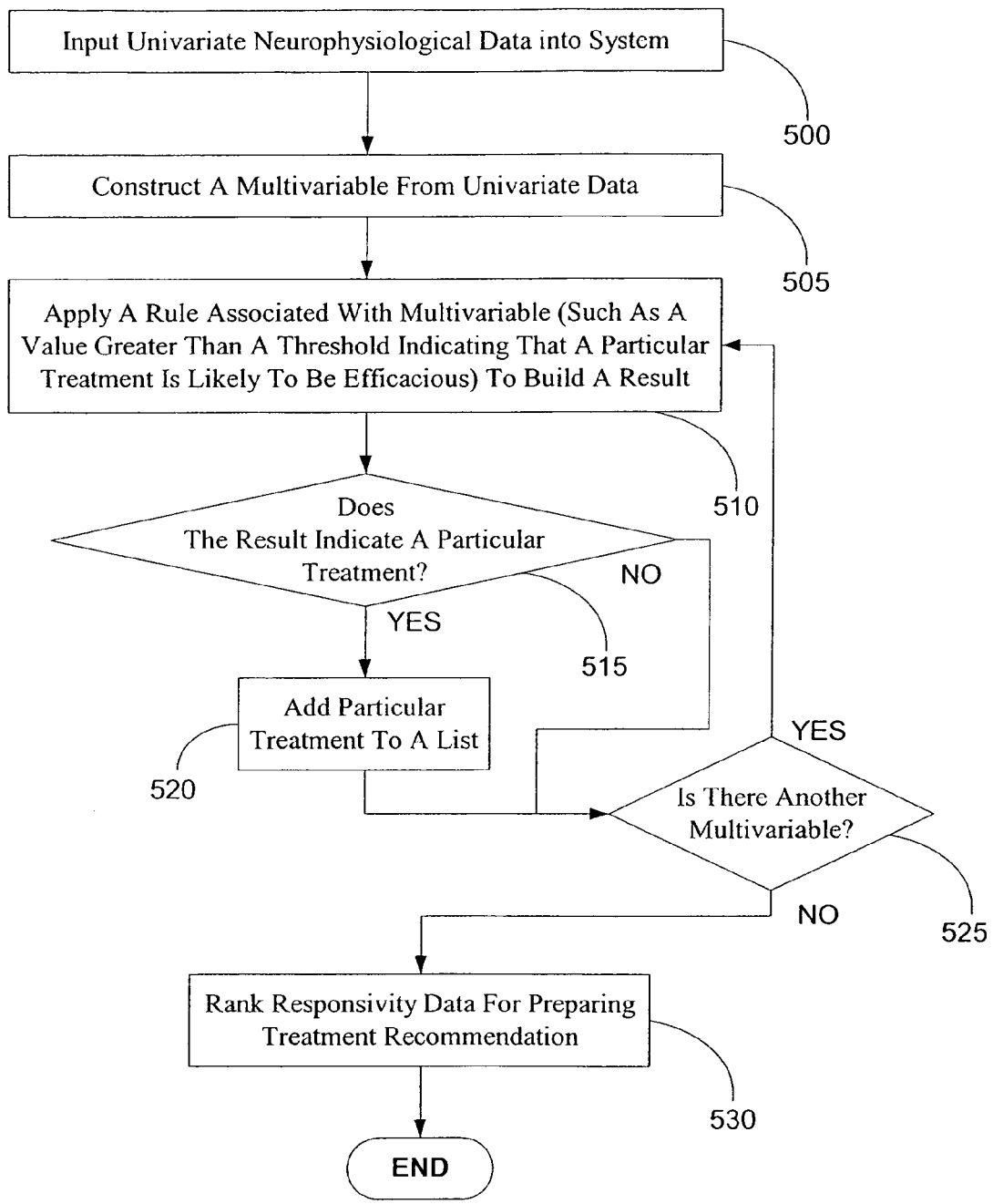
FIG. 5 describes an exemplary method for identifying agents for devising a treatment for a subject.

FIG. 5 is an exemplary method for identifying agents to devise a treatment strategy for a subject's particular neurophysiologic information with the aid of a list of multivariables and their associated rules. Neurophysiologic information is obtained as univariate variables during step 500. Next, a multivariable is constructed from the univariate variables during step 505. During step 510 a rule associated with the multivariable is applied to the value of the multivariable and the cumulative set of consequences of applying the rules included in a result. If the result is sufficient to indicate a treatment during step 515 then control passes to step 520. During step 520 the treatment is added to the list. Otherwise, control passes to step 525 from step 515 for testing for another multivariable. If during step 525 it is determined that there is another multivariable to be tested then control passes to step 505. Otherwise, control passes to step 530 for ranking the identified treatments followed by terminating the method.

Figure 6:
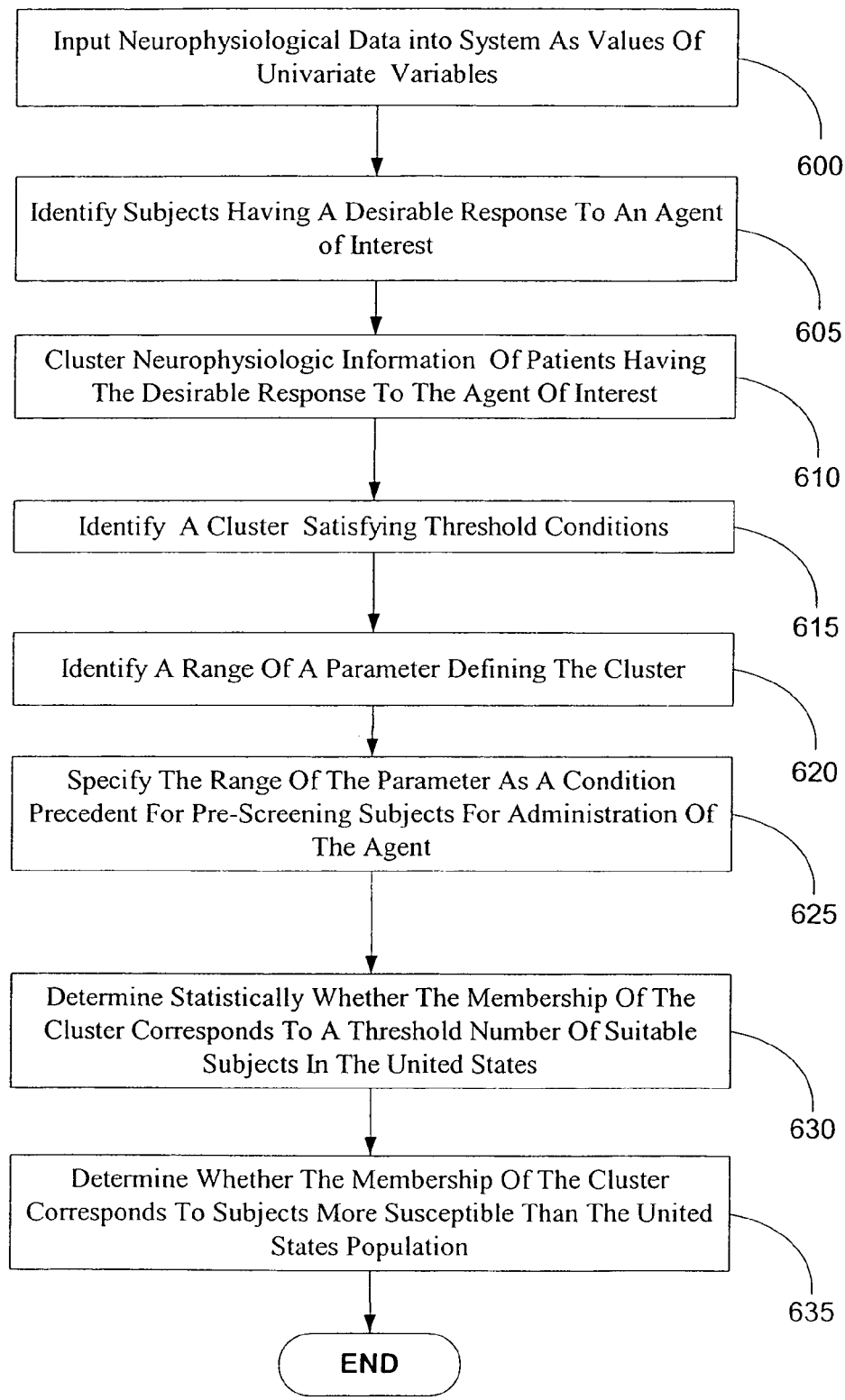
FIG. 6 illustrates an exemplary method for evaluating neurophysiologic information of subjects having a known response to an agent.

FIG. 6 illustrates steps in an exemplary method for utilizing the cluster analysis strategy for evaluating neurophysiologic information of subjects having a known response to an agent. Such data may be obtained either in a planned set of procedures or be collated from various studies for further analysis. During step 600 neurophysiologic information is obtained, during step 605, from subject(s) exhibiting a desirable response to a treatment. Such desirable responses include deleterious responses or clinically significant improvements or even the failure to exhibit a response, i.e., non-responders depending on the context for clustering. Clustering, during step 610, neurophysiologic information of subjects identified during step 605 generates clusters of initial or pretreatment neurophysiologic information although in some embodiments of the invention active-treatment neurophysiologic information may be employed as well. A cluster satisfying suitable boundary conditions is identified during step 615 such that it includes a prescribed threshold of subjects identified during step 605 while, optionally, excluding remaining subjects such that no more than a prescribed fraction of false positives is included. The boundary of the cluster is examined to identify a range of values permissible for either the univariate variables or for the composite multivariate variables during step 620. For new subjects, the identified parameter range serves as a condition precedent for prescreening subjects for administration of the agent during step 625.

In addition to the preceding analysis, during step 630 the relative proportions of subjects identified during step 605 in conjunction with the appropriate sampling frequencies enable determining the expected fraction of subjects relative to the population of the United States (or another reference in alternative jurisdictions) that will exhibit the desirable response used in step 610. Such information is useful not only for marketing purpose, but also provides a measure of the significance of the agent to a particular group of potential subjects. Such information is useful in identifying whether a potential formulation is an orphan drug in accordance with statutory aims in jurisdictions such as United States that encourage bringing such therapeutic entities to market.

During step 635, an optional determination of whether the subjects in the cluster have heightened susceptibility to the treatment is made followed by termination of the method. Such a determination has numerous applications from educating at risk individuals of their susceptibility to worse than expected response to addictive and recreational drugs to planning of public education programs by local, state and national governments and other organizations. Of course, it also provides a predictive window on the expected prevalence of a particular condition (not necessarily deleterious) in the population at large.

Figure 7:
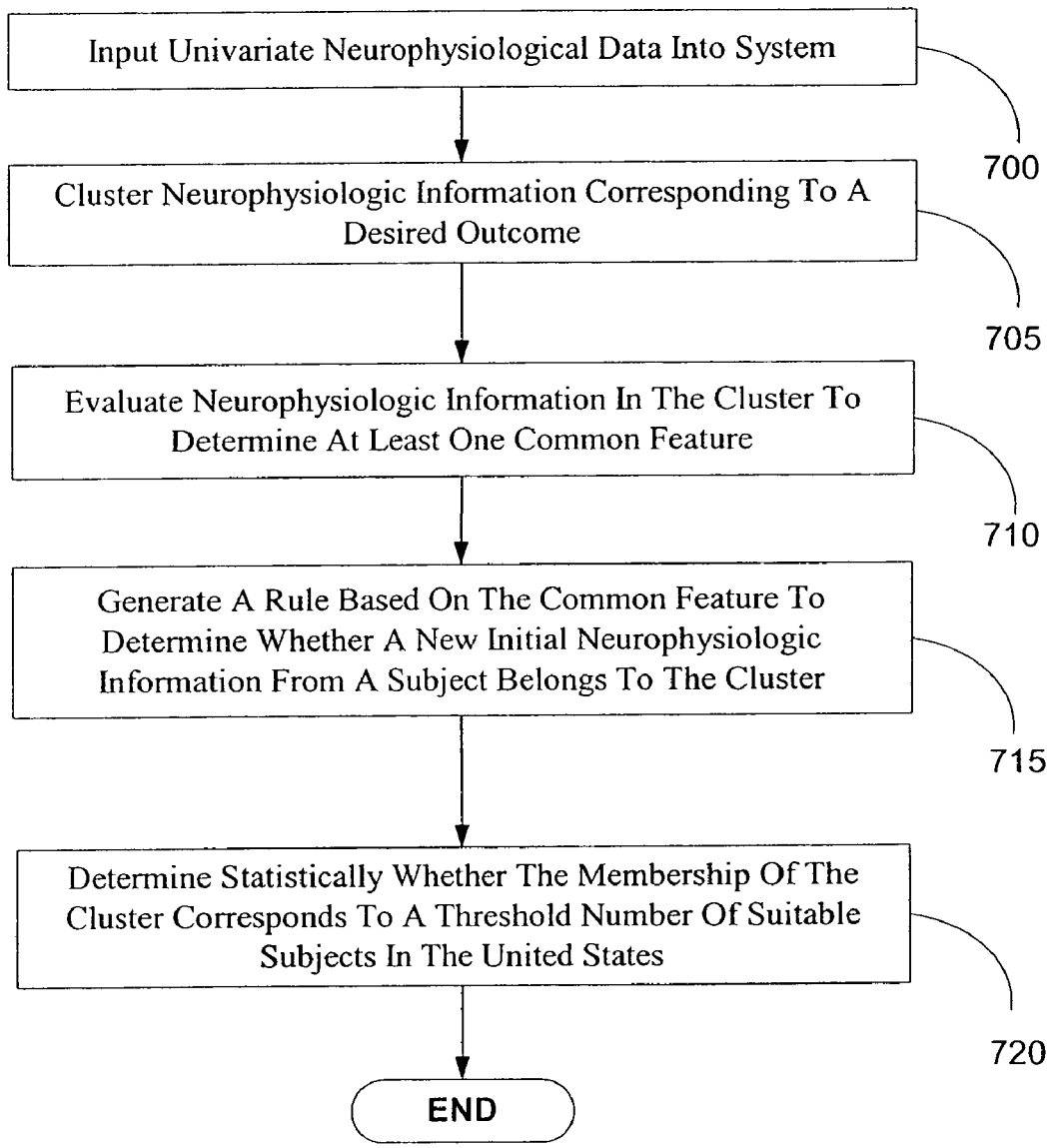
FIG. 7 illustrates another exemplary method for re-evaluating neurophysiologic information of subjects having a known response to an agent to determine beneficial responses to the agent.

FIG. 7 shows the steps in another illustrative exemplary method for re-evaluating data, for instance from a study that failed to find a beneficial effect in a desired threshold fraction of patients. This is a common occurrence with promising laboratory therapeutic entities failing to benefit enough patients resulting in difficulty in even distinguishing between a placebo and the therapeutic entity. In an additional feature, considerable data exists for responses to a number of therapeutic entities but their desirable effects in the context of treating mental state are not easily identified due to the presence of a significant number of non-responders. However, prospective identification of non-responders as taught by the invention enables discovery of such new uses and safe uses of known therapeutic entities.

Briefly, to this end it enables identification of one or more conditions precedent for indicating the use of a candidate therapeutic entity that otherwise has failed to demonstrate effectiveness in a trial. This follows from the discovery that many therapeutic entities are heterogeneous in their effect since they are effective against more than one diagnosed condition while not being effective on all subjects sharing a common diagnosed condition. Thus, a candidate therapeutic entity appears to be ineffective or even deleterious in some subjects if administered in response to a common traditional diagnosis. However, prescreening the subjects with the aid of neurophysiologic information enables selecting subjects predisposed to respond to the therapeutic entity in a desirable manner while avoiding the confounding presence of non-responders or subjects susceptible to adverse responses.

Univariate variable values for neurophysiologic information from a plurality of subjects is obtained for analysis during step 700 in accordance with the invention and, preferably with the aid of statistical and database tools. The neurophysiologic information corresponding to an outcome of interest is clustered during step 705 such that a cluster corresponds to a treatment and its outcome. The neurophysiologic information in a particular cluster is evaluated during step 710 to determine at least one common feature. Significantly, this feature is not necessarily restricted to a boundary defining set of values for the univariate or multivariables. During step 715, the common feature is used to generate a rule for prospective evaluation of new subjects. Finally, the expected fraction of subjects relative to the population of the United States (or another jurisdiction of interest) that is capable of exhibiting the desirable response is determined during step 720.

Generalizing the process of multivariable generation creates a table of similarly derived measures for an individual patient. An example therapeutic entity-response-specific characterization of brain dysfunction for an individual patient is summarized according to each multivariable in TABLE 7.

TABLE 7

| Multivariable | Value | Multivariable | Value |
|---|---|---|---|
| RMAD | −35 | CABL | 5 |
| RMPD | −23 | CABR | 10 |
| RMAT | −40 | FMAD | −34 |
| RMPT | −33 | FMPD | −30 |
| RMAA | 40 | FMAT | 3 |
| RMPA | 27 | FMPT | 5 |
| RMAB | −30 | FMAA | 33 |
| RMPB | −21 | FMPA | 15 |
| CEAD | 4 | FMAB | −4 |
| CEPD | 0 | FMPB | 10 |
| CEAT | 5 | AADL | 0 |
| CEPT | 5 | AADR | 1 |
| CEAA | −1 | AATL | 3 |
| CEPA | 40 | AATR | 3 |
| CEAB | 10 | AAAL | 3 |
| CEPB | 20 | AAAR | 3 |
| AEMD | −6 | AABL | 0 |
| AEMT | −6 | AABR | 0 |
| AEMA | 9 | CEBD | 2 |
| AEMB | −9 | CEBT | 2 |
| AEBD | −1 | CEBA | 26 |
| AEBT | −1 | CEBB | 3 |
| AEBA | −5 | RBDL | −13 |
| AEBB | −1 | RBDR | −10 |
| CADL | 2 | RBTL | −18 |
| CADR | 1 | RBTR | −21 |
| CATL | 1 | RBAL | 21 |
| CATR | 1 | RBAR | 22 |
| CAAL | 18 | RBBL | −12 |
| CAAR | 11 | RBBR | −11 |

In the example summarized in TABLE 7, the patient has a RMAA value of 40. This value would be expected to occur in the normal population only 3 times in 100,000 observations. Thus, the multivariable RMAA significantly deviates from its expected value. A patient with this RMAA value is judged as having a physiologic brain imbalance of the RMAA type and classified accordingly.

A result of applying rules to multivariables, such as that represented in TABLE 7 is compared to the result expected for a particular treatment. Not every treatment requires that every multivariable have a prescribed range of values. Instead, it is possible to identify multivariables that are significant in distinguishing between various agents and treatments. For instance, a beneficial response to PROZAC is evaluated by applying rules corresponding to index numbers 1, 2, 4, 6, 8, 11, 12, 14, 16, 17, 19, 25, 27, 32, 33, 35, 41, 43, 57-60, 63-67 and 71 in TABLE 6 for a total of 23 rules. These rules represent a signature for PROZAC. Similar signatures are determined for other treatments. Notably, not all of the rules in a signature need to be satisfied exactly. Instead, substantial agreement with the rules is sufficient to make a prediction and rank multiple predictions.

In addition to PROZAC, several other well-known therapeutic entities have suitable signatures. Example signatures are listed to provide an illustrative sample of therapeutic entities suitable for evaluation by the method and system of the invention. CLONAZAPAM is associated with rules corresponding to index numbers 2, 3, 10, 13, 15, 18, 20, 21, 23, 29, 31, 34, 36, 53-56, 61, and 62 in TABLE 6 for a total of 19 rules. DEPAKOTE is associated with rules corresponding to index numbers 2, 10, 15, 16, 19, 27, 34, 36, 57-60, and 71 in TABLE 6 for a total of 15 rules. EFFEXOR is associated with rules corresponding to index numbers 1, 2, 4, 6, 8, 11, 14, 16-17, 19, 25, 27, 32, 34, 36, 41, 43, 57-60, 63-66, 69 and 71 in TABLE 6 for a total of 27 rules. LAMICTAL is associated with rules corresponding to index numbers 3, 12, 13, 15, 18, 20-21, 24, 30, 32, 34, 36, and 53-58 in TABLE 6 for a total of 18 rules. Lithium is associated with rules corresponding to index numbers 1-2, 14, 16, 18-19, 25, 27, 30, 32-33, 35 59-60 63-64, and 71 in TABLE 6 for a total of 17 rules. PARNATE is associated with rules corresponding to index numbers 3, 5, 7, 9-10, 13, 15, 18, 20-24, 30-32, 34, 36, 53-56, 65, 67, and 69-72 in TABLE 6 for a total of 28 rules. And, TEGRETOL is associated with rules corresponding to index numbers 1-2, 11, 14, 16-17, 20, 25, 32-33, 36, 57-58, 63-64, 69 and 72 in TABLE 6 for a total of 17 rules. Additional drugs and their associated signatures are attached to this specification in APPENDIX 1.

It should be noted that the signatures described above are not limitations on the scope of the invention, but instead illustrate the invention for a particular choice of multivariable representation of clusters of pretreatment neurophysiologic information. Alternative representations are, therefore, intended to be within the scope of the invention.

Figure 8:
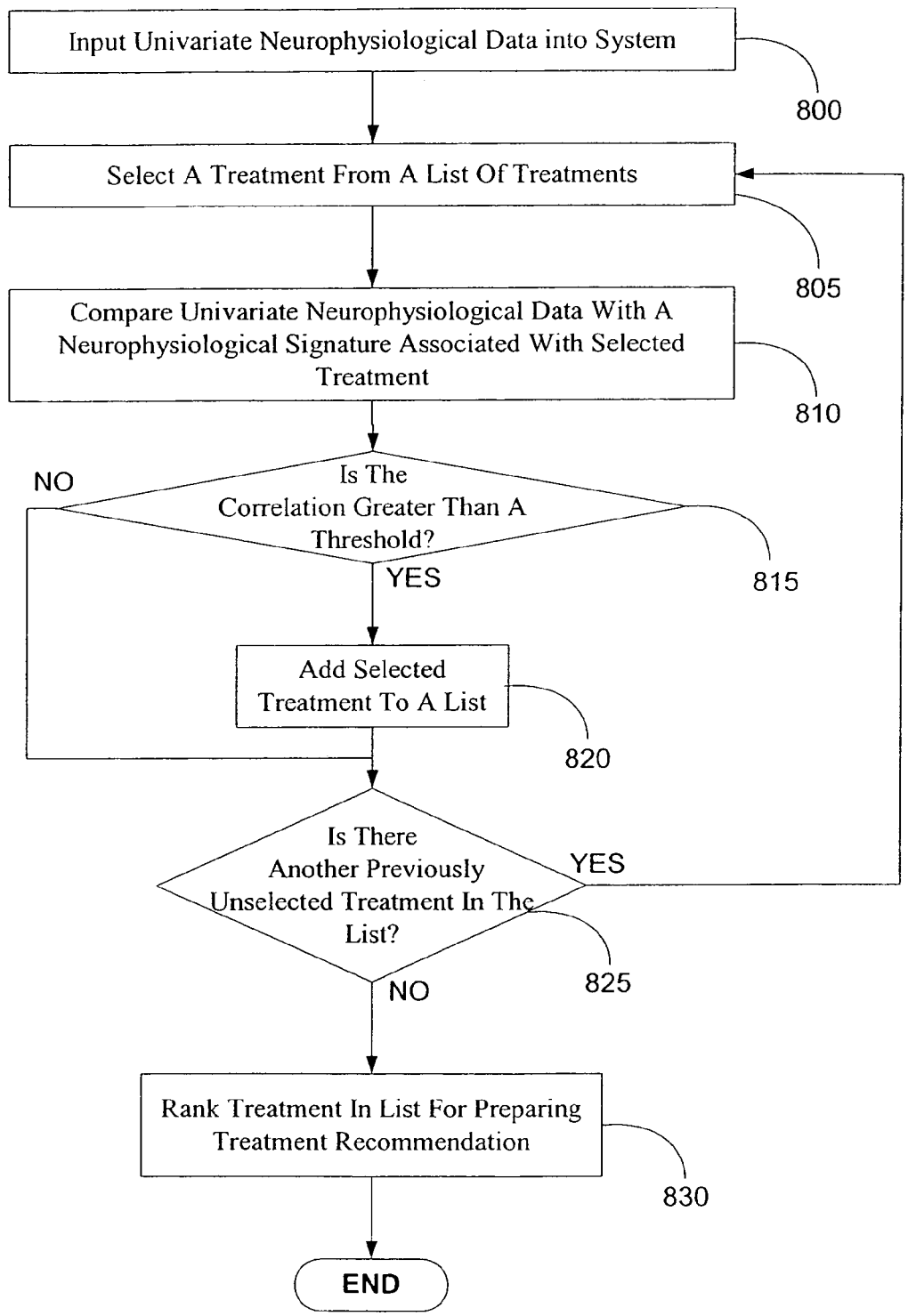
FIG. 8 illustrates an exemplary method for correlating a treatment signature with neurophysiologic information of a subject.

FIG. 8 illustrates an exemplary method based on correlating a treatment signature with neurophysiologic data. Following acquisition of neurophysiologic information during step 800, a treatment is selected from a list of treatments during step 805. The list of treatments may be associated with a cluster or be generated by a clinician seeking to evaluate one or more treatment entries therein. The neurophysiologic information is compared to the signature of the selected treatment during step 810. If the correlation between the neurophysiologic information and the signature is less than a specified threshold, then control returns to step 825 for the selection of a new treatment in the list. The use of a threshold allows tuning the rule matching to allow for less than perfect matches, i.e., a substantial match. Otherwise, control passes to step 820. During step 820 the selected treatment is added to an output list. During step 825 if there are additional treatments in the list of treatments, then control returns to step 805. Otherwise, control passes to step 830 wherein the treatments in the output are ranked if a different order is required, thus completing the method. The ranking of the treatments provides an additional flexibility by allowing, for instance the outputs associated with each of the treatments in the list of treatments to be reflected for the benefit of a clinician.

Figure 9:
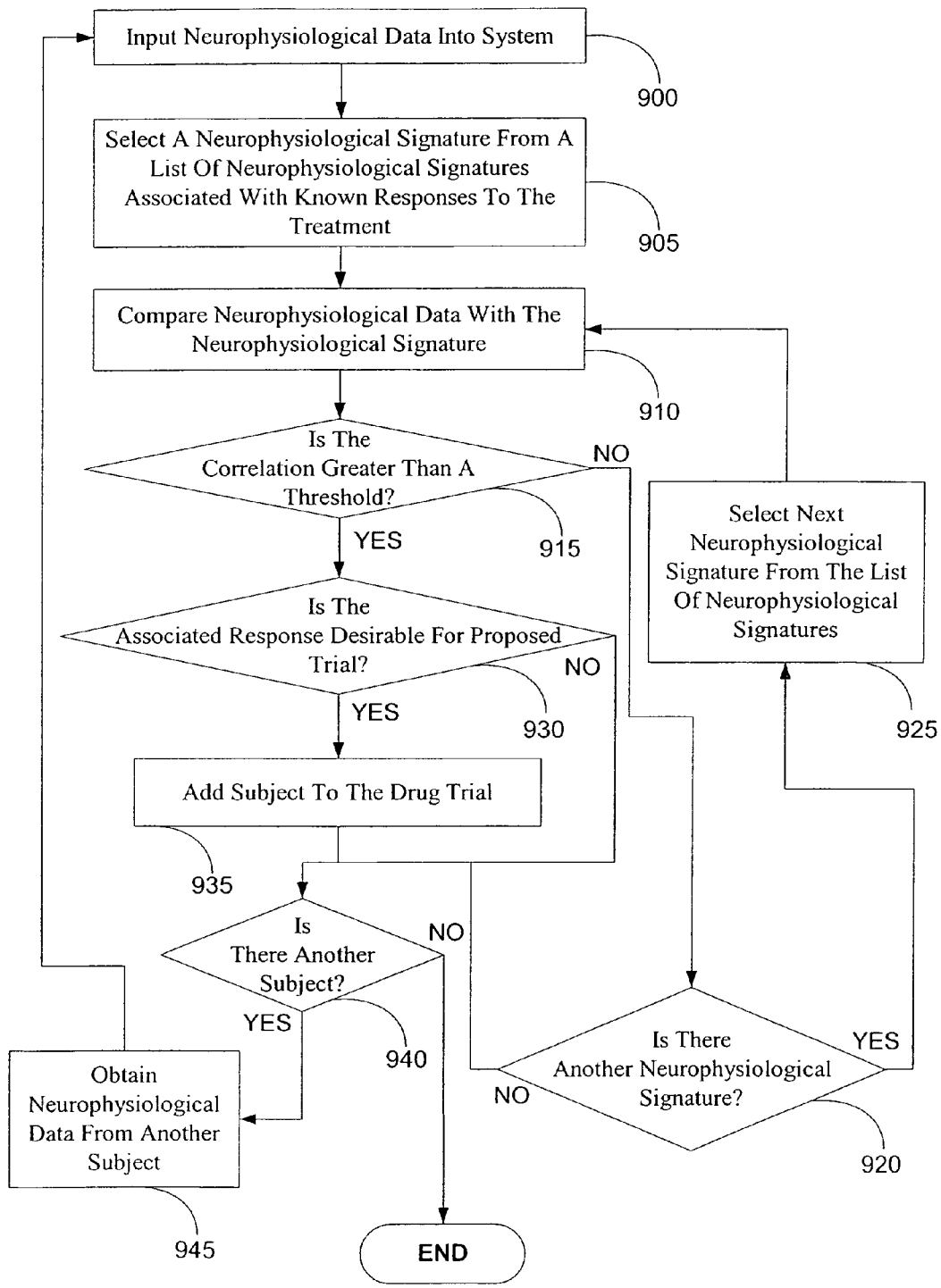
FIG. 9 illustrates an exemplary method for evaluating a subject for inclusion in a clinical trial.

FIG. 9 illustrates an exemplary embodiment of the invention for evaluating a subject for inclusion in a clinical trial. As previously noted, the present invention further enables a method and system for screening individual human participants for inclusion in clinical trials of new compounds, or for known compounds for which new uses are proposed. In clinical trials, the appropriate choice of study subjects assures that the findings of the trial accurately represent the drug response of the target population. Typically, an investigator who wants to study the efficacy of a new therapeutic entity begins by creating inclusion and exclusion selection criteria that define the population to be studied.

The present invention enables conducting clinical trials of new therapeutic entities or known therapeutic entities for which new uses have been indicated using "enriched" sets of test participants. The therapeutic entity responsivity profiles of test participants with behaviorally defined indicia of psychopathology and related EEG/QEEG abnormalities can be accurately gauged using EEG/QEEG throughout the clinical trial period. Changes in QEEG multivariate output measurements can then be correlated with an outcome measure such as CGI scores to track therapeutic entity efficacy.

In an exemplary embodiment of the invention, a candidate therapeutic entity is administered to subjects having a known initial neurophysiologic information. Following treatment with the therapeutic entity candidate active-treatment neurophysiologic information reveals the effect of the candidate substance. This effect of the substance, for instance, is reflected in an increase in alpha frequency range dependent parameters. The substance then is deemed suitable for testing for alleviating one or more traditionally diagnosed mental conditions associated with a decrease in alpha frequency range dependent parameters in EEG data. Therefore, subjects exhibiting deficit in alpha frequency range dependent parameters, are selected for studying the therapeutic effect of the substance. Additional specificity is possible by evaluating the neurophysiologic information at finer resolution.

In psychiatry, the clinical characteristics that have traditionally contributed to the definition of inclusion characteristics have been based on behavioral diagnosis as outlined by the DSM, ICD, both cited earlier, or similar classification systems known to the art. In the method of the present invention, EEG/QEEG information is used in conjunction with behavioral diagnosis, as an inclusion criterion to guide sample selection.

First, behavioral diagnosis typically screens potential sample subjects. However, the method and system of the present invention do not require the behavioral diagnosis. Second, a desired profile for study participants based at least in part on EEG/QEEG abnormality patterns and optionally the behavioral diagnosis correlates is chosen. And third, potential study participants with the desired EEG/QEEG abnormality patterns and behavioral correlates are recruited as potential participants in the trial.

Turning to FIG. 9, the neurophysiologic information of the subject is obtained during step 900. In view of the possibility that there may be more than one set of rules, i.e., signatures corresponding to a treatment, a signature is selected from a list of such signatures during step 905. For instance, there may be non-contiguous clusters associated with the treatment or multiple clusters associated with different outputs following the treatment, each having its own signature. Next, analogously with steps 810 and 815 of FIG. 8, during steps 910 and 905 a determination is made of the correlation between the neurophysiologic information and the selected signature. If the correlation is less than a threshold then control passes to step 920 to evaluate another neurophysiologic signature, which is selected during step 925 with control returning to step 910. Otherwise control passes to step 930 from step 915.

During step 930 the outcome associated with the treatment signature is evaluated so determine whether it is a desirable (or undesirable) for the purpose of the proposed trial. If the associated outcome precludes including the subject in the trial then control passes to step 940. Otherwise, control passes to step 935 during which the subject is added to the clinical trial and control passes to step 940. A determination that there is another prospective subject during step 940 results in the control returning to step 900 via the step 945 for obtaining neurophysiologic information from a new subject. Otherwise the method terminates.

As explained previously, the invention further enables better treatment, by prospectively evaluating putative treatments for diagnosed mental disorders. Some such disorders include, without being limited to the recited list, the following: agitation, attention deficit hyperactivity disorder, atypical asthma, Alzheimer's disease/dementia, anxiety, panic, and phobic disorders, bipolar disorders, borderline personality disorder, behavior control problems, body dysmorphic disorder, atypical cardiac arrthymias including variants of sinus tachycardia, intermittent sinus tachycardia, sinus bradycardia and sinus arrthymia, cognitive problems, atypical dermatitis, depression, dissociative disorders, eating disorders such as bulimia, anorexia and atypical eating disorders, appetite disturbances and weight problems, edema, fatigue, atypical headache disorders, atypical hypertensive disorders, hiccups, impulse-control problems, irritability, atypical irritable bowel disorder, mood problems, movement problems, obsessive-compulsive disorder, pain disorders, personality disorders, posttraumatic stress disorder, schizophrenia and other psychotic disorders, seasonal affective disorder, sexual disorders, sleep disorders including sleep apnea and snoring disorders, stuttering, substance abuse, tic disorders/Tourette's Syndrome, traumatic brain injury, trichotillomania, or violent/self-destructive behaviors.

In this aspect of the invention, the invention guides choices for treating the above-listed psychiatric, medical, cardiac and neuroendocrine disorders with various therapeutic regimes, including, but not limited to: therapeutic entity therapy, phototherapy (light therapy), electroconvulsive therapy, electromagnetic therapy, neuromodulation therapy, verbal therapy, and other forms of therapy.

In an aspect of the invention, following a traditional diagnosis of a subject it is possible to further evaluate the traditional treatments to determine the set of treatments likely to be effective in view of the neurophysiologic information obtained from the subject. This approach not only speedily delivers care, but, also, diminishes the subject's risk of deleterious effects from avoidable experimentation.

As an added benefit, the invention not only enables reevaluation of traditional treatments, but also suggests non-traditional (novel or counter intuitive) treatments that are suitable for the particular subject's neurophysiologic information. The invention enables different neurophysiologicly referenced treatment strategies that are safe and effective for subjects who share a common diagnosis, because each treatment strategy is tailored to specific neurophysiologic information.

Conversely, many subjects having different behavioral diagnosis respond well to the same treatment. Such subjects are treated accordingly by the methods taught by the present invention while traditional diagnostic and treatment methods are biased by the proportion of patients that respond well to a common set of treatments resulting in less than effective treatment of smaller sub-groups of patients.

In one aspect of the invention, a subject's univariate Z-scores are compared directly with the information contained in a treatment-response database. In the therapeutic entity therapy aspect of the present invention, this comparison identifies a cluster, in turn defined by multivariables, to which the subject's univariate Z-scores are related. It is possible to identify treatments that are likely to correct EEG/QEEG abnormalities by either tracking the effect of a treatment on the subject's Z-scores directly or a sub-set of the subject's Z-scores. For example, the sub-set is conveniently chosen to include the univariate variables included in the definitions of the multivariables defining the cluster. Thus, the effect of treatment on the EEG/QEEG based neurophysiologic information allows both follow-up evaluations and another measure of the outcome of the treatment. A clinician can use this measure to guide additional therapeutic choices.

At least two types of analysis are possible according to the method of the present invention—Type-one and Type-two Analysis. Type-one Analysis provides that subjects are therapeutic entity free. Type-two Analysis, discussed below, provides for patients who will not or cannot be therapeutic entity free. Therapeutic entity status preferably duplicates that of the reference distribution for calculating Z-scores. Subjects included in the outcomes database are preferably free of therapeutic entity for at least seven half-lives of their prior therapeutic entity and its metabolites.

In the Type-one analysis, a subject's baseline EEG/QEEG is then matched with similar EEG/QEEGs and their correlated therapeutic entity outcomes in the outcomes database. As indicated, the outcomes database includes treatment modalities that convert the abnormal multivariate parameters of these patients toward normal. Next, a neuroactive therapeutic entity candidate is identified in the outcomes database according to its physiological effects on brain function as indicated in the CGI score or—a more direct measure of the effect of a treatment on the neurophysiologic information. Since the clusters in the Outcomes Database are associated with a treatment and its outcome, each therapeutic entity is classified by its influence on EEG/QEEG information. This procedure furnishes the physician with a physiological link between the therapeutic possibilities and their effect on brain function across diverse symptomatic behavioral expressions.

The probability that a patient will respond to different types of treatments is then determined. These treatments include medication, classes of therapeutic entities, psychotherapy or combination thereof including various known and suspected antidepressants, anti-anxiety agents, side effect control agents, treatments for alcohol abuse, mood stabilizers, anti-ADD agents, anti-psychotics, impulse control agents, antihypertensive agents, antiarrthymics, and hypnotic agents.

In addition, in an aspect of the invention it is possible to classify treatments based on the clusters of pre-treatment neurophysiologic information known to be responsive in leading to a desired outcome. Presently, we term such a classification scheme based on a response to a treatment rather than a diagnosis an electrotherapeutic classification. As may be expected, such a scheme tracks the effect of the treatment on features of neurophysiologic information.

For instance, in the case of EEG containing neurophysiologic information therapeutic entities are known that are associated with outcomes such as an alpha deficit, an alpha excess, beta excess, delta excess, theta excess, excess energy or abnormal coherence and combinations thereof. In particular it is useful to consider the following non-exhaustive list of electrotherapeutic classes described in terms of the outcome:

Class 1: Excessive energy in the alpha band of EEG results in an alpha excess over the level associated with the age referenced distribution. This increase in energy is evaluated either at a single electrode or two or more electrodes. Some exemplary indicative variables reflecting alpha energy excess are the previously described multivariables RMAA or RMPA with values over 10 (rule 17 of TABLE 6). therapeutic entities falling in this class include PROZAC™ and EFFEXOR™.

Class 2 Excess energy in the theta or delta bands. This is indicated by the value of example multivariables RMAT, RMAD, RMPD and RMPT of TABLE 1. Example therapeutic entities include monoamine oxidase inhibitors (MAOI) and stimulants such as Adderall. Notably, administration of MAOI's increases the energy in the alpha band.

Class 3: Energy in the alpha and theta band increases. This is indicated by the value of example multivariables RMAT, RMAA, RMPT, and RMPA of TABLE 1. Example therapeutic entities include WELLBUTRIN™.

Class 4: Energy in the beta band increases. This is indicated by the value of example multivariables RMAB and RMPB of TABLE 1. Example therapeutic entities include cardiovascular system affecting agents such as beta-blockers.

Class 5: Coherence measures in EEG are affected. This is indicated by the value of example multivariables CEAD and CEPB of TABLE 1. Example therapeutic entities include Lithium and Lamictal.

As is apparent, additional or alternative classifications are possible with no loss of generality. The aforementioned classes are useful in making therapeutic recommendations, particularly in a rule based decision-making environment where decisions reflect generalizations gleaned from a treatment-response database rather than actual search of the database itself. Moreover, the use of multiple agents for treating a given subject also benefits from the availability of classes of agents to provide a broad choice of agents to accommodate therapeutic entity combinations that are contraindicated or undesirable because of adverse effects or other reasons.

The outcomes database of an embodiment of the present invention includes entries corresponding to almost three thousand patients and twelve thousand treatment episodes. It tracks treatment-response data based on EEG/QEEG information for a number of therapeutic entities known by their generic names. Examples of such therapeutic entities include: alprazolam, amantadine, amitriptyline, atenolol, bethanechol, bupropion regular and sustained release tablets, buspirone, carbamazepine, chlorpromazine, chlordiazepoxide, citalopram, clomipramine, clonidine, clonazepam, clozapine, cyproheptadine, deprenyl, desipramine, dextro-amphetamine regular tablets and spansules, diazepam, disulfiram, d/l amphetamine, divalproex, doxepin, ethchlorvynol, fluoxetine, fluvoxamine, felbamate, fluphenazine, gabapentin, haloperidol, imipramine, isocarboxazid, lamotrigine, levothyroxine, liothyronine, lithium carbonate, lithium citrate, lorazepam, loxapine, maprotiline, meprobamate, mesoridazine, methamphetamine, methylphenidate regular and sustained release tablets, midazolam, meprobamate, metoprolol regular and sustained release form, mirtazepine, molindone, moclobemide, naltrexone, nefazodone, nicotine, nortriptyline, olanzapine, oxazepam, paroxetine, pemoline, perphenazine, phenelzine, pimozide, pindolol, prazepam, propranolol regular and sustained release tablets, protriptyline, quetiapine, reboxetine, risperidone, selegiline, sertraline, sertindole, trifluoperazine, trimipramine, temazepam, thioridazine, topiramate, tranylcypromine, trazodone, triazolam, trihexyphenidyl, trimipramine, valproic acid or venlafaxine.

Treatment-response data based on EEG/QEEG information is also possible for medicinal agents having the following example trademarks: Adapin, Altruline, Antabuse, Anafranil, Aropax, Aroxat, Artane, Ativan, Aurorix, Aventyl, BuSpar, Catapres, Celexa, Centrax, Cibalith-S, Cipramil, Clozaril, Cylert, Cytomel, Decadron, Depakene, Depakote, Deprax, Desoxyn, Desyrel, Dexedrine tablets, Dexedrine Spansules, Dextrostat, Dobupal, Dormicum, Dutonin, Edronax, Elavil, Effexor tablets, Effexor XR capsules, Eskalith, Eufor, Fevarin, Felbatol, Haldol, Helix, Inderal, Klonopin, Lamictal, Librium, Lithonate, Lithotabs, Loxitane, Ludiomil, Lustral, Luvox, Manerix, Marplan, Miltown, Moban, Nalorex, Nardil, Nefadar, Neurontin, Norpramin, Nortrilen, Orap, Pamelor, Pamate, Paxil, Periactin, Placidyl, Prisdal, Prolixin, Prozac, Psiquial, Ravotril, Remeron, ReVia, Risperdal, Ritalin regular tablets, Ritalin SR tablets, Saroten, Sarotex, Serax, Sercerin, Serlect, Seroquel, Seropram, Seroxat, Serzone, Symmetrel, Stelazine, Surmontil, Synthroid, Tegretol, Tenormin, Thorazine, Tofranil, Tolrest, Topamax, Toprol XR, Tranxene, Trilafon, Typtanol, Tryptizol, Urecholine, Valium, Verotina, Vestal, Vivactil, Wellbutrin SR tablets, Wellbutrin regular tablets, Xanax, Zoloft, or Zyprexa. The generic descriptions of these trademarked agents and their source are available from the Physicians Desk Reference (New York: Medical Economics Company, 2001), the descriptions of which are herein incorporated by reference.

The EEG/QEEG information of the present invention links therapeutic entities to their effects on brain function. TABLE 6 contains selected agents in the database of the present invention, electrotherapeutically classified by 72 discriminating features. A response prediction can be made based on the magnitude of observed EEG/QEEG parameters and the subset of rules listed in TABLE 6 that are associated with a particular therapy.

Individuals who cannot be tested due to difficulty in obtaining neurophysiologic information in a therapeutic entity-free state are tested under conditions where ongoing therapeutic entities are allowed. This Type-two analysis reports the impact of therapeutic entity on the EEG/QEEG information. Follow-up EEG recordings are used to track changes produced by the administration of therapeutic entities.

Of course, when Type-Two analysis has been preceded by Type-One Analysis, it is possible to observe the absolute changes attributable to therapeutic entity and appreciate the spectrum of actions on the EEG/QEEG of a given combination of therapeutic entities. These effects can be compared to the set of initially comparable individuals and their response to the same therapeutic entity or therapeutic entities.

For patients analyzed according to Type-two Analysis without a preceding Type-one Analysis, therapeutic guidance is derived from treating the information as if it were derived from Type-one Analysis and adjusting therapeutic entity using both the electrotherapeutic agent recommendation and the current therapeutic entity information. This approach takes into account the possible known complications from therapeutic entity interactions while treating independent therapeutic entity actions as independent. In the absence of interfering therapeutic entity interactions, this approach yields a good estimate of the action of a drug and at least a starting point for further analysis.

Moreover, it is possible to define treatment to include a staggered administration of more than one substance, thus allowing the clustering procedure described previously to predict the response of a subject, including responses based on initial neurophysiologic information collected during the course of treatment for deducing treatment options with the aid of treatment-response database built in accordance with Type-one analysis.

Figure 10:
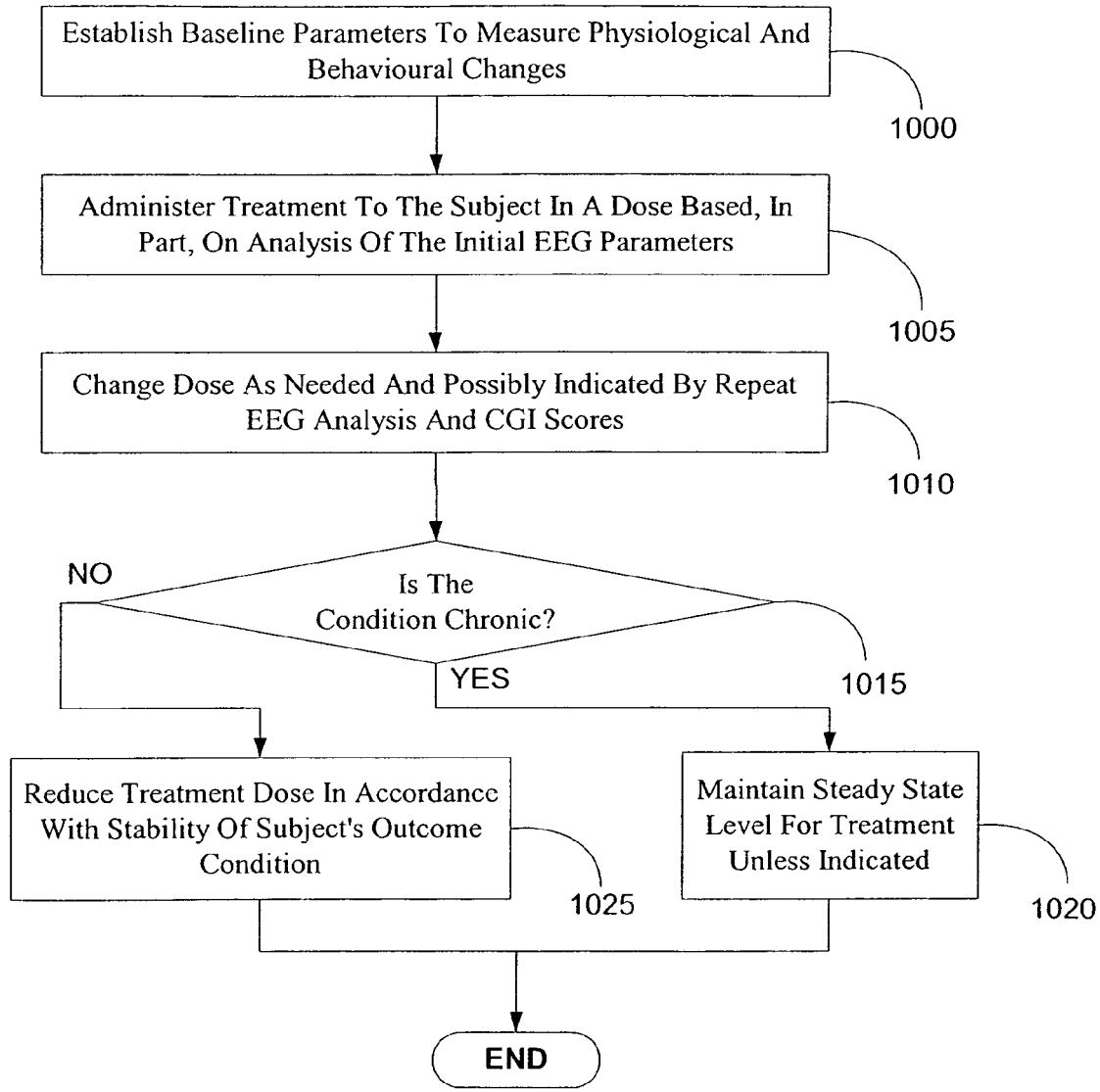
FIG. 10 illustrates an exemplary method for administering a single therapeutic entity-in accordance with the invention.

FIG. 10 summarizes a typical embodiment of the process of single therapeutic entity therapy based on the preferred EEG/QEEG method of the present invention. During step 1000 of a therapy process, one or more clinicians establish baseline parameters to measure various physiologic and behavioral changes. Next, during step 1005, the therapeutic entity of choice is administered to the patient in a dose based on EEG/QEEG analysis in accordance with the invention.

The choice of therapeutic entity is guided by the outcome predicted by the method and system of the invention for interpreting pre-treatment or initial neurophysiologic information. Moreover, response to the treatment is monitored, at least in part, by examining the effect on the neurophysiologic information. While not a requirement for practicing the invention, the active-treatment neurophysiologic information often reflects changes in indicative variables reducing deviation from age-matched reference distributions. Accordingly, dosage is changed as needed and indicated by repeat QEEG analysis and CGI scores during step 1010.

During step 1015 a determination is made as to whether the condition is a chronic condition. If the condition is chronic then control flows to step 1020. Upon reaching a steady state, as adjudged by EEG-based outcome measures and/or other outcome measures such as CGI scores, the steady state is maintained for chronic conditions. In the case of non-chronic conditions characterized by episodes of limited duration, control flows to step 1025 from step 1015. During step 1025, preferably, EEG-based outcome measures enable reduction of the dosage during step 1025.

Figure 11:
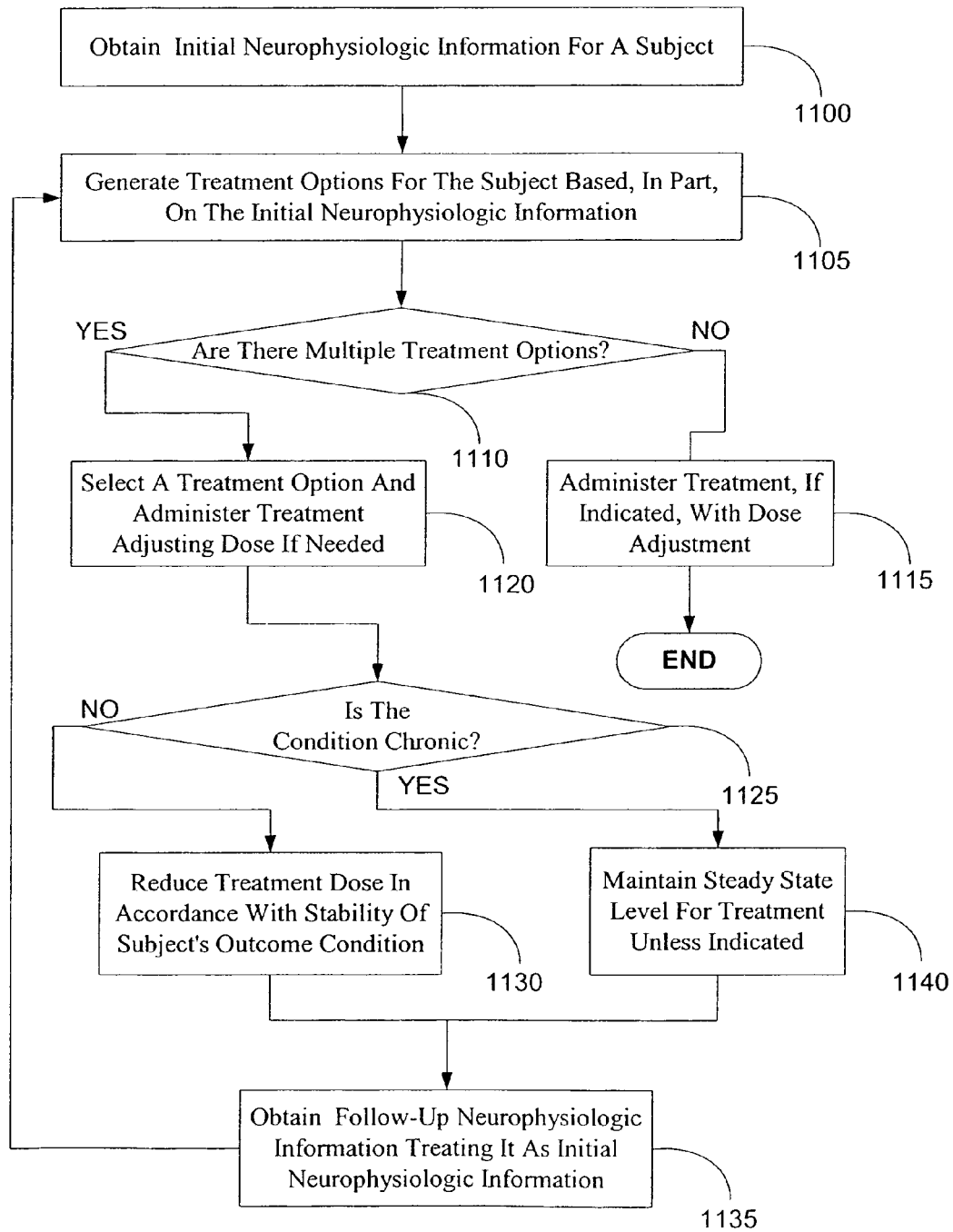
FIG. 11 illustrates an exemplary method for administering multiple therapeutic entities in accordance with the invention.

FIG. 11 summarizes an exemplary embodiment of the process of multi-agent therapeutic entity therapy based on the preferred EEG/QEEG method of the present invention. It should be noted as a preliminary matter that it is possible to suitably define a treatment as including more than one agent. However, in view of scarce data it is useful to also retain the capability of deducing a course of treatment from the treatment-response database having primarily single treatment outcomes on subjects qualifying for Type-one analysis. This strategy reduces possible errors due to unexpected therapeutic entity interactions while retaining the ability to analyze situations where different treatments do not interfere or actually supplement each other. During step 1100 neurophysiologic information for a subject is obtained. The neurophysiologic information so obtained is either initial neurophysiologic information or pre-treatment neurophysiologic information. Additional neurophysiologic information is collected, when desired, to monitor the effect of an agent following administration and deduce the need for additional agents to effect a desired improvement.

Relying upon the neurophysiologic information, at least in part, treatment options are generated in accordance with the invention during step 1105. Multiple treatment options are generated if the initial neurophysiologic information belongs to, i.e., satisfies rules for more than one cluster. During step 1110 a determination is made if there are multiple treatments. If there is only one or no treatment generated then control flows to step 1115. During step 1115 the indicated treatment, if any is administered. The administration of the treatment preferably follows steps 1010-1020 of FIG. 10 of adjusting doses as needed. These steps are advantageously carried out with the aid of a portable device such as a suitably programmed personal assistant or even a dedicated portable device for applying the rules deduced from cluster analysis of the data in the treatment-response database. However, this is not a requirement for practicing the invention. Thus, for instance, a physician may prefer a CGI scale or an alternative measure of improvement or change instead. Following, suitable adjustment of doses, the method terminates.

If there are multiple treatments then control passes to step 1120. During step 1120 one of the treatments is selected based on the strength of the match between the initial neurophysiologic information and the rules/membership of the cluster corresponding to a desired outcome and the selected treatment.

Steps 1125, 1130 and 1140 correspond to steps 1015, 1025 and 1020 respectively of FIG. 10 for adjusting the dose of the treatment. Following such adjustment control flows from either step 1130 or step 1140 to step 1135. During step 1135, follow-up neurophysiologic information is obtained either from the preceding dose adjustment steps or a new set of data is obtained. This neurophysiologic information is treated as initial neurophysiologic information and the control returns to step 1105 for reevaluation of this initial neurophysiologic information. In some instances, there is no further need for additional treatments and the method rapidly converges. Otherwise, additional treatments are generated that can supplement or even replace the first selected treatment. Moreover, a treatment can be encountered more than once during execution of the iterative steps of FIG. 11.

In an embodiment of the invention, during step 1120 of FIG. 11 treatment selection includes considering known therapeutic entity interactions. In addition, scheduling considerations have been developed for better treatment outcomes. To this end it is advantageous when faced with multiple treatment options to administer Class 4 agents before agents in other classes. Of course it should be understood that an agent having an outcome in more than one class can be used to simultaneously treat multiple features if possible. In contrast to Class 4 agents, Class 2 agents are administered last. Faced with a choice between Class 1 and Class 5 agents, it is preferable to administer Class 1 agents first. However, given a choice between Class 1 agents and neuroleptic therapeutic entity, the neuroleptic therapeutic entity is administered first.

Figure 14:
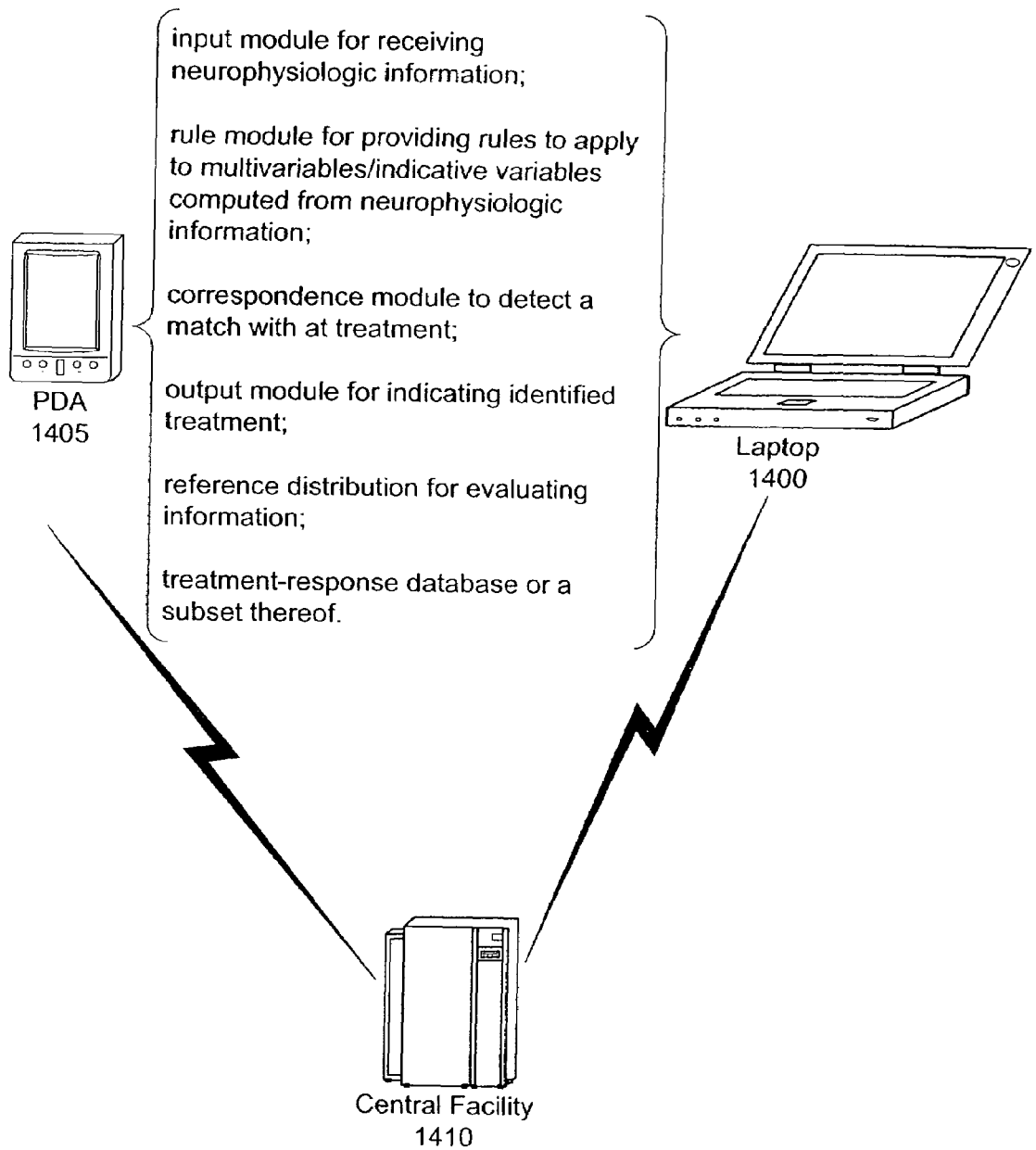
FIG. 14 illustrates a portable device based on the small footprint enabled by the identification of rules by the system and method of the invention.

FIG. 14 illustrates exemplary portable devices enabled by the present invention, in particular with the aid of the small footprint of the rules deduced from the treatment-response database. In addition, compact versions of the treatment-response database and remote diagnosis and treatment with the aid of a communication link to a central facility are also enabled and improved by the present invention. Laptop computer 1400 and a handheld device PDA 1405 include modules for receiving input, providing output, accessing rules, making correspondences, and reference distributions for evaluating information. In addition, subsets or compact versions of truly extensive treatment-response databases are possible as well.

Laptop computer 1400 and the PDA 1405 can communicate with a central facility 1410 via a communication link that is implemented as a wireless, infra-red, optical or electrical connection including hybrid combination thereof. The central facility provides extensive analytical tools, software, expansive databases to analyze and evaluate one or more neurophysiologic information sets of interest. In particular, with data collected using techniques other than EEG, data analysis is likely to be more demanding of computational resources even with the dramatically improved computational devices available today. Moreover, copyrights and intellectual rights prevent full copies of such software to be loaded on PDA 1405 and laptop computer 1400 in an economical fashion resulting in a preference for remote analysis of such data if required. Thus, the ability to formulate rules to replace databases not only provides a fast and small footprint embodiment of the invention it enables many variations on suitable software to provide additional choices to users. Moreover, licensed users, in an exemplary embodiment of the invention, subscribe to obtain updates on rules as they are refined with the aid of additional data continually being added to the treatment-response database.

Figure 15:
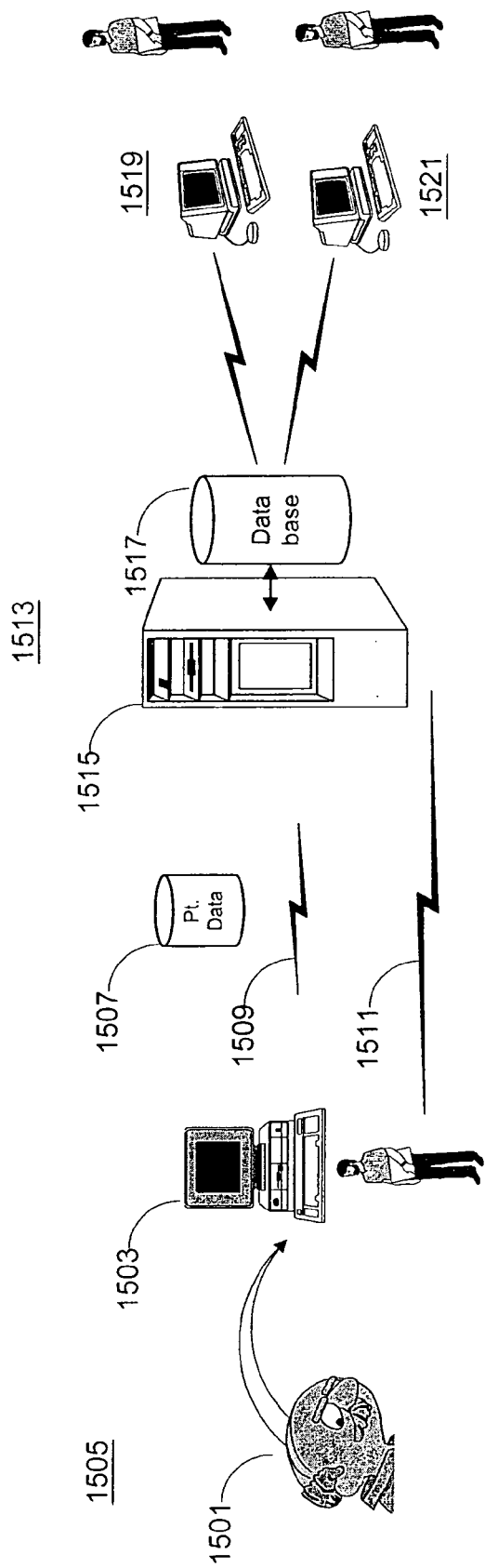
FIG. 15 illustrates an embodiment for remote treatment and assessment by the methods of the invention.

FIG. 15 illustrates an exemplary embodiment of the present invention where patient data gathering and/or treatment may be remote from patient data processing performed according to the methods of this invention, and where both data gathering and processing may be remote from or required patient evaluation or assessment. Illustrated here is data-gathering site 1505 at which quantitative neurological information, specifically EEG information, is being obtained from patient 1501 by means of processing device 1503. As described above, device 1503 may be a basic EEG device for recording raw EEG data; or may be a QEEG device capable of certain preprocessing (for example, into z-scores) of raw, recorded data followed by remote data transmission of the raw and preprocessed results; or may be a computer (such as a PC-type computer) in combination with an interface for receiving neurological data, such as EEG data, that records, optionally preprocesses, and transmits recorded neurological data, or the like. In particular, site 1505 may be a doctor's office where data gathering is supervised by patient 1501's physician (who need not be psychiatrically trained), or may be in a clinical laboratory setting supervised by a technician, or may even be the patient's home or bedside, or elsewhere Although device 1503 is generally colocated with patient 1501 at site 1505, these are in general remotely located from assessment processing center 1513 where gathered data is processed according to any of the methods of this invention. Accordingly, data recorded from patient 1501 (along with other patient data such as demographic data, medical and treatment history, prior test results, and the like) is transmitted to processing center 1513. Most simply, gathered data may be recorded on computer-readable medium 1507 which is then physically carried or mailed to center 1513. However, this data is preferably communicated 1509 by known real-time communication means, such as by a LAN, or by the Internet, or by a communication link such as a leased or dial-up telephone connection, a satellite link, or the like. Assessment results, treatment recommendations, and other output of the methods of this invention may then be transmitted 1511 back to the physician or technician at site 1505 by any of these transmitting means.

In this embodiment, patient data is processed for treatment or assessment purposes at site 1513, which includes at least computer 1515 and database device 1517. Computer 1515 may for example be a workstation or server computer, and database device 1517 may be known mass storage hardware, such as one or more hard disks. Device 1517 may store programs constructed using known software technologies and which when executed by computer 1515 cause it to perform the methods of this invention. These stored programs may also be stored on computer-readable media (or transmitted over a network) for distribution to other assessment sites. Device 1517 may also store a treatment-response database and any other data used by the invention's methods for assessing patient neurological data.

Patient data processing may be supervised and quality reviewed by, preferably, a psychiatrically-trained physician(s) who is present either at site 1513 (not illustrated) or at remote site 1519. Preferably, such a reviewer(s) ensures that the received patient data is of sufficient quality, that the various processing steps performed at site 1513 produce clinically-reasonable results from the received data, and that any final assessment or treatment recommendations to be transmitted are appropriate in view of all the patient data. An access system (or more than one) at site 1519 makes such information available to the reviewer as is needed for the review, and may optionally permit the reviewer to adjust or control patient data processing.

Also illustrated is site 1521 where a further user (using a further access system) evaluates patient available information. Such a further user may be a consulting physician who, along with a primary physician, also needs to evaluate patient data and assessments. Also, such a further user may be gathering additional treatment-response data to add to the system database. Generally, this further user may access system data for reasons appropriate in the other methods of the present invention, such as for evaluating trials of a therapeutic agent (either a new agent or a new use for a known agent), or for evaluating patients for incorporation into a planned trial of a therapeutic agent, or so forth.

It should be understood, that any two of more of the sites at which various aspects of the methods of the present invention are carried out, such as illustrated sites 1505, 1513, 1519, and 1521, may be "remotely located" from each other, where "remotely located" refers to sites that may be separately located in a single city, or that may be separately located in a single country or on a single continent, or that may be separately located in different countries or on different continents, or that may be separately located with other geographic separations. Alternatively, any two or more of these sites may be "colocated," where "colocated" refers to sites in the same room or building, or generally within the extent of a single local area network (such as an intra-hospital Ethernet), or so forth. In all cases, data transmission are preferably carried out with the security necessary or required in view of the transmission modality to protect patient confidentiality.

It should be further understood that the present invention includes both the methods and systems directly or indirectly illustrated in FIG. 15. Such methods would generally include transmitting, processing, and receiving occurring at remotely located or colocated sites. Such systems would include transmitting devices, receiving devices, and processing devices for carrying out these methods. Also the invention generally includes program products comprising computer-readable media with encoded programs for carrying out any or all of the methods of the present invention.

Figure 12:
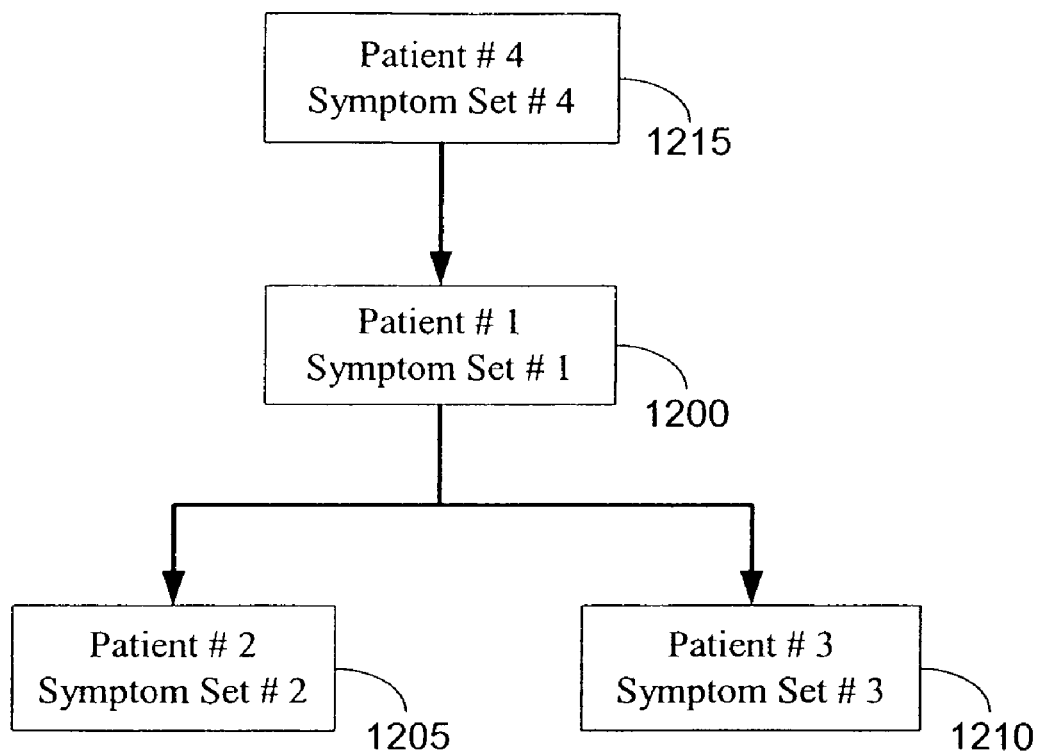
FIG. 12 illustrates an exemplary method for identifying an enriched set of subjects for identifying and isolating common genetic factors underlying response to various conditions amenable to common treatments.

In another aspect of the invention, FIG. 12 illustrates the utility of the invention in identifying inherited traits for the subsequent identification and isolation of genes responsible for pathways that underlie shared predicted responses to a treatment even when accompanied by a spectrum of disparate behavioral symptoms. Briefly, FIG. 12 represents the relationship, in a family tree, between four subjects who had similar initial or pre-treatment EEG as measured by univariate variables. Patient 1 1200 a 49 year old, married, right handed Caucasian woman reported symptom set #1. Symptom set #1 comprised a first episode of mood lability, anxiety, futility, concentration difficulties, lethargy, irritability, over-reactivity and insomnia that had been present for several months. There was no suicidal ideation or drug/alcohol use. Mental status examination revealed a pleasant female whose appearance, behavior and cognitive performance were within normal limits. Patient 1 1200 met criteria for Mood Disorder NOS (296.90) in accordance with DSM.

Patient 2 1205, daughter of patient 1 1200, reported symptom set #2. Symptom set #2 comprised a recurrent episode of dysphoric mood, headaches, diffidence, incontinent crying spells, anergy and hypersomnia accompanying three years of academic failure. There was no drug or alcohol use and no previous therapeutic entity. Mental status examination revealed a somber, self-disparaging teen whose cognitive testing demonstrated inattentive mistakes on serial seven subtractions and inability to repeat more than 4 digits backward. Patient 2 1205 met criteria for Dysthymic Disorder, early onset (300.40), Provisional Attention Deficit Disorder (314.00), Provisional Learning Disorder NOS (315.9) in accordance with DSM.

Patient 3 1210, son of patient 1 1200, reported symptom set # 3. Symptom set # 3 comprised recurrent episodes of increasing anxiety and involuntary, reclusive behavior. Despite chronic academic difficulties, he had graduated from high school. He reported deficiencies in energy, mood, sociability, appetite and reading comprehension. No drug or alcohol use, impulsivity, sleep disturbance or distemper was reported. Mental status exam revealed a frustrated, amiable male who was preoccupied with self-criticism. Cognitive examination showed inability to perform serial subtraction of 7's from 100 and slowness with dyscalculia during serial subtraction of 3's from 30. Digit retention was 5 forward and backward. Diagnoses were Anxiety Disorder with obsessive and phobic symptoms due to a learning disability (293.89), Attention Deficit Disorder (314.00), Learning Disorder NOS (315.9) in accordance with DSM.

Patient 4 1215, mother of patient 1 1200, reported symptom set # 4. Symptom set # 4 comprised chronic insomnia, ascribed to an inability in quieting her mind. This complaint had proven refractory to multiple hypnotics and only slightly responsive to lorazepam. She admitted occasional frustration and distemper, but denied any dysphoria or mood swings. Family members reported chronic mood excursions with agitation. Mental status exam revealed an engaging and optimistic woman. Cognitive examination was within normal limits. Dyssomnia Disorder NOS (307.47) was diagnosed in accordance with DSM [familial data suggesting Atypical Bipolar Disorder (296.8)].

Despite the different behavioral diagnosis in accordance with the criteria set forth by DSM, patient 1 1200, patient 2 1205, patient 3 1210, and patient 4 1215 shared similar EEG patterns and responded positively to the same agents that included carbamazepine and buprupion. In contrast, two family members—a sister of patient 1 1200 and a grand daughter of patient 1 did not exhibit the alpha frequency deficits. The sister was diagnosed with dysthymic disorder, early onset (300.40). The granddaughter was diagnosed with an EEG that was within normal variation with an attention deficit disorder 314.0 about 1.5 years later. Her EEG was slightly slow for age, and the QEEG exhibited diffuse theta excess. She was successfully treated with amino acids: L-tyrosine, L-glutamine and L-glutamine and did well.

Thus, the three generations depicted in FIG. 12 share a common response to common treatments indicating an inherited trait represented by one or more genes. However, the individual subjects present different behavioral symptoms resulting in multiple diagnosis. These heterogeneous symptoms reflect the interaction of a shared set of genes with a multitude of other genes. Therefore, isolation of a population that shares a common set of genes of therapeutic significance is not possible in general by methods based on DSM based diagnostic methods. On the other hand, the outcomes database in this illustration of the system and method of the invention readily identified an enriched set of subjects for further screening to isolate responsible genes and develop better agents to modulate their action. Thus, the invention provides a method and system to identify an enriched population of subjects that can be further dissected to isolate finer common responses to treatment to various agents for isolation of genetic traits of interest.

This exemplary application of the present invention is better understood by analogy. For instance, many agents target multiple receptors and other proteins. Anti-inflammatory agents such as aspirin, ibuprofen and the like present such an example. These agents target both COX-1 and COX-2 receptors. However, for pain management without side effects such as ulceration of the stomach, it is desirable to target only the COX-2 receptors. Newer therapeutic entities such as VIOXX provide such specificity. Similarly, to develop targeted agents for treating mental diseases it is necessary to have methods and system for tracking in detail the response to therapeutic entity based on the effect on mental disease or function. This is enabled by the treatment-response database as employed by the present invention since it not only predicts the response to treatment, but tracks a therapeutic entity by the response thereto including possible side effects. Furthermore, it enables a fine structure analysis by identifying clusters sharing a particular response, such as lack of an undesirable side effect while maintaining a positive response otherwise. Such fine structure analysis requires the large number of subjects included in the treatment-response database of the invention along with the facility to repeatedly perform cluster analysis to better define different populations of interest efficiently.

The present invention is further described in the following examples that are intended for illustration purposes only, since numerous modifications and variations will be apparent to those skilled in the art. The first example describes the use of the utility of the invention in guiding treatment following a traditional diagnosis in accordance with a standard like the DSM. The second example illustrates the identification of features associated with successful and unsuccessful outcomes of a treatment. The third example illustrates the large number of novel uses for known therapeutic entities identified by the method and system of the present invention.

Example patients with chronic Major Depressive Disorder (MDD), non-responsive to at least two previous therapeutic regimens of adequate dosage(s) and duration were studied. Their lack of response to repeated previous clinical efforts provided a clear baseline from which to note any increase in treatment efficacy with EEG/QEEG information. These patients were assigned to control (D) and experimental (D+E) treatment groups. Every other patient meeting the study criteria was treated solely on the joint decision of the treating psychiatric resident and a supervising faculty psychopharmacologist. The other group of patients was treated using EEG directed therapeutic recommendations by the same clinicians. Patients were evaluated to exclude concurrent illness and medication status. After these assessments, a clinician that was not and would not be involved in the treatment of the patient evaluated the patient providing a basis for future assessment of treatment response by this clinician. This evaluating physician played no role in therapeutic entity selection, had no other contact with the patient until assessing outcome of treatment, had no knowledge of which experimental group the patient belonged, nor any information on the EEG/QEEG findings. This clinician made all clinical ratings used in the analyses.

Each patient had a conventional twenty-one electrode digital EEG. A rule-based classifier analyzed normalized artifact-free epochs of conventional EEG. A specific therapeutic entity outcome prediction, containing the correlated therapeutic entity responses of antidepressant, anticonvulsant and stimulant classes was reported to the treating physicians of the D+E group. Therapeutic entity outcome predictions patients in the D group were sealed until the end of the study. After six weeks on a therapeutic entity(s) at maximal tolerated dosage, the independent evaluating physician using the CGI rating scale assessed treatment efficacy.

Study outcome was also evaluated using the Hamilton Depression Rating Scale [HDRS] as well as the Beck Depression Inventory [BDI]. The mean HDRS for the D group pre-treatment was 24 and the active-treatment was 18. The BDI for the D group pretreatment was 22 and the active-treatment was 20. The mean HDRS for the D+E group pretreatment was 23 and the active-treatment was 9. The BDI for the D+E group pretreatment was 26 and the active-treatment was 13. These changes in test scores between the two treatment groups are highly significant (Friedman ANOVA 0.2(N=13; df=3) p<0.009).

In the D+E group 6 of 7 patients had a CGI change of 2 or more; additionally 4 of 7 of these patients achieved a CGI of 3 indicating no evidence of illness. In the D group 1 of 6 patients had a CGI change of 2 or more and 5 of 6 patients had a CGI change of 0 indicating no improvement (p=0.02; Fisher's exact).

When the positive and the negative predictions are combined, twelve out of thirteen predictions were correct (p=0.015; Fisher's exact). This corresponds to an 86 percent likelihood of positive patient outcome with each prediction and Youden Index of 0.8 (Youden W J. Index for rating diagnostic test. Cancer 1950; 3: 32-35).

Example patients with chronic Major Depressive Disorder (MDD), determined by two senior faculty members, who had been non-responsive to at least two previous therapeutic entity regimens of adequate dosage(s) and duration were accepted in the study from consecutive evaluations of outpatients at the Veterans Administration Medical Center, Sepulveda. Their lack of response to repeated previous clinical efforts provided a clear baseline from which to note any increase in treatment efficacy with EEG/QEEG information. Human Subjects Committee approval of the protocol was obtained. Informed consent was obtained from all study participants.

These patients were assigned to control and experimental treatment groups. Every other patient meeting the study criteria was treated solely on the joint decision of the treating psychiatric resident and a supervising faculty psychopharmacologist. No concurrent report of these choices was given to the staff of this study nor did the staff of this study have any part in the selection of these patients' therapeutic entity. This group was called DSM DIRECTED.

A psychiatric resident and their supervising faculty psychopharmacologist, who had agreed to follow therapeutic entity recommendations based on EEG/QEEG correlation, treated patients not assigned to the DSM DIRECTED group. This group was called DSM+EEG DIRECTED.

Patients taking therapeutic entities other than anti-hypertensive or hormone replacement agents were disqualified because the control groups were selected using these criteria. Also excluded were subjects with a present or past primary psychotic diagnosis, history of intramuscular neuroleptic therapy, documented closed head injury with loss of consciousness, history of craniotomy, history of cerebrovascular accident, current diagnosis of seizure imbalance, current diagnosis of dementia, presence of mental retardation or active substance abuse.

All patients were required to be therapeutic entity-free (at least seven half-lives of the longest lived therapeutic entity) and illicit substance free (ascertained by a urine screen for drugs on the day of the EEG).

Before acceptance into the study, patients were evaluated to exclude concurrent illness. The evaluation included a physical examination with laboratory studies consisting of a hemogram, chemistry panel, thyroid stimulating hormone, urine drug screen, β-HCG (in females) and an EKG. The treating physician then interviewed patients. Hamilton-D (HAM-D) and Beck Depression (BECK) Scale scores were obtained during this interview.

After these assessments, a clinician that was not and would not be involved in the treatment of the patient evaluated the patient. This initial process provided a basis for future assessment of treatment response by this clinician. This evaluating physician played no role in therapeutic entity selection, had no other contact with the patient until assessing outcome of treatment, had no knowledge of which experimental group the patient belonged, nor any information on the EEG/QEEG findings. All clinical ratings present were made by this clinician.

The DSM DIRECTED group (N=6) had 4 males and 2 females, with an average age of 45. Similarly the DSM+EEG DIRECTED group (N=7) had 5 males and 2 females and an average age of 41. All patients were in similar types and frequency of psychotherapy that was maintained for the duration of the study. TABLE 8 summarizes the composition of the patient population.

TABLE 8

| DSM DIRECTED | Number of Patients | Mean/24 h in mg |
| --- | --- | --- |
| Fluoxetine | 2 | 40 |
| Nefazodone | 1 | 300 |
| Sertraline | 2 | 175 |
| Clonezapam | 1 | 2 |
| Lithium | 2 | 1050 |
| Valproate | 2 | 1125 |
| Average Number of Medications/Patient | 1.8 | |

TABLE 9

| DSM + EEG DIRECTED | Number of Patients | Mean/24 h in mg |
| --- | --- | --- |
| Valproate | 2 | 1000 |
| Lithium | 2 | 750 |
| Paroxetine | 1 | 30 |
| Fluoxetine | 2 | 35 |
| Methylphenidate | 2 | 27.5 |
| Carbamazepine | 2 | 850 |
| Sertraline | 1 | 100 |
| Average Number of Medications/Patient | 1.7 | |

Each patient had a conventional digital EEG recorded from twenty-one electrodes were applied according to the International 10/20 System. Then, 10 to 20 minutes of eyes-closed, awake, resting EEG was recorded on a Spectrum 32 (Cadwell Laboratories, Kennewick, Wash.), referenced to linked ears. The conventional EEG was reviewed to exclude paroxysmal events, spikes, sharp waves, focal disturbances and other abnormalities apparent by visual inspection. Artifact-free epochs of conventional EEG, selected by a technician, were based on the rule that all artifact-free segments were to be included in the sample until at least 32 epochs of 2.5 seconds were obtained. EEG recordings were rejected a priori as unsuitable for further analysis due to unfavorable signal to noise ratio [less than or equal to 3:1] or if average frontal power was less than 9 $\mu V_2$.

A rule-based classifier using the current patient's neurophysiologic information profile as described above and the database from the inventor's patient population was used to review pretreatment EEG/QEEG information from each study patient. An EEG/QEEG specific therapeutic entity outcome prediction, containing the correlated therapeutic entity responses of antidepressant, anticonvulsant and stimulant classes was reported to the patient control officer. This information was distributed only to the treating physician of the individual DSM+EEG DIRECTED patient, as described above. Therapeutic entity outcome predictions for all other patients were sealed until the end of the study.

The treating physician and their faculty supervisor for both experimental groups monitored treatment in weekly follow-up sessions. The mean follow-up for the study groups was 25 weeks. After six weeks on therapeutic entity(s) at maximal tolerated dosage, treatment efficacy was assessed by the independent evaluating physician, blind to patient status [DSM DIRECTED or DSM+EEG DIRECTED] and therapeutic entity regimen, who had assessed the patient prior to treatment. This physician's prior knowledge of the patient permitted the use of Clinical Global Improvement (CGI) ratings.

Two patients, one each in the DSM DIRECTED and DSM+EEG DIRECTED groups, had EEG records that exhibited an average frontal power of less than 9 $\mu V^2$. Thus, no EEG/QEEG therapeutic entity prediction was made for these patients.

The remaining eleven patients were classified into EEG/QEEG sets based on objective spectral features. EEG/QEEG sets included relative theta frequency excess, i.e., predicted to be responsive to treatment with class 2 agents. Theta excess refers to the percentage of total power contributed by the theta frequency band in excess of that expected from the age-matched reference population previously noted. Similarly, relative alpha frequency excess predicted response to treatment with class 1 agents; and interhemispheric hypercoherence and hypocoherence predicted response to treatment with class 5 agents.

Next the outcome of the study was evaluated to determine significant differences or lack thereof between DSM directed treatment and DSM+EEG directed treatment. The HAM-D for the DSM DIRECTED group showed a mean pretreatment score of 24 compared to a mean treatment score of 18. The BECK Scale showed a mean pretreatment score of 22 compared to a mean treatment score of 20. The HAM-D for the DSM+EEG DIRECTED group showed a mean pretreatment score of 23 compared to a mean treatment score of 9. The BECK Scale showed a mean pretreatment score of 26 compared to a mean treatment score of 13. These changes in test scores between the two treatment groups are highly significant (Friedman ANOVA $\chi 2(N=13; df=3)$ $p<0.009$).

In the DSM+EEG DIRECTED group 6 of 7 patients had a CGI change of 2 or more; additionally 4 of 7 of these patients achieved a CGI of 3 indicating no evidence of illness. In the DSM DIRECTED group 1 of 6 patients had a CGI change of 2 or more and 5 of 6 patients had a CGI change of 0 indicating no improvement ($p=0.02$; Fisher's exact).

All but one patient (low power) in the DSM DIRECTED group had therapeutic entity outcome predicted from pretreatment EEG/QEEG information, but this information was not reported to the treating physicians. When the study finished, the prediction was examined with respect to the patient's clinical response.

DSM+EEG DIRECTED patients were treated with the agents that were predicted by EEG/QEEG information to produce a favorable clinical outcome. Six of seven patients in this group responded as predicted a priori by EEG/QEEG information. When the positive and the negative a priori predictions are combined, ten out of eleven predictions were correct ($p=0.015$; Fisher's exact). This corresponds to an 86 percent likelihood of positive patient outcome with each prediction and Youden Index of 0.8 (Youden W J. Index for rating diagnostic test. Cancer 1950; 3: 32-35).

Therefore, patients treated in the DSM DIRECTED group had an inferior response to pharmacotherapy. Only one of six patients demonstrated improved behavioral and clinical outcome measurements by HAM-D, BECK and CGI ratings. In comparison, six of seven patients in the DSM+EEG DIRECTED group responded with significantly improved HAM-D, BECK and CGI ratings. Furthermore, remission of symptoms or a CGI rating of 3 was achieved by four of seven patients in the DSM+EEG DIRECTED group. These therapeutic improvements would be unanticipated given the chronic and refractory nature of the imbalance in this select population This study further shows that therapeutic entity response in apparently refractory patients can be predicted by EEG/QEEG information. Also demonstrated is the ability of psychiatric physicians to incorporate EEG/QEEG information with therapeutic entity correlation as a laboratory test in clinical practice resulting in improved patient outcomes.

In another example embodiment of the method and system of the invention one hundred and three (101) consecutive patients with Mood Disturbance and Attentional Disorder were enrolled in a study. Retrospective analyses identified those neurophysiologic features associated with outcomes of pharmacotherapy.

The attentional deficit population was initially treated with a Class 2 therapeutic entity, principally methylphenidate at a dose not exceeding 1.0 mg/kg body weight per day. If the patient did not achieve a Clinical Global Improvement score of 2 (moderate global improvement) or 3 (marked global improvement) after one month of therapeutic entity, the stimulant was discontinued and secondary treatment with a Class 1 therapeutic entity was initiated. If the patient did not achieve a Clinical Global Improvement score of 2 or 3 after six weeks of therapeutic entity, the Class 1 therapeutic entity was augmented with tertiary treatment consisting of a Class 5 therapeutic entity (carbamazepine, valproic acid) or a Class 2 therapeutic entity.

Affectively disordered patients without a history of mania were initially treated with a Class 1 agent (heterocyclic antidepressant (up to 3.0 mg/kg/day) or a serotonin re-uptake inhibitor). If by six weeks the patient did not achieve a CGI score of 2 or 3, then a secondary treatment with a Class 5 agent was administered. Failure to improve after three weeks at therapeutic plasma levels caused tertiary measures to be instituted, most frequently a challenge with a class 2 agent. If the challenge demonstrated responsivity a therapeutic trial was added to the patient's regimen.

The population was heuristically divided into four groups based on objective spectral features. These groups included those who exhibited, respectively, relative alpha frequency excess, relative theta frequency excess, inter-hemispheric hypercoherence, or patients whose neurophysiologic information did not demonstrate one of the preceding profiles. The four groups were identified within both attentionally disordered and affectively disordered patients. The striking electrophysiologic similarity of the under and over eighteen year old affectively disordered groups demonstrated a robustness of these findings across ages.

As the findings demonstrate [TABLE 10 and TABLE 11], the patient samples in each of the DSM diagnostic categories studied were not homogeneous in medication response. These sub-groups were distinguishable by neurophysiologic information within each DSM category; moreover, the subgroups were qualitatively similar across the DSM diagnostic categories. The relative frequency of the subgroups differed between the categories examined as well as between age groups within the affectively disordered population. Retrospective analyses of clinical outcomes demonstrate differential responsivity to selected classes of pharmacologic agents. The outcomes show that subgroups with similar neurophysiologic features responded to the same class of pharmacological agent despite the impact of the clinical treatment paradigm and the DSM classification of the patient's presenting problems. That is, the presence of the excess frontal alpha pattern was associated with responsivity to Class 1 agents (antidepressants) whether it appeared in a patient with DSM behavioral features consistent with depressive disorder or in a patient with DSM behavioral features consistent with attentional disorder. In this study, it was also found that patients with hypercoherence responded to Class 5 agents (anticonvulsants/lithium) without regard to DSM diagnosis. These findings demonstrate the clinical utility of the present invention. The recognition of a physiologic feature common to treatment resistant schizophrenic, affective, and attentional disordered patients, will reduce morbidity with the practice of the invention in a clinical setting.

In another example embodiment of the method and system of the invention patients with DSM-III-R diagnoses of 296.xx, 311.00, and 314.xx were prospectively enrolled in a study from consecutive evaluations. Retrospective analyses of the relationships between clinical responsivity and neurophysiologic features were performed in this study in order to identify those neurophysiologic features associated with unsuccessful and successful outcomes of pharmacotherapy.

Two samples of therapeutic entity-free (no medicine for seven half-lives of the longest half-life agent) patients: those with affective imbalance diagnoses (296.xx or 311.00) and those with attentional imbalance diagnoses (314.xx) were identified by historic and clinical examination. These diagnoses were then confirmed in review by a second experienced clinician. One hundred and three (103) consecutive individuals were included in the study from those patients who were considered appropriate for the testing procedure. Two patients were excluded from the study due to unavailability of laboratory results (Chem. 24, CBC, TSH, UDS, and HCG) or the absence of a follow-up for at least six months after the initiation of pharmacotherapy.

The attentional disordered sample consisted of 46 patients, 34 males and 12 females, with a mean age of 12.4 years. The affectively disordered population consisted of 54 patients, 20 males and 34 females, with a mean age 13.5 years in the adolescent population and a mean age of 40.4 years in the adult population.

Fifty percent of the attentionally disordered population was previously diagnosed and classified as treatment refractory by the referring clinician. In the affective disordered population there was a four-fold excess of unipolar patients by DSM-III-R criteria. Only one adolescent received the diagnosis of Bipolar Imbalance.

Treatment was monitored in weekly, bimonthly, or monthly follow-up sessions using Clinical Global Improvement (CGI) ratings. CGI's taken from the patient's baseline presentation were generated using information gathered from parent and teacher Conner's scales, patient and parent interviews, contact with teachers, and the treating clinician's assessment for the attentionally disordered population.

The attentional deficit population was initially treated with a Class 2 therapeutic entity, principally methylphenidate at a dose not exceeding 1.0 mg/kg body weight per day. If the patient did not achieve a Clinical Global Improvement score of 2 (moderate global improvement) or 3 (marked global improvement) after one month of therapeutic entity, the stimulant was discontinued and secondary treatment with an class 1 therapeutic entity was initiated. If the patient did not achieve a Clinical Global Improvement score of 2 or 3 after six weeks of therapeutic entity, the Class 1 therapeutic entity was augmented with tertiary treatment consisting of a Class 5 therapeutic entity (carbamazepine, valproic acid) or a Class 2 therapeutic entity.

Affectively disordered patients without a history of mania were initially treated with a Class 1 agent (heterocyclic antidepressant (up to 3.0 mg/kg/day) or a serotonin re-uptake inhibitor). If by six weeks the patient did not achieve a CGI score of 2 or 3, then a secondary treatment with a Class 5 agent was administered. Failure to improve after three weeks at therapeutic plasma levels caused tertiary measures to be instituted, most frequently a challenge with a class 2 agent. If the challenge demonstrated responsivity a therapeutic trial was added to the patient's regimen.

The population was heuristically divided into four groups based on objective spectral features. These groups included those who exhibited, respectively, relative alpha frequency excess, relative theta frequency excess, inter-hemispheric hypercoherence, or patients whose neurophysiologic information did not demonstrate one of the preceding profiles. The four groups were identified within both attentionally disordered and affectively disordered patients. The striking electrophysiologic similarity of the under and over eighteen year old affectively disordered groups demonstrated a robustness of these findings across ages. It was further noted that all these groups share the feature of delta frequency relative power deficit and twenty-five percent (25%) of the attentional disordered patients demonstrated inter-hemispheric hypercoherence primarily in the frontal region.

The theta excess subgroup of affectively disordered patients demonstrated a spectrum with global delta frequency deficit, a theta maxima of +2.2 mean-units in the frontal polar region, a second theta maxima of +2.4 mean-units in the posterior frontal region, and a decrease of relative theta power posteriorly. The alpha excess subgroup of affectively disordered patients demonstrated a spectrum with global delta frequency deficit, alpha maxima of +2.2 mean-units in the frontal polar region, a broad frontal alpha plateau of approximately +2.0 mean-units, and a second smaller alpha relative power plateau posteriorly of +1.0 mean-unit. Inter-hemispheric hypercoherence was seen in thirty-six percent (36%) of the affectively disordered adolescent and fifty-seven percent (57%) of the adult groups, mainly between the frontal regions.

The relative frequency of each of these electrophysiologic subgroups differs across these DSM-III-R diagnostic categories and by age (TABLE 10) in statistically significant manner.

TABLE 10

| DSM-III-R Diagnostic Categories | FRONTAL ALPHA EXCESS | OTHER | FRONTAL THETA EXCESS |
|---|---|---|---|
| Attentionally Disordered | 25 [54%] | 7 [15%] | 14 [31%] |
| Affectively Disordered under 18 Years Old | 18 [72%] | 4 [16%] | 3 [12%] |
| Affectively Disordered 18 Years and Older | 17 [58%] | 8 [29%] | 4 [13%] |

At six months after the initiation of treatment CGI ratings for the frontal alpha and theta excess subgroups were divided into treatment responsive and treatment refractory patients.

Clinical response was analyzed as a function of neurophysiologic spectral findings and class(es) of pharmacotherapeutic agent(s) for the normocoherent groups as shown in TABLE 11. The frontal alpha excess/normocoherent subgroup was 87% or more responsive to class 1 agents without regard to the patient's clinical presentation with attentional or affective symptoms. The frontal theta excess/normocoherent subgroup appeared only in the attentionally disordered clinical population. In that population it was 100% responsive to class 2 agents.

TABLE 11

|  | FRONTAL ALPHA EXCESS RESPONSIVE TO ANTIDEPRESSANTS | FRONTAL THETA EXCESS RESPONSIVE TO STIMULANTS |
|---|---|---|
| AFFECTIVELY DISORDERED | 9/10 [90%] | 0 [0%] |
| ATTENTIONALLY DISORDERED | 13/15 [87%] | 7/7 [100%] |

Clinical response as a function of neurophysiologic spectral findings and class(es) of pharmacotherapeutic agent(s) for the hypercoherent populations is shown in TABLE 12. Here, the frontal alpha excess/hypercoherent subgroup was 85% or more responsive to Class 5 agents without regard to the patient's clinical presentation with attentional or affective symptoms. The frontal theta excess/hypercoherent subgroup represented only a total of 5 patients, 4 of whom (80%) were responsive to Class 5 agents.

TABLE 12

|  | FRONTAL ALPHA EXCESS RESPONSIVE TO CLASS 5 AGENTS | FRONTAL THETA EXCESS RESPONSIVE TO CLASS 5 AGENTS |
|---|---|---|
| AFFECTIVELY DISORDERED | 17/20 [85%] | 2/2 [100%] |
| ATTENTIONALLY DISORDERED | 5/5 [100%] | 2/3 [67%] |

As the findings demonstrate, the patient samples in each of the DSM-III-R diagnostic categories studied were not homogeneous. These sub-groups were distinguishable by neurophysiologic information within each DSM-III category; moreover, the subgroups were qualitatively similar across the DSM-III-R diagnostic categories. The relative frequency of the subgroups differed between the categories examined as well as between age groups within the affectively disordered population.

Retrospective analyses of clinical outcomes demonstrate differential responsivity to selected classes of pharmacologic agents. The outcomes show that subgroups with similar neurophysiologic features responded to the same class of psychopharmacological agent despite the impact of the clinical treatment paradigm and the DSM-III-R classification of the patient's presenting problems. That is, the presence of the excess frontal alpha pattern was associated with responsivity to Class 1 agents (antidepressants) whether it appeared in a patient with DSM-III-R behavioral features consistent with depressive imbalances or in a patient with DSM-III-R behavioral features consistent with attentional imbalances.

In this study, it was also found that patients with hypercoherent Neurometric patterns responded to Class 5 agents (anticonvulsants/lithium) without regard to DSM-III-R diagnosis. These findings demonstrate the clinical utility of the present invention. The recognition of a physiologic feature common to treatment resistant schizophrenic, affective, and attentional disordered patients, will reduce morbidity with the practice of the invention in a clinical setting.

The theta excess population could be divided into two subtypes: a frontal theta excess group and a global theta excess group. The frontal theta excess group responded to Class 2 agents while the global theta excess group responded to Class 5 agents. The findings are consistent with the known heterogeneity underlying DSM-III-R diagnostic categories that requires significant experimentation with therapeutic entities to identify an effective therapeutic entity.

In an embodiment of the invention, various DSM categories, for instance organized by chapters of DSM, are matched with agents found to be effective by the method and system taught by the present invention. Such a comparison is presented in TABLE 13 with known and accepted treatments corresponding to entries marked "C" and new or novel therapeutic entities found to be effective in a suitable sub-groups of subjects marked with "N." As is apparent at a glance there are many novel uses possible for known therapeutic entities that are unknown due to the lack of a systematic method and system for discovering them. The present invention provides such a method and system.

The present invention has important applications beyond relating particular patients and particular therapies. In applications focused on therapies, this invention provides, inter alia, a wealth of new uses for known therapies, uses for new therapies (in particular therapies not yet applied to behaviorally-diagnosed condition even though already used for other medical conditions), as well as new methods of determining indications for therapies.

Therapy applications, beginning with new uses for known therapies, are described with primary reference to the introductory general summary of the present invention. Because the clusters or groups of symptomatic individuals described previously are selected based on responsiveness to a particular therapy and without regard to an individual's behavioral diagnosis, each cluster or group will usually contain individuals with a wide range of diagnoses. Further, because a particular therapy is recommended for a patient when that patient's quantified neurophysiologic data is in or near the cluster or group, determined in a neurophysiologic data space, of individuals responsive to that therapy, typically therapies will be selected as efficacious for patients with diagnoses that are not yet part of locally approved clinical practice involving that therapy. In fact, such an outcome is most probable because the clinical trials used to establish efficacy have heretofore usually been carried out without observation and analysis of trial participants' quantified neurophysiologic information according to the present invention. In this manner, new efficacious uses of known therapies, in particular of known therapeutic entity are determined.

In addition, even if a therapeutic entity, or other therapy, is not yet present in a particular treatment-response database, previously described embodiments of the present invention may be applied to selected patients and diagnoses that will likely be responsive to this therapeutic entity. For example, a responsivity profile may be determined for the not-yet-present therapeutic entity (foreign to the database) and compared to responsivity profiles of therapeutic entities already present in the database (native to the database). The foreign therapeutic entity will likely be efficacious in the same situations, i.e., for the same patients and the same diagnoses, as is the native therapeutic entity. If no native therapeutic entity has a responsivity profile similar to the foreign therapeutic entity, the present invention may still indicate patients and diagnoses for which the foreign therapeutic entity is likely to be efficacious in the same manner as described in the previous particular embodiments which select patients for clinical trials. That is patients, along with their diagnoses, are indicated if their quantified neurophysiologic is close to being complementary to significant aspects of foreign therapeutic entities responsivity profile.

Further, therapeutic entities may be evaluated which are not traditionally considered for psychiatric therapies. For example, cardiac therapeutic entities which affect the electrophysiologic functioning of the heart are determined to be efficacious for patients with particular neurophysiologic or electrophysiologic profiles.

Determination of clusters or groups and similarity of quantified neurophysiologic information (including, preferably, QEEG data) preferably, is in a reduced space. In particular preferred embodiments, similarity and clustering are defined in a reduced binary space of QEEG data by rules involving multivariables and Boolean combinations of such rules. Fuzzy, or approximate, similarity or clustering is similarly defined by "fuzzy" Boolean functions. For example, a disjunction is true in a "fuzzy" sense if most of its terms are true (for example more than 50%, or 75%, or the like, are true). In this embodiment, individual and group diagnostic indications are expressed compactly as rules depending on quantitative EEG data, or other quantitative neurophysiologic data.

Moreover, this invention includes not only these described methods for determining new indications for therapeutic entities, but also includes the actual therapeutic uses of these therapeutic entities in indicated patients or in patients with the indicated diagnoses. In certain embodiments, indications for a therapy may include simply the presence of a behavioral diagnosis not heretofore associated or approved with the use of the particular therapy. In other embodiments, the indications may include quantified neurophysiologic criteria in place of or together diagnostic information, such as a diagnostic class or a particular diagnosis. Preferably, these indications depend on QEEG data, and most preferably are expressed in a reduced QEEG space, such as by rules in a binary reduced space.

TABLE 13 presents a non-exhaustive list of indications for therapeutic entities or for classes of therapeutic entities in particular behaviorally-diagnosed psychiatric conditions, or in classes or such conditions. Some indications (appropriately set out) are already believed to be known as part of approved clinical practice or under development for future approval. Further indications are (also appropriately set out) believed to be not currently known. Certain indications are believed not only not to be known, but also to be surprising in view of current scientific understanding. It is to be understood that the present invention covers individually all novel uses indicated in TABLE 13, whether or not novelty is correctly set out in this table. Thus, each entry in TABLE 13 not currently part of approved clinical practice (for example, as presented in the Physician's Desk Reference) is individually covered, and covered as part of a group, with such provisos as necessary to exclude uses which are not novel. The indications in TABLE 13 may be supplemented as a result of further applications of the methods of this invention.

TABLE 13

| | GABA | GLUTAMINE | PHENYLALANINE |
|---|---|---|---|
| 300.00 Anxiety Disorder NOS | N | N | N |
| 300.02 Generalized Anxiety Disorder | N | N | N |
| 300.22 Agoraphobia Without History of Panic Disorder | N | N | N |
| 300.23 Social Phobia | N | N | N |
| 300.29 Specific Phobia | N | N | N |
| 300.3 Obsessive-Compulsive Disorder | N | N | N |
| 309.81 Posttraumatic Stress Disorder | N | N | N |
| Panic Disorder | N | N | N |
| 299.00 Autistic Disorder | | N | N |

TABLE 13 containing a sample (additional data are attached in appendix 2 to this disclosure) with novel treatments indicated by a table entry of "N." Conventional treatment is indicated with an entry of "C" in the appropriate cell. The listings provided herein are not intended to be a limitation on the scope of the claimed invention. Instead it is an illustration of the utility of the invention. It also illustrates that many known agents are useful for treating traditionally diagnosed conditions. The failure to recognize such use is a reflection of limited screening methods available and the risks associated with them.

These individual diagnostic indications for use are, in preferred or particular embodiments, conditioned on neurophysiologic (QEEG) data. Such conditions are preferably expressed as rules relevant to each indication. A non-exhaustive list of such rules is presented in TABLE 6. Here, each row represents a rule formed by the (preferably fuzzy) disjunction of the multivariables in the indicated columns.

Further, these indications, although preferably applicable to patients with behaviorally-diagnosed psychiatric conditions, may also apply to presently asymptomatic patients that display QEEG data (or, generally, quantified neurophysiologic data) that is otherwise indicated for therapy. Such uses are referred to as "prophylactic."

Administration of therapy is generally done in formulations and dosages in accordance with known clinical and pharmaceutical guidelines. For existing therapeutic entities, already approved formulations may be used in therapeutically effective dosages.

In more detail, the present invention encompasses the following specific therapeutic aspects. The invention encompasses methods of establishing an indication for use of a therapeutic agent in treating patients having a behaviorally diagnosed psychiatric disorder, wherein said agent has not heretofore been indicated for treatment of said disorder in approved clinical practice, the method comprising: indicating said agent for treatment of said disorder where quantified neurophysiologic data obtained from one or more patients having said condition indicates that said agent has been therapeutic effective in reference patients, whether or not the reference patients have been diagnosed with said disorder. These methods includes treating a patient having a behaviorally diagnosed psychiatric disorder other than an a disorder already approved for such therapy, and treating patients with particular indicated diagnoses.

The invention further encompasses methods of recommending treatment for a patient having a behaviorally diagnosed psychiatric disorder, comprising: indicating one or more therapeutic agents in dependence on quantified neurophysiologic information obtained from said patient, wherein the therapeutic agents are indicated independently of the identity of said disorder, and recommending one of more of the indicated therapeutic agents. The quantified information may include neurophysiologic information, neuro-electrophysiologic information, neuro-electro-physiologic information obtained from said patient in a resting, un-stimulated condition, and may exclude patients with observable systemic metabolic or anatomic pathology.

The invention further encompasses methods recommending treatment for a patient having a behaviorally diagnosed psychiatric disorder, comprising: indicating therapeutic agents by comparing quantified neurophysiologic information obtained from the patient with quantified neurophysiologic information obtained from individuals in one or more reference populations of individuals, wherein the information from at least one reference population includes treatment modalities for individuals with behaviorally diagnosed psychiatric disorders, and recommending one or more of the indicated therapeutic agents. The invention further includes methods of recommending treatment for a patient having a behaviorally diagnosed psychiatric disorder, comprising: determining the effects of one or more therapeutic agents on quantified neurophysiologic information obtained from individuals in one or more reference populations of individuals, and recommending one or more therapeutic agents in dependence on a comparison of quantified neurophysiologic information obtained from said patient with said determined effects of one or more therapeutic agents, wherein therapeutic agents are recommended independently of the identity of said disorder; as well as methods for correlating patients with therapeutic agents, wherein said patients have behaviorally diagnosed psychiatric disorders, the method comprising: for each said patient and each said agent, determining a level of correlation between said patient and said agent by: indicating a relatively high level of correlation between said patient and said agent if quantified neurophysiologic information obtained from said patient compares "closely" with quantified neurophysiologic information obtained from at least one reference individual of one or more reference populations of individuals, wherein the information from at least one reference population includes treatment modalities for individuals, and wherein information for at least one treatment modality for said reference individual indicates said reference individual was relatively effectively treated with said agent, and indicating a relatively low level of correlation between said patient and said agent if quantified neurophysiologic information obtained from said patient compares "closely" with quantified neurophysiologic information obtained from at least one reference individual of one or more reference populations of individuals, and wherein information for at least one treatment modality for said reference individual indicates said reference individual was relatively ineffectively treated with said agent.

The invention may also be described by way of many embodiments encompassed by it.

The invention encompasses a method for identifying an outcome of a first treatment based on neurophysiologic information from a subject independent of a behavioral mental disease diagnosis of or behavioral data from the subject, the method comprising the steps of: scaling the neurophysiologic information to enable comparison with stored neurophysiologic information obtained from a data source; computing at least one indicative variable from the neurophysiologic information; and evaluating the at least one indicative variable with aid of at least one rule to predict the outcome of the first treatment prior to actually administering the first treatment. Optionally, the threshold number is 80% whereby 80% of subjects having a common response to the first treatment are included in the cluster. Optionally, neurophysiologic information comprises electroencephalogram recordings recorded by electrodes placed in accordance with the International 10/20 system.

Optionally, the method for identifying an outcome of a first treatment based on neurophysiologic information from a subject independent of a behavioral mental disease diagnosis of or behavioral data from the subject further includes identifying the at least one indicative variable by screening a response database comprising pre-treatment neurophysiologic information and response to the first treatment in the form of active-treatment neurophysiologic information from a plurality of subjects.

Optionally, the method for identifying an outcome of a first treatment based on neurophysiologic information from a subject independent of a behavioral mental disease diagnosis of or behavioral data from the subject further includes identifying clusters of pre-treatment neurophysiologic information associated with subjects having similar responses to the first treatment as part of the screening step.

Optionally, the method for identifying an outcome of a first treatment based on neurophysiologic information from a subject independent of a behavioral mental disease diagnosis of or behavioral data from the subject further includes identifying a cluster by identifying a region in a multidimensional space defined by a range of values of unitary variables such that a threshold number of subjects having a common response to the first treatment are included in the region; and identifying the range of values of unitary variables describing the region.

Optionally, the method for identifying an outcome of a first treatment based on neurophysiologic information from a subject independent of a behavioral mental disease diagnosis of or behavioral data from the subject further includes combining the set of unitary variables having values shared by subjects within a cluster to form a multivariable and employing the multivariable as the at least one indicative variable.

Optionally, each of the similar responses is a clinical global improvement score selected from the set consisting of an integer in the range [−1 to 3] such that '−1' indicates adverse therapeutic entity effect, '0' indicates no improvement, '1' indicates minimal improvement, '2' indicates moderate improvement and '3' indicates complete absence of symptoms. Optionally, each of the similar responses is a measure of the difference between the active-treatment neurophysiologic information and a distribution of neurophysiologic information of age-matched reference subjects.

Optionally, the method for identifying an outcome of a first treatment based on neurophysiologic information from a subject independent of a behavioral mental disease diagnosis of or behavioral data from the subject further includes including the outcome of the first treatment in a report.

Optionally, the method for identifying an outcome of a first treatment based on neurophysiologic information from a subject independent of a behavioral mental disease diagnosis of or behavioral data from the subject further includes applying a plurality of rules associated with a plurality of indicative variables to the neurological information from a first data source; evaluating whether the rules indicate substantial agreement with one of a plurality of outcomes following the first treatment; and including, in response to such an indication, the one of a plurality of outcomes following the first treatment in a report.

Optionally, the first treatment is specified in response to a traditional diagnosis of mental disease. Optionally, the first treatment is in a list of treatments specified in response to the traditional diagnosis of mental disease whereby effective treatments in the list are rapidly identified.

Optionally, the method for identifying an outcome of a first treatment based on neurophysiologic information from a subject independent of a behavioral mental disease diagnosis of or behavioral data from the subject further includes comparing a result of applying at least one rule to the neurological information from the subject to at least one expected result associated with a second treatment, the second treatment not in the list of treatments based on the neurological information from the subject; and identifying, in response to detecting a similarity between the at least one expected result and the result, the second treatment as a possible treatment in a report.

Optionally, the traditional diagnosis is major depressive disorder and the second treatment is selected from the group consisting of glutamine, phenylalanine, and tyrosine, or the traditional diagnosis is psychological factors affecting medical condition, atypical asthma and the second treatment is selected from the group consisting of glutamine, phenylalanine, tyrosine, bupropion, pa mate, moclobemide, phenalzine, seligeline, venlafaxine, carbamazepine, gabapentin, lamotrigine, ginko biloba, dexedrine, methapmphetamine, methylphenidate, and pemoline.

Optionally, the traditional diagnosis may be one of anxiety disorders and the second treatment is selected from the group consisting of gaba, glutamine, phenylalanine, tyrosine, buproprion, citalopram, fluvoxamine, citalopramine, clomipramine, moclobemide, parnate, phenalzine, seligeline, carbamazepine, divalproex, gabapentin, lamotrigine, guanfacine hcl, clonidine, atenolol, metopolol, propranolol, lithium, ginko biloba, kava kava, st. john's wort, amantadine, phototherapy at 10000 lux, adderall, dexedrine, methapmphetamine, methylphenidate, modafinil, and pemoline.

Optionally, the traditional diagnosis may be one of psychological factors affecting medical condition, disorders usually first diagnosed in infancy, childhood, or adolescence and the second treatment is selected from the group consisting of gaba glutamine, phenylalanine, tyrosine, donepezil, buproprion, citalopram, clomiprimine, doxepin, fluoxetine, fluvoxamine, moclobemide, pamate, phenalzine, seligeline, trazodone, venlafaxine, carbamazepine, diphenylhydantoin, divalproex, gabapentin, lamotrigine, guanfacine hcl, clorazepate, diazapam, oxazepam, quazepam, atenolol, metopolol, propranolol, lithium, ginko biloba, kava kava, st. john's wort, silbtrimin, amantadine, phototherapy at 10000 lux, adderall, dexedrine, methapmphetamine, methylphenidate, modafinil, and phentermine.

Optionally, the traditional diagnosis may be one of eating disorders and the second treatment is selected from the group consisting of gaba, glutamine, phenylalanine, tyrosine, donepezil, buproprion, moclobemide, pamate, phenalzine, seligeline, venlafaxine, carbarniazapine, diphenylhydantoin, divalproex, gabapentin, lamotrigine, diazapam, lorazepam, atenolol, metopolol, propranolol, lithium, ginko biloba, kava kava, st. john's wort, amantadine, phototherapy at 10000 lux, zolipidem, adderall, dexedrine, methapmphetamine, methylphenidate, modafinil, pemoline, and phentermine.

Optionally, the traditional diagnosis may be one of delirium, dementia and amnestic and other cognitive disorders and the second treatment is selected from the group consisting of glutamine, phenylalanine, tyrosine, donepezil, amitriptyline, buproprion, fluxotine, moclobemide, pamate, phenalzine, seligeline, venlafaxine, carbamazepine, divalproex, gabapentin, lamotrigine, atenolol, metopolol, propranolol, lithium, ginko biloba, silbtrimin, amantadine, phototherapy at 10000 lux, zolipidem, adderall, dexedrine, methapmphetamine, methylphenidate, modafinil, pemoline, and phentermine.

Optionally, the traditional diagnosis may be impulse control disorders not elsewhere classified and the second treatment is selected from the group consisting of glutamine, phenylalanine, tyrosine, donepezil, buproprion, citalopram, clomiprimine, desipramine, moclobemide, nefazodone, parnate, phenalzine, seligeline, venlafaxine, carbamazepine, diphenylhydantoin, divalproex, gabapentin, lamotrigine, guanfacine hcl, clonidine, atenolol, metopolol, propranolol, ginko biloba, kava kava, silbtrimin, amantadine, phototherapy at 10000 lux, adderall, dexedrine, methapmphetamine, methylphenidate, and pemoline.

Optionally, the traditional diagnosis may be one of mood disorders and the second treatment is selected from the group consisting of glutamine, phenylalanine, tyrosine, moclobemide, parnate, phenalzine, seligeline, diphenylhydantoin, lamotrigine, guanfacine hcl, clonidine, lorazepam, oxazepam, quazepam, temazepam, trizolam, atenolol, metopolol, propranolol, ginko biloba, kava kava, st. john's wort, phototherapy at 10000 lux, adderall, dexedrine, methapmphetamine, methylphenidate, pemoline, and phentermine.

Optionally, the traditional diagnosis may be one of other codes and conditions and the second treatment is selected from the group consisting of gaba, glutamine, phenylalanine, tyrosine, donepezil, buproprion, citalopram, clomiprimine, fluvoxamine, moclobemide, notriptyline, parnate, phenalzine, seligeline, trazodone, venlafaxine, carbamazepine, divalproex, gabapentin, lamotrigine, guanfacine hcl, clonidine, atenolol, metopolol, propranolol, ginko biloba, kava kava, st. john's wort, amantadine, phototherapy at 10000 lux, zolipidem, adderall, dexedrine, methapmphetamine, methylphenidate, pemoline, and phentermine.

Optionally, the traditional diagnosis may be one of personality disorders and the second treatment is selected from the group consisting of gaba, glutamine, phenylalanine, tyrosine, donepezil, buproprion, moclobemide, parnate, phenalzine, seligeline, venlafaxine, carbamazepine, diphenylhydantoin, divalproex, gabapentin, lamotrigine, diazapam, atenolol, metopolol, propranolol, lithium, ginko biloba, kava kava, st. john's wort, phototherapy at 10000 lux, adderall, dexedrine, methapmphetamine, methylphenidate, pemoline, and phentermine.

Optionally, the traditional diagnosis may be hypoactive sexual desire disorder and the second treatment is selected from the group consisting of buproprion, buspirone, moclobemide, parnate, phenalzine, and seligeline.

Optionally, the traditional diagnosis may be one of sleep disorders and the second treatment is selected from the group consisting of gaba, glutamine, phenylalanine, tyrosine, donepezil, buproprion, buspirone, citalopram, clomiprimine, desipramine, fluoxetine, fluvoxamine, moclobemide, parnate, phenalzine, seligeline, sertraline, venlafaxine, carbamazapine, diphenylhydantoin, divalproex, gabapentin, lamotrigine, guanfacine hcl, clonidine, atenolol, metopolol, propranolol, lithium, ginko biloba, kava kava, st. john's wort, silbtrimin, phototherapy at 10000 lux, adderall, dexedrine, methapmphetamine, methylphenidate, pemoline, and phentermine.

Optionally, the traditional diagnosis may be one of somatoform disorders and the second treatment is selected from the group consisting of gaba, glutamine, phenylalanine, tyrosine, donepezil, buproprion, citalopram, fluvoxamine, moclobemide, parnate, phenalzine, seligeline, carbamazepine, diphenylhydantoin, divalproex, gabapentin, lamotrigine, atenolol, metopolol, propranolol, ginko biloba, kava kava, st. john's wort, amantadine, phototherapy at 10000 lux, zolipidem, adderall, dexedrine, methapmphetamine, methylphenidate, modafinil, pemoline, and phentermine.

Optionally, the traditional diagnosis may be one of substance-related disorders and the second treatment is selected from the group consisting of gaba, glutamine, phenylalanine, tyrosine, donepezil, fluvoxamine, moclobemide, parnate, phenalzine, seligeline, venlafaxine, carbamazapine, diphenylhydantoin, divalproex, gabapentin, lamotrigine, guanfacine hcl, atenolol, metopolol, propranolol, ginko biloba, kava kava, st. john's wort, silbtrimin, phototherapy at 10000 lux, adderall, dexedrine, methapmphetamine, methylphenidate, and pemoline.

Optionally, the first treatment in the list of treatments is identified as unlikely to result in a favorable outcome. Optionally, the method for identifying an outcome of a first treatment based on neurophysiologic information from a subject independent of a behavioral mental disease diagnosis of or behavioral data from the subject further includes displaying additional treatments, based on the neurophysiologic information from the subject, for obtaining the desired response.

Optionally, the method for identifying an outcome of a first treatment based on neurophysiologic information from a subject independent of a behavioral mental disease diagnosis of or behavioral data from the subject further includes transmitting neurophysiologic information, over a communication link, to a remote site for analysis; and receiving a response thereto. Optionally, the response is provided within a time interval suitable for concurrent examination of a subject and treatment.

The invention also encompasses a method for identifying a treatment for a subject based on pretreatment neurophysiologic information from the subject and a desired outcome, the method comprising the steps of: scaling the pretreatment neurophysiologic information to enable comparison with stored neurophysiologic information obtained from a data source; constructing clusters of pretreatment neurophysiologic information in a treatment-response database comprising pre-treatment neurophysiologic information and associated response score and active-treatment neurophysiologic information for each of a plurality of subjects by considering pretreatment neurophysiologic information associated with the desired outcome; identifying at least one cluster to which the pretreatment neurophysiologic information of the subject belongs, the at least one cluster defining a range of neurophysiologic information; and identifying at least one treatment associated with the at least one cluster. Optionally, neurophysiologic information comprises electroencephalogram recordings recorded by electrodes placed in accordance with the International 10/20 system.

Optionally, the method for identifying a treatment for a subject based on pretreatment neurophysiologic information from the subject and a desired outcome further includes listing treatments associated with the at least one cluster.

Optionally, the method for identifying a treatment for a subject based on pretreatment neurophysiologic information from the subject and a desired outcome further includes listing treatments associated with each cluster to which the pretreatment neurophysiologic information of the subject belongs.

Optionally, the method for identifying a treatment for a subject based on pretreatment neurophysiologic information from the subject and a desired outcome further includes specifying at least one cluster-defining rule. Optionally, the at least one cluster-defining rule specifies that each cluster, associated with at least one treatment, includes at least 80% of subjects having pretreatment neurological information associated with the desired outcome. Optionally, the at least one cluster-defining rule further specifies that preferably no more than 10%, even more preferably 15%, and most preferably 20% of subjects having pretreatment neurophysiologic information within bounds of each cluster, associated with at least one treatment, are associated with a treatment different than that associated with the each cluster. Optionally, the at least one cluster-defining rule further specifies that false positives do not exceed a threshold Optionally, the method for identifying a treatment for a subject based on pretreatment neurophysiologic information from the subject and a desired outcome further includes receiving pretreatment neurophysiologic information from a remote location over a communication link.

Optionally, the method for identifying a treatment for a subject based on pretreatment neurophysiologic information from the subject and a desired outcome further includes sending a message disclosing the at least one treatment over a communication link to a remote location.

Optionally, the method for identifying a treatment for a subject based on pretreatment neurophysiologic information from the subject and a desired outcome further includes screening a plurality of subjects having respective pre-treatment neurophysiologic information in the same cluster for a common genetic determinant. Optionally, at least some of the plurality of subjects are related genetically by membership in a family-tree spanning at least two generations and no more than twenty generations.

The invention also encompasses a method of building a treatment-response database to facilitate predicting treatments having a desirable outcome, avoiding ineffective or harmful treatments, and defining treatment-based conditions, the method comprising the steps of: storing initial neurophysiologic information associated with a subject in association with a treatment administered to the subject, a active-treatment neurophysiologic information associated with the subject and a magnitude-outcome of the treatment associated with the subject, the magnitude-outcome reflecting the extent of change rather than change in a particular feature whereby effect of the treatment on different mental diseases having various distinct features can be compared; and obtaining such information from at least a specified number of subjects.

Optionally, the method of building a treatment-response database to facilitate predicting treatments having a desirable outcome, avoiding ineffective or harmful treatments, and defining treatment-based conditions further includes computing the magnitude-outcome of the treatment associated with the subject to the treatment by comparing the active-treatment neurophysiologic information to the initial neurophysiologic information associated with the subject.

Optionally, the initial neurophysiologic information is pretreatment neurophysiologic information corresponding to a treatment-free state of the subject. Optionally, the treatment-free state of the subject requires that the subject not be administered the treatment for a prior time duration of at least seven and a half half-lives of the treatment whereby eliminating prior effects of the treatment.

Optionally, the method of building a treatment-response database to facilitate predicting treatments having a desirable outcome, avoiding ineffective or harmful treatments, and defining treatment-based conditions further includes entering, in the treatment-response database, an identifier for a cluster of initial neurophysiologic information whereby enabling subsequent searching of the treatment-response database for at least one cluster of initial neurophysiologic information similar to a query initial neurophysiologic information.

Optionally, the method of building a treatment-response database to facilitate predicting treatments having a desirable outcome, avoiding ineffective or harmful treatments, and defining treatment-based conditions further includes identifying an initial neurophysiologic profile in a neurophysiologic information entry; identifying a treatment administered to a subject associated with the neurophysiologic information entry; and identifying a magnitude-outcome of the treatment corresponding to the subject associated with the neurophysiologic information entry whereby adding a neurophysiologic information entry of a new subject to the treatment-response database.

Optionally, the method of building a treatment-response database to facilitate predicting treatments having a desirable outcome, avoiding ineffective or harmful treatments, and defining treatment-based conditions further includes determining whether a subject associated with the neurophysiologic entry satisfies a threshold criterion.

The invention also encompasses a treatment-response database comprising: initial neurophysiologic information for each of a plurality of subjects; treatment information for the each of a plurality of subjects; and indicator of clinical treatment outcome for the each of a plurality of subjects. Optionally, the plurality of subjects number at least one hundred subjects.

Optionally, the treatment-response database further includes an identifier associated with at least one cluster of pretreatment neurophysiologic information wherein the at least one cluster includes pretreatment neurophysiologic information from subjects having similar responses to a treatment.

The invention also encompasses a method for identifying a condition for which a treatment is available, the method comprising the steps of: obtaining initial neurophysiologic information from a plurality of subjects; obtaining active-treatment neurophysiologic information for the plurality of subjects following administration to each of the plurality of subjects a treatment; obtaining an outcome for each of the plurality of subjects following the treatment; clustering initial neurophysiologic information from subjects exhibiting a desirable outcome following the treatment to obtain at least one cluster, wherein a cluster is bounded by values of neurophysiologic information; and identifying a range of values of neurophysiologic information defining the at least one cluster as a condition precedent to be satisfied by a new initial neurophysiologic information of a new subject prior to administration of the treatment.

Optionally, the method for identifying a condition for which a treatment is available further includes specifying a threshold for defining a cluster. Optionally, the at least one cluster has no more than a threshold fraction of false positives whereby limiting subjects having initial neurophysiologic information falling within the at least one cluster although the subjects do not exhibit the desirable outcome following the treatment.

Optionally, the method for identifying a condition for which a treatment is available further includes identifying the range of values of neurophysiologic information as a condition responsive to the treatment.

Optionally, the method for identifying a condition for which a treatment is available further includes diagnosing a new subject as afflicted with the condition responsive to the treatment based on an initial neurophysiologic information of the new subject falling within the at least one cluster.

Optionally, the method for identifying a condition for which a treatment is available further includes estimating the fraction of the plurality of subjects having initial neurophysiologic information falling within the at least one cluster to estimate the number of people in the United States that are responsive to the treatment. Optionally, estimating includes employing a sampling frequency associated with the plurality of subjects. Optionally, the method further includes determining whether the number of people in the United States that are responsive to the treatment is less than a qualifying threshold. Optionally, the qualifying threshold is 200,000.

The invention also encompasses a method for estimating a function of a therapeutic entity on a subject of interest, the method comprising the steps of: receiving a neurophysiologic information of the subject; identifying clusters of neurophysiologic information, each of the clusters defined by a range of values for neurophysiologic information, in a treatment-response database comprising neurophysiologic information and the effect of treatments thereon, such that the neurophysiologic information of the subject satisfies respective ranges of the identified clusters; identifying treatments associated with the identified clusters; determining whether any of the treatments is similar to an administration of the therapeutic entity; and inferring the function of the therapeutic entity based on the function of the identified treatments.

Optionally, the method for estimating a function of a therapeutic entity on a subject of interest further includes inferring lack of a desirable effect of the therapeutic entity on the subject in response to a failure to identify a treatment similar to the therapeutic entity in clusters additionally associated with the desirable effect in the treatment-response database.

Optionally, the method for estimating a function of a therapeutic entity on a subject of interest further includes transmitting neurophysiologic information to a remote site for analysis; and receiving a response thereto.

The invention also encompasses a method for reevaluating therapeutic entity testing data, that does not reveal a desired effect of a therapeutic entity on subjects, to identify at least one condition for using the therapeutic entity on at least one subset of subjects, the method comprising the steps of: identifying subjects having initial neurophysiologic information and a desired response to the therapeutic entity in the therapeutic entity testing data; clustering initial neurophysiologic information corresponding to the subjects having a desirable response to administration of the therapeutic entity; identifying at least one cluster that satisfies at least one of the set consisting of a prescribed threshold; identifying a range of a parameter defining the at least one cluster; and specifying the range of the parameter as a condition for pre-screening subjects for administration of the therapeutic entity whereby ensuring that subjects for administering the therapeutic entity also have neurophysiologic information belonging to the at least one cluster.

Optionally, the prescribed threshold is selected from the set consisting of a number of false positives, a number of false negatives, and a ratio of false positives to false negatives. Optionally, the therapeutic entity is known to be safe in humans. Optionally, the therapeutic entity is known to have at least one known use. Optionally, the therapeutic entity testing data relates to identifying additional applications of the therapeutic entity.

Optionally, the method for reevaluating therapeutic entity testing data, that does not reveal a desired effect of a therapeutic entity on subjects, to identify at least one condition for using the therapeutic entity on at least one subset of subjects further includes estimating the at least one subset of subjects as a fraction of the subjects to estimate the number of people in a jurisdiction that are responsive to the treatment. Optionally, estimating includes employing a sampling frequency associated with the plurality of subjects.

Optionally, the method for reevaluating therapeutic entity testing data, that does not reveal a desired effect of a therapeutic entity on subjects, to identify at least one condition for using the therapeutic entity on at least one subset of subjects further includes determining whether the number of people in the United States that are responsive to the treatment is less than a qualifying threshold. Optionally, the qualifying threshold is 200,000.

The invention also encompasses a method for generating rules for predicting suitability of a treatment for a subject based on the subject's neurophysiologic information as opposed to a traditional diagnosis of a mental disorder, the method comprising the steps of: clustering initial neurophysiologic information from a plurality of subjects such that each cluster is associated with at least one treatment outcome; evaluating neurophysiologic information in a cluster to determine at least one feature of the neurophysiologic information that is common to the cluster; and generating a rule based on the at least one feature to determine whether a new initial neurophysiologic information from a new subject belongs to the cluster whereby predicting the same outcome for the treatment as that associated with the cluster.

Optionally, neurophysiologic information is collected using a neurophysiologic technique selected from the set consisting of electroencephalograhy, evoked potentials, event-related potentials, direct electrode recordings, magnetic resonance imaging, positron emission tomography, single photon emission computerized tomography, electromagnetocephalography and any combination thereof. Optionally, the neurophysiologic information is in the form of unitary variables that define a multidimensional space such that a cluster occupies a contiguous region defined by values of unitary variables therein.

Optionally, the method for generating rules for predicting suitability of a treatment for a subject based on the subject's neurophysiologic information as opposed to a traditional diagnosis of a mental disorder further includes describing the cluster by the feature comprising at least one of the multivariables from the set consisting of EEG absolute power average, Frontal Midline Progression Index, Posterior Midline Progression Index, Ratio of Frontal/Posterior Alpha Indices, Average Midline Theta/Beta ratio, RMAD, RMPD, RMAT, RMPT, RMAA, RMPA, RMAB, RMPB, CEAD, CEPD, CEAT, CEPT, CEAA, CEPA, CEAB, CEPB, FMAD, FMPD, FMAT, FMPT, FMAA, FMPA, FMAB, FMPB, AADL, AADR, AATL, AATR, AAAL, AAAR, AABL, AABR, AED, AET, AEA, AEB, AEBD, AEBT, AEBA, AEBB, CADL, CADR, CATL, CATR, CAAL, CAAR, CABL, CABR, CEBD, CEBT, CEBA, CEBB, RBDL, RBDR, RBTL, RBTR, RBAL, RBAR, RBBL, and RBBR.

Optionally, the method for generating rules for predicting suitability of a treatment for a subject based on the subject's neurophysiologic information as opposed to a traditional diagnosis of a mental disorder further includes describing the cluster by specifying a range for each of the features: EEG absolute power average, Posterior Midline Progression Index, Ratio of Frontal/Posterior Alpha Indices, Average Midline Theta/Beta ratio, RMAB, RMPB, CEAA, CEPA, CEAB, CEPB, FMAA, FMPA, FMAB, FMPB, CAAL, CAAR, CABL, CABR, CEBA, and CEBB.

Optionally, the method for generating rules for predicting suitability of a treatment for a subject based on the subject's neurophysiologic information as opposed to a traditional diagnosis of a mental disorder further includes identifying the new initial neurophysiologic information from the new subject as belonging to the cluster in response to determining a substantial correlation between the new initial neurophysiologic information and ranges for the features describing the cluster.

The invention also encompasses a method of using a treatment-response database comprising a treatment, initial neurophysiologic information, active-treatment neurophysiologic information and an outcome of the treatment, the method comprising the steps of: converting into univariate measures; extracting multivariables of interest from the univariate measures; and storing multivariables in the treatment-response database whereby facilitating subsequent database searches.

The invention also encompasses a portable device for evaluating and suggesting a treatment, the device comprising: an input module for receiving neurophysiologic information from a subject; a rule module for providing rules for a specific variables in the neurophysiologic information; a correspondence module to detect a match between a result of applying rules to variables in the neurophysiologic information and the expected result for a treatment; and an output module for indicating an outcome for at least one treatment.

Optionally, the neurophysiologic information comprises a plurality of univariate variables and the specific variable includes at least one univariate variable. Optionally, the portable device further includes at least one reference distribution for scaling the neurophysiologic information with respect thereto. Optionally, the portable device further includes a treatment-response database to facilitate predicting treatments having a desirable outcome, avoiding ineffective or harmful treatments, and defining treatment-based conditions by undertaking reanalysis of data therein.

The invention also encompasses a method of establishing an approved use of a therapeutic agent in treating patients having a disorder, wherein said agent has not heretofore been approved for treatment of said disorder in approved clinical practice, the method comprising: indicating said agent for treatment of said disorder where neurophysiologic information obtained from one or more patients having said condition indicates that said agent has therapeutic effectiveness in reference patients, whether or not the reference patients have been diagnosed with said disorder.

Optionally, the method further includes administering a therapeutically effective amount of said indicated agent to one or more patients, and verifying that said agent is effective in at least one patient. Optionally, the method further includes administering a therapeutically effective amount of an agent indicated by the method of claim 87 to be effective in treating patients with said disorder. The method includes scenarios wherein said behaviorally diagnosed disorder is anorexia nervosa, bulimia nervosa, or other eating disorder, and wherein said agent is selected from the group consisting of methylphenidate and dextroamphetamine. The method also includes scenarios of treating a patient having a behaviorally diagnosed psychiatric disorder other than an attention-deficit/hyperactivity disorder, comprising: administering a therapeutically effective dose of methylphenidate.

The invention encompasses a method of treating a patient having behaviorally diagnosed anorexia nervosa, bulimia nervosa, or other eating disorder, comprising: administering a therapeutically effective amount of a drug selected from the group consisting of methylphenidate and dextroamphetamine.

The invention also encompasses a method of recommending treatment for a patient having a behaviorally diagnosed psychiatric disorder, comprising: indicating one or more therapeutic agents in dependence on neurophysiologic information obtained from said patient, wherein the therapeutic agents are indicated independently of the identity of said disorder, and recommending one of more of the indicated therapeutic agents wherein said patient is without externally observable anatomic pathology.

Optionally, the indicated one or more therapeutic agents comprise agents from a single class of agents, wherein a class of agents comprises agents with similar physiological effects on a target organ system. Optionally, the class of agents is selected from the group consisting of class 1 agents, class 2 agents, class 3 agents, class 4 agents, and class 5 agents.

The method also encompasses treating a patient having a behaviorally diagnosed psychiatric disorder, comprising: administering one or more recommended therapeutic agents.

The invention also encompasses a method of recommending treatment for a patient having a behaviorally diagnosed psychiatric disorder, comprising: indicating therapeutic agents by comparing quantified neurophysiologic information obtained from the patient with quantified neurophysiologic information obtained from individuals in one or more reference populations of individuals, wherein the information from at least one reference population includes treatment modalities for individuals with behaviorally diagnosed psychiatric disorders, and recommending one or more of the indicated therapeutic agents.

Optionally, the method includes administering one or more recommended therapeutic agents. Optionally, the method includes scenarios wherein the behavioral diagnosis comprises a diagnosis made according to professionally accepted psychiatric criteria.

The invention also encompasses a method of recommending treatment for a patient having a behaviorally diagnosed psychiatric disorder, comprising: determining the effects of one or more therapeutic agents on quantified neurophysiologic information obtained from individuals in one or more reference populations of individuals, and recommending one or more therapeutic agents independence on a comparison of quantified neurophysiologic information obtained from said patient with said determined effects of one or more therapeutic agents, wherein therapeutic agents are recommended independently of the identity of said disorder.

Optionally, the comparison indicates a therapeutic agent if the determined effects of said agent substantially correct abnormalities in said neurophysiologic information obtained from said patient. Optionally, the method for treating a patient having a behaviorally diagnosed psychiatric disorder, includes administering one or more recommended therapeutic agents.

The invention also encompasses a method of correlating patient with therapeutic agents, wherein said patients have behaviorally diagnosed psychiatric disorders, the method comprising: for each said patient and each said agent, determining a level of correlation between said patient and said agent by indicating a relatively high level of correlation between said patient and said agent if quantified neurophysiologic information obtained from said patient correlates with quantified neurophysiologic information obtained from at least one reference individual of one or more reference populations of individuals, wherein the information from at least one reference population includes treatment modalities for individuals, and wherein information for at least one treatment modality for said reference individual indicates said reference individual was relatively effectively treated with said agent, and indicating a relatively low level of correlation between said patient and said agent if quantified neurophysiologic information obtained from said patient correlates with quantified neurophysiologic information obtained from at least one reference individual of one or more reference populations of individuals, and wherein information for at least one treatment modality for said reference individual indicates said reference individual was relatively ineffectively treated with said agent.

Optionally, the invention encompasses a method of recommending treatment for a patient having a behaviorally diagnosed psychiatric disorder includes recommending agents correlated with said patient in accordance with the method of correlating patient with therapeutic agents.

Optionally, the invention encompasses a method of recommending a patient for a trial of a therapeutic agent-in-trial includes recommending patients correlated with at least one similar therapeutic agent according to the method of correlating patient with therapeutic agents, and wherein an agent is similar to said agent-in-trial if the effects of said agent and said agent-in-trial on quantified neurophysiologic information obtained from individuals in one or more reference populations of individuals compares closely.

The invention also encompasses a method for classifying physiologic brain imbalances, comprising: comparing quantified neurophysiologic information from a patient with neurophysiologic information from a reference population of individuals to produce a group of differences for the patient, organizing said differences by neurophysiologic output measurements to provide a differences profile of the physiological state of the patient's brain function, comparing said differences profile of the patient with neurophysiologic information from a second reference population who are symptomatic for physiologic brain imbalances to produce a group of similarities for the patient, organizing said similarities by neurophysiologic output measurements to provide a similarities profile of the physiological state of the patient's brain function, correlating said similarities profile of the patient with a series of treatment modalities for the second reference group to produce a treatment recommendation.

Optionally, the treatment modality is drug therapy, and wherein the drug is selected from the group consisting of alprazolam, amantadine, amitriptyline, atenolol, bethanechol, bupropion, buspirone, carbamazepine, chlorpromazine, chlordiazepoxide, citalopram, clomipramine, clonidine, clonazepam, clozapine, cyproheptadine, dexamethasone, divalproex, deprenyl, desipramine, dexamethasone, dextroamphetamine, diazepam, disulfram, divalproex, doxepin, ethchlorvynol, fluoxetine, fluvoxamine, felbamate, fluphenazine, gabapentin, haloperidol, imipramine, isocarboxazid, lamotrigine, levothyroxine, liothyronine, lithium carbonate, lithium citrate, lorazepam, loxapine, maprotiline, meprobamate, mesoridazine, methamphetamine, midazolam, meprobamate, mirtazapine, molindone, moclobemide, molindone, naltrexone, phenelzine, nefazodone, nortriptyline, olanzapine, oxazepam, paroxetine, pemoline, perphenazine, phenelzine, pimozide, pindolol, prazepam, propranolol, protriptyline, quetiapine, reboxetine, risperidone, selegiline, sertraline, sertindole, trifluoperazine, trimipramine, temazepam, thioridazine, topiramate, tranylcypromine, trazodone, triazolam, trihexyphenidyl, trimipramine, valproic acid, venlafaxine, and any combination thereof.

Optionally, the physiologic brain imbalance accompanies panic disorder and the treatment modality is drug therapy using a drug selected from the group consisting of valproic acid, clonazepam, carbamazepine, methylphenidate and dextroamphetamine.

Optionally, the physiologic brain imbalance accompanies eating disorder and the treatment modality is drug therapy using a drug selected from the group consisting of methylphenidate and dextroamphetamine.

Optionally, the physiologic brain imbalance accompanies learning disorder and the treatment modality is drug therapy using a drug selected from the group consisting of amantadine, valproic acid, clonazepam and carbamazepine.

Optionally, the method includes obtaining follow-up neurophysiologic information to track physiologic changes produced by the administration of treatment modalities, and making therapy regime changes based on the follow-up neurophysiologic information and a patient assessment tool.

Optionally, the method includes scenarios wherein the physiologic brain imbalance is associated with behaviorally or non-behaviorally diagnosed brain pathologies.

Optionally, the method includes scenarios wherein the brain pathology is selected from the group consisting of agitation, Attention Deficit Hyperactivity Imbalance, Abuse, Alzheimer's disease/dementia, anxiety, panic, and phobic disorders, bipolar disorder, borderline personality disorder, behavior control problems, body dysmorphic disorders, cognitive problems, Creutzfeldt-Jakob disease, depression, dissociative disorders, eating, appetite, and weight problems, edema, fatigue, hiccups, impulse-control problems, irritability, jet lag, mood problems, movement problems, obsessive-compulsive disorder, pain, personality imbalances, posttraumatic stress disorder, schizophrenia and other psychotic disorder, seasonal affective disorder, sexual disorder, sleep disorder, stuttering, substance abuse, tic disorder/Tourette's Syndrome, traumatic brain injury, Trichotillomania, Parkinson's disease, violent/self-destructive behaviors, and any combination thereof.

The invention encompasses a method for classifying physiologic brain imbalances, comprising: comparing quantified neurophysiologic information from a patient with neurophysiologic information from a reference population of individuals to produce a group of differences for the patient, and organizing the differences by neurophysiologic output measurements to provide a differences profile of the physiological state of the patient's brain function.

Optionally the method for classifying physiologic brain imbalances includes scenarios wherein the quantified neurophysiologic information is fast Fourier transform quantitative electroencephalography.

Optionally the method for classifying physiologic brain imbalances includes scenarios wherein the quantified neurophysiologic information is nonparoxysmal.

Optionally the method for classifying physiologic brain imbalances includes scenarios wherein the quantified neurophysiologic information is at least in part paroxysmal.

Optionally the method for classifying physiologic brain imbalances includes scenarios wherein the neurophysiologic information is general or FFT quantitative electroencephalography (QEEG) information.

Optionally the method for classifying physiologic brain imbalances includes scenarios wherein the quantified neurophysiologic information from a patient and from a reference population is general or FFT QEEG multivariate output measurements.

Optionally the method for classifying physiologic brain imbalances includes scenarios wherein the general or FFT QEEG multivariate output measurements are selected from a group consisting of absolute power, relative power, frequency, intrahemispheric coherence, interhemispheric coherence, intrahemispheric asymmetry, and interhemispheric asymmetry, and ratios or combinations thereof.

Optionally the method for classifying physiologic brain imbalances includes scenarios wherein the general or FFT QEEG multivariate output measurements are determined from combinations of EEG electrodes found in the anterior, posterior, right hemisphere, left hemisphere regions of the scalp.

Optionally the method for classifying physiologic brain imbalances includes scenarios wherein the general or FFT QEEG multivariate output measurements are determined from electrodes or combinations of electrodes in the delta, theta, alpha, or beta EEG frequency bands.

Optionally the method for classifying physiologic brain imbalances includes scenarios wherein Z scores are determined for each general or FFT QEEG multivariate output measurement.

Optionally the method for classifying physiologic brain imbalances includes scenarios wherein the general or FFT QEEG multivariate output measurements are expressed in terms of Z scores.

Optionally the method for classifying physiologic brain imbalances includes scenarios wherein the reference population is drawn from individuals who are asymptomatic for physiologic brain imbalances.

Optionally, the invention also encompasses a method for treating physiologic brain imbalances of a patient, comprising correlating the differences profile of the patient according to the method for classifying physiologic brain imbalances with a series of treatment modalities to produce a treatment recommendation.

The invention also encompasses a method for analyzing physiologic brain imbalances of a patient, comprising: comparing the differences profile of the patient according to claim 104 with neurophysiologic information from a second reference population of individuals who are symptomatic for physiologic brain imbalances to produce a group of similarities for the patient; and organizing the similarities by neurophysiologic output measurements to provide a similarities profile of the physiological state of the patient's brain function.

Optionally, the invention also encompasses a method for treating physiologic brain imbalances of a patient, comprising: correlating the similarities profile of the patient according to the method for analyzing physiologic brain imbalances of a patient with a series of treatment modalities for the second reference group to produce a treatment recommendation.

The invention also encompasses a method for analyzing physiologic brain imbalances of a patient, comprising: comparing quantified neurophysiologic information from the patient with neurophysiologic information from a reference population of individuals who are symptomatic for physiologic brain imbalances to produce a group of similarities for the patient, and organizing the similarities by neurophysiologic output measurements to provide a similarities profile of the physiological state of the patient's brain function.

Optionally, the method for analyzing physiologic brain imbalances of a patient includes scenarios wherein the symptomatic patients from whom the neurophysical output measurements are collected exhibit behavioral indicia of physiologic brain imbalances.

Optionally, the method for analyzing physiologic brain imbalances of a patient includes scenarios wherein the symptomatic patients from whom the neurophysiologic output measurements are collected exhibit non-behavioral indicia of physiologic brain imbalances.

The invention also encompasses a method for treating physiologic brain imbalances of a patient, comprising: correlating the similarities profile of the patient according to the method for analyzing physiologic brain imbalances of a patient with a series of treatment modalities for the reference group to produce a treatment recommendation.

The invention also encompasses a method for classifying physiologic brain imbalances, comprising: comparing quantified neurophysiologic information from a patient with neurophysiologic information from a reference population of individuals to produce a group of differences for the patient; and organizing the differences by neurophysiologic output measurements to provide a differences profile of the physiological state of the patient's brain function.

The invention also encompasses a method for analyzing physiologic brain imbalances of a patient, comprising: comparing the differences profile of the patient with neurophysiologic information from a second reference population who are symptomatic for physiologic brain imbalances to produce a group of similarities for the patient; and organizing the similarities by neurophysiologic output measurements to provide a similarities profile of the physiological state of the patient's brain function.

The invention also encompasses a method for treating the analyzed physiologic brain imbalances of a patient, comprising correlating the similarities profile of the patient with a series of treatment modalities for the second reference group to produce a treatment recommendation.

The invention also encompasses a method wherein the analyzed physiologic brain imbalance is associated with behaviorally or non-behaviorally diagnosed brain pathologies. Optionally, the brain pathology is selected from the group consisting of agitation, Attention Deficit Hyperactivity Imbalance, Abuse, Alzheimer's disease/dementia, anxiety, panic, and phobic disorders, bipolar disorder, borderline personality disorder, behavior control problems, body dysmorphic disorders, cognitive problems, Creutzfeldt-Jakob disease, depression, dissociative disorders, eating, appetite, and weight problems, edema, fatigue, hiccups, impulse-control problems, irritability, jet lag, mood problems, movement problems, obsessive-compulsive disorder, pain, personality imbalances, posttraumatic stress disorder, schizophrenia and other psychotic disorder, seasonal affective disorder, sexual disorder, sleep disorder, stuttering, substance abuse, tic disorder/Tourette's Syndrome, traumatic brain injury, Trichotillomania, Parkinson's disease, violent/self-destructive behaviors, and any combination thereof.

The invention also encompasses a method wherein the treatment modality is selected from the group consisting of drug therapy, electroconvulsive therapy, electromagnetic therapy, neuromodulation therapy, talk therapy, and any combination thereof. Optionally, the treatment modality is drug therapy and the drug is selected from the group consisting of a psychotropic agent, a neurotropic agent, a multiple of a phychotropic agent or a neurotropic agent, and any combination thereof. Optionally, the drug has a direct or indirect effect on the CNS system of the patient. And, optionally, the drug is selected from the group consisting of alprazolam, amantadine, amitriptyline, atenolol, bethanechol, bupropion, buspirone, carbamazepine, chlorpromazine, chlordiazepoxide, citalopram, clomipramine, clonidine, clonazepam, clozapine, cyproheptadine, dexamethasone, divalproex, deprenyl, desipramine, dexamethasone, dextroamphetamine, diazepam, disulfram, divalproex, doxepin, ethchlorvynol, fluoxetine, fluvoxamine, felbamate, fluphenazine, gabapentin, haloperidol, imipramine, isocarboxazid, lamotrigine, levothyroxine, liothyronine, lithium carbonate, lithium citrate, lorazepam, loxapine, maprotiline, meprobamate, mesoridazine, methamphetamine, midazolam, meprobamate, mirtazapine, molindone, moclobemide, molindone, naltrexone, phenelzine, nefazodone, nortriptyline, olanzapine, oxazepam, paroxetine, pemoline, perphenazine, phenelzine, pimozide, pindolol, prazepam, propranolol, protriptyline, quetiapine, reboxetine, risperidone, selegiline, sertraline, sertindole, trifluoperazine, trimipramine, temazepam, thioridazine, topiramate, tranylcypromine, trazodone, triazolam, trihexyphenidyl, trimipramine, valproic acid, venlafaxine, and any combination thereof.

Optionally, the method for classifying physiologic brain imbalances includes obtaining follow-up quantified neurophysiologic information to track physiologic changes produced by the administration of treatment modalities; and making therapy regime changes based on the follow-up neurophysiologic information and a patient assessment tool.

Optionally, the method for classifying physiologic brain imbalances includes scenarios wherein the physiologic brain imbalance accompanies panic disorder and the treatment modality is drug therapy using a drug selected from the group consisting of valproic acid, clonazepam, carbamazepine, methylphenidate and dextroamphetamine.

Optionally, the method for classifying physiologic brain imbalances includes scenarios wherein the physiologic brain imbalance accompanies eating disorder and the treatment modality is drug therapy using a drug selected from the group consisting of methylphenidate and dextroamphetamine.

Optionally, the method for classifying physiologic brain imbalances includes scenarios wherein the physiologic brain imbalance accompanies learning disorder and the treatment modality is drug therapy using a drug selected from the group consisting of amantadine, valproic acid, clonazepam and carbamazepine.

The invention also encompasses a method for the classification, diagnosis, and treatment of a physiologic brain imbalance of a patient at a remote location, comprising: sending the neurophysiologic information of the patient from the remote location to a central processing location, comparing the sent information at the central processing location with multivariate neurophysiologic output measurements collected from a reference population of individuals to obtain a brain profile, associating at the central processing location the brain profile to brain profiles indicative of brain pathologies to produce an association, and sending to the remote location a treatment recommendation based on the association.

The invention also encompasses a method suitable for determining the effect of a new or known drug on the CNS system of a patient, comprising: selecting at least one patient, administering the drug to the patient, obtaining the patient's post administration, neurophysiologic information, and analyzing the patient's post administration, neurophysiologic information to determine the effect of the drug on the CNS system of the patient.

The method suitable for determining the effect of a new or known drug on the CNS system of a patient includes scenarios wherein analyzing step includes comparing the patient's neurophysiologic information with neurophysiologic information obtained from a reference population of individuals to produce a similarities profile for the patient. Optionally, the similarities profile is used to determine the effect of the drug.

The method suitable for determining the effect of a new or known drug on the CNS system of a patient includes scenarios wherein pre-administration neurophysiologic information is obtained from the patient. Optionally, the pre-administration neurophysiologic information is also compared to the neurophysiologic information from the reference population. Optionally, the effect of the drug on the patient is determined by comparison of the pre and post administration sets of neurophysiologic information from the patient.

The invention also encompasses a method for screening individual participants for inclusion in clinical drug trials for treating physiologic brain imbalances, comprising: determining whether a potential individual participant exhibits a behavioral pathology, determining whether that potential individual participant has abnormal neurophysiologic information, and establishing a set of individual participants from those potential individual participants exhibiting a behavioral pathology and an abnormal neurophysiologic information associated with the behavioral pathology.

The method for screening individual participants for inclusion in clinical drug trials for treating physiologic brain imbalances includes scenarios wherein the drug undergoing clinical testing is a new compound or the drug undergoing clinical testing is a known compound for which a new use is indicated.

The invention also encompasses a method for treating physiologic brain imbalances, comprising: obtaining neurophysiologic information from a patient, quantifying the neurophysiologic information, and correlating the neurophysiologic information to therapy responsivity profiles.

Optionally, the method for treating physiologic brain imbalances further includes determining from the therapy responsivity profile a treatment of the physiologic brain imbalance of the patient.

Optionally, the method for treating physiologic brain imbalances further includes scenarios wherein the neurophysiologic information is collected using a neurophysiologic technique selected from the group consisting of electroencephalograhy, magnetic resonance imaging, positron emission tomography, single photon emission computerized tomography, and any combination thereof. Optionally, the neurophysiologic technique is electroencephalography. Optionally, the electroencephalography is digitized fast Fourier transform quantitative electroencephalography. Optionally, the neurophysiologic information is stored in a database. Optionally, the correlations between neurophysiologic information and therapy responsivity profiles are stored in a database.

The invention also encompasses a method of prescribing multiple treatments to a subject with the aid of a treatment-response database, the method comprising the steps of: obtaining neurophysiologic information from the subject; identifying at least one treatment option with the aid of the treatment-response database; selecting a first treatment, in response to identification of multiple treatment options, one treatment; administering the first treatment to the subject; adjusting the first treatment in accordance with an effect of the treatment on neurophysiologic information of the subject; and selecting a second treatment in accordance with an effect of the treatment on neurophysiologic information of the subject. Optionally, the method includes selecting, in response to a choice between class 4 agents and other agents, a treatment including at least one of class 4 agents. Optionally, the method includes selecting, in response to a choice between class 2 agents and other agents, a treatment including at least one of other agents. Optionally, the method includes Optionally, the method includes selecting, in response to a choice between class 1 agents and class 5 agents, a treatment including at least one of class 1 agents. Optionally, the treatment-response database is represented by a set of rules representing cluster boundaries for identifying at least one suitable treatment.

The invention also encompasses a method of generating a report reflecting a prospective estimate of a response to a treatment, the method comprising the steps of: reporting a class of an agent along with specific agents within the class such that the specific agents are indicated for a treatment of a subject based on a neurophysiologic information of the subject and a treatment-response database; ordering multiple classes in order of significance; representing responsivity to at least one treatment in the report by a responsivity code; and ordering multiple agents in order of the responsivity code. Optionally, the responsivity code is color coded for easy identification. Optionally, the responsivity code includes a plurality of levels representing a range of responses in the interval defined by a positive response and resistance to treatment. Optionally, the interval includes adverse responses to treatment. Optionally, the report includes an effect of a particular treatment on neurophysiologic information of the subject. Optionally, the report includes identification of less expensive treatments than a specified treatment such that the less expensive treatments prospectively have a substantially similar response as the specified treatment. Optionally, the report includes ordered treatments ordered in accordance with a cost of each of the ordered treatments. Optionally, the report is presented via an electronic user-interface. Optionally, the report is generated in response to an electronic request.

The invention also encompasses a method of establishing an approved use of a therapeutic agent in treating patients having a disorder, said agent has not heretofore been approved for treatment of said disorder in approved clinical practice, the method comprising: indicating said agent for treatment of said disorder where EEG information obtained from one or more patients having said condition indicates that said agent has therapeutic effectiveness in reference patients, whether or not the reference patients have been diagnosed with said disorder.

The invention also encompasses a method of processing data corresponding to neurophysiologic information; comprising: sending neurophysiologic information corresponding to one or more subjects to a processor, said processor configured to i) compare said information with neurophysiologic information from a reference population to produce a group of differences, and ii) organize said differences by output measurements to provide a differences profile, so as to create processed information. Optionally, the method further includes receiving said processed information. Optionally, the method further includes using said processed information to predict the outcome of treatment of said one or more subjects with one or more drugs prior to administering said one or more drugs. Optionally, the method further includes using said processed information in the development of a drug to generate drug development information wherein drug development information includes, unless in the contrary is indicated, any type of information required by the FDA including data for proving safety/efficacy; labeling information, etc. Optionally, the method further includes submitting said drug development information to a government regulatory agency. Optionally, the method further includes marketing or selling a drug by associating said differences profile with said drug, wherein the term "associating" includes direct or indirect (e.g. commercial utility) associations). Optionally, the neurophysiologic information comprises electroencephalogram recordings recorded by electrodes placed in accordance with the International 10120 system. Optionally, the sending is performed over an electronic communications network, wherein electronic communications network includes any transmission system including Internet, telephone, satellite, etc. Optionally, the sending is performed over the Internet or over telephone or by satellite transmission. Optionally, sending is performed at a first site and the processor is located at a second site, possibly with the sites in different countries. Optionally, receiving comprises accessing said processed information from a data storage sire, wherein said data storage site comprises a third site.

Similarly, the invention also encompasses a method of receiving processed information corresponding to neurophysiologic information; comprising: receiving processed neurophysiologic information from a processor, said processor having i) compared neurophysiologic information corresponding to one or more subjects with neurophysiologic information from a reference population to produce a group of differences, and ii) organized said differences by output measurements to provide a differences profile, so as to create processed information.

It is to be understood that the present invention also encompasses methods for remote performance of all the prior methods along with systems for remotely performing these prior methods (as illustrated in FIG. 15). The following embodiments are illustrative of such further methods and systems. In the interest of compactness without limitation, remote processing embodiments and systems corresponding to the other such methods and systems have been omitted.

The invention also encompasses a method for identifying a treatment for a subject based on pretreatment neurophysiologic information from the subject and a desired outcome, the method comprising the steps of: transmitting information from a first site, the transmitted information comprising the pretreatment neurophysiologic information and the desired outcome; and receiving information at a second site, wherein the received information comprising an indication of at least one treatment that was determined by the method of claim 29 from the transmitted information.

Optionally, in the prior method, the information is transmitted to and received from a processing site performing the method of claim 29; where the processing site is remotely located from the first and the second site; or where the processing site is colocated with the first or with the second site; or the first and the second site are colocated; or the second site are remotely located.

Optionally the prior method further comprises transmitting at least part of the received and at least part of the transmitted information to a reviewing site; and reviewing the quality of the transmitted information in view of the received information.

The invention also encompasses a system for identifying a treatment for a subject based on pretreatment neurophysiologic information from the subject and a desired outcome, the method comprising: a transmitting device at a first site, for transmitting information comprising the pretreatment neurophysiologic information and the desired outcome; and a receiving device at a second site, for receiving information comprising an indication of at least one treatment that was determined by the method of claim 29 from the transmitted information.

Finally, the invention also encompasses program products comprising a computer-readable medium having encoded instructions for causing a computer system to perform any or all of the methods of present invention.

Although the preceding description of the invention is in the context of the embodiments described herein, the embodiments are not intended to be a limitation on the scope of the invention. As readily recognized by one of ordinary skill in the art, the disclosed invention encompasses the disclosed embodiments along with other embodiments providing variations on choice of indicative and univariate variables, reference distributions, clustering strategies, software and remote treatment implementations and the like without departing from the form and spirit of the teaching disclosed herein.

APPENDIX I

| rEEG PARAMETERS | EEG ABSOLUTE POWER AVERAGE = >300 microvolts squared | EEG ABSOLUTE POWER AVERAGE = <300 & >40 microvolts sq. | EEG ABSOLUTE POWER AVERAGE = <40 microvolts squared | FRONTAL MIDLINE PROGRESSION INDEX Fpz/Cz (ALPHA BAND) = >2.5 | FRONTAL MIDLINE PROGRESSION INDEX Fpz/Cz (ALPHA BAND) = <2.5 | POSTERIOR MIDLINE PROGRESSION INDEX Oz/Cz (ALPHA BAND) = >1 | POSTERIOR MIDLINE PROGRESSION INDEX Oz/Cz (ALPHA BAND) = <1 |
|---|---|---|---|---|---|---|---|
| | BENZODIAZEPINE BETA BLOCKER WELLBUTRIN CARBAMAZEPINE CLONIDINE LITHIUM MAOI SNRI SSRI STIMULANT TCA VALPROATE PROZAC EFFEXOR LAMICTAL ADDERALL | CLONIDINE LITHIUM SNRI SSRI TCA PROZAC EFFEXOR | BENZODIAZEPINE BETA BLOCKER WELLBUTRIN CARBAMAZEPINE CLONIDINE LITHIUM MAOI SNRI SSRI STIMULANT TCA PROZAC EFFEXOR ADDERALL | MAOI STIMULANT LAMICTAL ADDERALL | WELLBUTRIN SNRI SSRI TCA PROZAC EFFEXOR | WELLBUTRIN SNRI SSRI TCA VALPROATE PROZAC EFFEXOR ADDERALL | BENZODIAZEPINE BETA BLOCKER WELLBUTRIN MAOI STIMULANT ADDERALL |

| rEEG PARAMETERS | RATIO OF FRONTAL/POSTERIOR ALPHA INDICES = >4 | RATIO OF FRONTAL/POSTERIOR ALPHA INDICES = <4 | AVERAGE MIDLINE (Fpz,Fz,Cz) THETA/BETA RATIO = >2.5 | AVERAGE MIDLINE (Fpz,Fz,Cz) THETA/BETA RATIO = <2.5 & >1.5 | AVERAGE MIDLINE (Fpz,Fz,Cz) THETA/BETA RATIO = <1.5 | RMAD = >10 +/− RMPD = >10 | RMAD = <10 +/− RMPD = <10 |
|---|---|---|---|---|---|---|---|
| | BENZODIAZEPINE BETA BLOCKER | BENZODIAZEPINE BETA BLOCKER | BENZODIAZEPINE BETA BLOCKER | | | | |

APPENDIX I-continued

| | | | | | | | |
|---|---|---|---|---|---|---|---|
| WELLBUTRIN CARBAMAZE-PINE CLONIDINE LITHIUM MAOI SNRI SSRI STIMULANT TCA VALPROATE PROZAC EFFEXOR LAMICTAL ADDERALL | SNRI SSRI TCA PROZAC EFFEXOR | WELLBUTRIN MAOI STIMULANT VALPROATE | WELLBUTRIN MAOI STIMULANT TCA ADDERALL | CARBAMAZE-PINE CLONIDINE SNRI SSRI TCA PROZAC EFFEXOR | CLONIDINE SNRI TCA PROZAC LAMICTAL | MAOI MAOI LAMICTAL | WELLBUTRIN CLONIDINE SNRI SSRI TCA PROZAC EFFEXOR |
| rEEG PARAMETERS | RMAT = >10 +/− RMPT = >10 | RMAT = <10 +/− RMPT = <10 | RMAA = >10 +/− RMPA = >10 | RMAA = <10 +/− RMPA = <10 | RMAB = >10 +/− RMPB = >10 | RMAB = <10 +/− RMPB = <10 | CEAD = >10 +/− CEPD = >10 |
| BENZO-DIAZEPINE BETA BLOCKER WELLBUTRIN CARBAMAZE-PINE CLONIDINE LITHIUM MAOI SNRI SSRI STIMULANT TCA VALPROATE PROZAC EFFEXOR LAMICTAL ADDERALL | BENZO-DIAZEPINE WELLBUTRIN MAOI STIMULANT LAMICTAL ADDERALL | CARBAMAZE-PINE SNRI SSRI TCA PROZAC EFFEXOR | WELLBUTRIN CARBAMAZE-PINE CLONIDINE SNRI SSRI TCA PROZAC EFFEXOR | BETA BLOCKER MAOI STIMULANT VALPROATE LAMICTAL ADDERALL | LITHIUM SNRI SSRI TCA VALPROATE PROZAC EFFEXOR ADDERALL | BENZO-DIAZEPINE WELLBUTRIN MAOI STIMULANT PROZAC EFFEXOR LAMICTAL ADDERALL | BENZO-DIAZEPINE VALPROATE LAMICTAL ADDERALL |
| rEEG PARAMETERS | CEAD = <10 +/− CEPD = <10 | CEAT = >10 +/− CEPT = >10 | CEAT = <10 +/− CEPT = <10 | CEAA = >10 +/− CEPA = >10 | CEAA = <10 +/− CEPA = <10 | CEAB = >10 +/− CEPB = >10 | CEAB =<10 +/− CEPB = <10 |
| BENZO-DIAZEPINE BETA BLOCKER WELLBUTRIN CARBAMAZE-PINE CLONIDINE LITHIUM MAOI SNRI SSRI STIMULANT TCA VALPROATE PROZAC EFFEXOR LAMICTAL ADDERALL | CARBAMAZE-PINE LITHIUM VALPROATE LAMICTAL ADDERALL | BENZO-DIAZEPINE VALPROATE | | CARBAMAZE-PINE LITHIUM | BETA BLOCKER CARBAMAZE-PINE LITHIUM SNRI SSRI TCA PROZAC EFFEXOR | BETA BLOCKER CARBAMAZE-PINE LITHIUM SNRI SSRI TCA VALPROATE PROZAC EFFEXOR | |
| rEEG PARAMETERS | FMAD = >10 +/− FMPD = >10 | FMAD = <10 +/− FMPD = <10 | FMAT = >10 +/− FMPT = >10 | FMAT = <10 +/− FMPT = <10 | FMAA = >10 +/− FMPA = >10 | FMAA = <10 +/− FMPA = <10 | FMAB = >10 +/− FMPB = >10 |
| BENZO-DIAZEPINE BETA BLOCKER WELLBUTRIN CARBAMAZE-PINE CLONIDINE LITHIUM MAOI SNRI | BENZO-DIAZEPINE MAOI SNRI | SNRI | BENZO-DIAZEPINE WELLBUTRIN MAOI | CARBAMAZE-PINE | BETA BLOCKER CARBAMAZE-PINE | BENZO-DIAZEPINE WELLBUTRIN MAOI SNRI | BETA BLOCKER CLONIDINE LITHIUM |

APPENDIX I-continued

| | | | | | | | | |
|---|---|---|---|---|---|---|---|---|
| SSRI<br>STIMULANT<br>TCA<br>VALPROATE<br>PROZAC<br>EFFEXOR<br>LAMICTAL<br>ADDERALL | STIMULANT<br><br><br><br><br><br>LAMICTAL<br>ADDERALL | SSRI<br><br>TCA | STIMULANT<br>TCA<br><br><br><br>LAMICTAL<br>ADDERALL | SSRI<br>TCA<br><br>PROZAC<br>EFFEXOR | SSRI<br>TCA<br><br>PROZAC | STIMULANT<br><br><br><br>EFFEXOR<br>LAMICTAL<br>ADDERALL | | PROZAC |

| rEEG PARAMETERS | FMAB = <10 +/−<br>FMPB = <10 | AADL = >10, OR<br>AADR = >10 | AADL = <10, OR<br>AADR = <10 | AATL = >10, OR<br>AATR = >10 | AATL = <10, OR<br>AATR = <10 | AAAL = >10, OR<br>AAAR = >10 | AAAL = <10, OR<br>AAAR = <10 |

| | | | | | | | |
|---|---|---|---|---|---|---|---|
| BENZO-<br>DIAZEPINE<br>BETA<br>BLOCKER<br>WELLBUTRIN<br>CARBAMAZE-<br>PINE<br>CLONIDINE<br>LITHIUM<br>MAOI<br>SNRI<br>SSRI<br>STIMULANT<br>TCA<br>VALPROATE<br>PROZAC<br>EFFEXOR<br>LAMICTAL<br>ADDERALL | BENZO-<br>DIAZEPINE<br><br><br>WELLBUTRIN<br><br><br><br><br>MAOI<br>SNRI<br>SSRI<br>STIMULANT<br><br>VALPROATE<br><br>EFFEXOR<br>LAMICTAL<br>ADDERALL | MAOI<br><br><br>STIMULANT | SNRI<br>SSRI<br><br>TCA | WELLBUTRIN<br><br><br><br><br>MAOI<br><br><br>STIMULANT | SNRI<br>SSRI<br><br>TCA | SNRI<br>SSRI<br><br>TCA<br><br>PROZAC<br>EFFEXOR | MAOI<br><br><br><br><br><br>CARBAMAZE-<br>PINE |

| rEEG PARAMETERS | AABL = >10, OR<br>AABR = >10 | AABL = <10, OR<br>AABR = <10 | AED = >10, &/OR<br>AED = <−10 | AET = >10, &/OR<br>AET = <−10 | AEA = >10, &/OR<br>AEA = <−10 | AEB = >10, &/OR<br>AEB = <−10 | AEBD = >10 &/OR<br>AEBD = <−10 |

| | | | | | | | |
|---|---|---|---|---|---|---|---|
| BENZO-<br>DIAZEPINE<br>BETA<br>BLOCKER<br>WELLBUTRIN<br>CARBAMAZE-<br>PINE<br>CLONIDINE<br>LITHIUM<br>MAOI<br>SNRI<br>SSRI<br>STIMULANT<br>TCA<br>VALPROATE<br>PROZAC<br>EFFEXOR<br>LAMICTAL<br>ADDERALL | <br><br><br><br>CARBAMAZE-<br>PINE<br><br><br><br>SNRI<br>SSRI<br><br>TCA<br><br>PROZAC<br>EFFEXOR | CARBAMAZE-<br>PINE | BENZO-<br>DIAZEPINE | BENZO-<br>DIAZEPINE | BENZO-<br>DIAZEPINE<br><br><br>CARBAMAZE-<br>PINE<br><br>LITHIUM | BENZO-<br>DIAZEPINE<br><br><br>CARBAMAZE-<br>PINE<br><br>LITHIUM<br><br><br><br><br><br>VALPROATE | BENZO-<br>DIAZEPINE<br><br><br><br><br><br>LITHIUM |

| rEEG PARAMETERS | AEBT = >10 &/OR<br>AEBT = <−10 | AEBA = >10 &/OR<br>AEBA = <−10 | AEBB = >10 &/OR<br>AEBB = <−10 | CADL = >10, OR = <−10 | CADR = >10, OR = <−10 | CATL = >10, OR = <−10 | CATR = >10, OR = <−10 |

| | | | | | | | |
|---|---|---|---|---|---|---|---|
| BENZO-<br>DIAZEPINE<br>BETA<br>BLOCKER<br>WELLBUTRIN<br>CARBAMAZE-<br>PINE<br>CLONIDINE<br>LITHIUM<br>MAOI<br>SNRI<br>SSRI<br>STIMULANT<br>TCA<br>VALPROATE<br>PROZAC<br>EFFEXOR | BENZO-<br>DIAZEPINE<br><br><br><br><br><br>LITHIUM<br><br><br><br><br><br><br>VALPROATE | BENZO-<br>DIAZEPINE<br><br><br><br><br><br>LITHIUM<br><br><br><br><br><br><br>VALPROATE | BENZO-<br>DIAZEPINE<br><br><br><br><br><br>LITHIUM<br><br><br><br><br><br><br>VALPROATE | BENZO-<br>DIAZEPINE<br><br><br><br><br><br><br><br><br><br><br><br><br>VALPROATE | BENZO-<br>DIAZEPINE<br><br><br><br><br><br><br><br><br><br><br><br><br>VALPROATE | BENZO-<br>DIAZEPINE<br><br><br><br><br><br><br><br><br><br><br><br><br>VALPROATE | BENZO-<br>DIAZEPINE<br><br><br><br><br><br><br><br><br><br><br><br><br>VALPROATE |

APPENDIX I-continued

| | | | | | LAMICTAL | LAMICTAL | LAMICTAL | LAMICTAL |
|---|---|---|---|---|---|---|---|---|
| LAMICTAL ADDERALL | | | | | | | | |

| rEEG PARAMETERS | CAAL = >10, OR = <−10 | CAAR = >10, OR = <−10 | CABL = >10, OR = <−10 | CABR = >10, OR = <−10 | CEBD = >10, OR = <−10 | CEBT = >10, OR = <−10 |
|---|---|---|---|---|---|---|
| BENZO-DIAZEPINE | | | | | BENZO-DIAZEPINE | BENZO-DIAZEPINE |
| BETA BLOCKER | BETA BLOCKER | BETA BLOCKER | BETA BLOCKER | BETA BLOCKER | | |
| WELLBUTRIN | | | | | | |
| CARBAMAZE-PINE | CARBAMAZE-PINE | CARBAMAZE-PINE | | | | |
| CLONIDINE | | | | | | |
| LITHIUM | | | | | | |
| MAOI | | | | | | |
| SNRI | | | | | | |
| SSRI | | | | | | |
| STIMULANT | | | | | | |
| TCA | | | | | | |
| VALPROATE | | | | | VALPROATE | VALPROATE | VALPROATE |
| PROZAC | PROZAC | PROZAC | PROZAC | PROZAC | | |
| EFFEXOR | EFFEXOR | EFFEXOR | EFFEXOR | EFFEXOR | | |
| LAMICTAL | LAMICTAL | LAMICTAL | | | | |
| ADDERALL | | | | | | |

| rEEG PARAMETERS | CEBA = >10, OR = <−10 | CEBB = >10, OR = <−10 | RBDL = >10, &/OR RBDR = >10 | RBDL = <10, &/OR RBDR = <10 | RBTL = >10, &/OR RBTR = >10 | RBTL = <10, &/OR RBTR = <10 |
|---|---|---|---|---|---|---|
| BENZO-DIAZEPINE | | | | | | |
| BETA BLOCKER | BETA BLOCKER | BETA BLOCKER | | | | |
| WELLBUTRIN | | | | | WELLBUTRIN | |
| CARBAMAZE-PINE | CARBAMAZE-PINE | | | | | |
| CLONIDINE | | | | | | |
| LITHIUM | | | | | | |
| MAOI | | | MAOI | | MAOI | |
| SNRI | | | | SNRI | | SNRI |
| SSRI | | | | SSRI | | SSRI |
| STIMULANT | | | STIMULANT | | STIMULANT | |
| TCA | | | | TCA | | TCA |
| VALPROATE | | VALPROATE | | | | |
| PROZAC | PROZAC | PROZAC | PROZAC | PROZAC | | |
| EFFEXOR | EFFEXOR | EFFEXOR | EFFEXOR | EFFEXOR | | |
| LAMICTAL | | | | | | |
| ADDERALL | | | ADDERALL | | ADDERALL | |

| rEEG PARAMETERS | RBAL = >10, &/OR RBAR = >10 | RBAL = <10, &/OR RBAR = <10 | RBBL = >10, &/OR RBBR = >10 | RBBL = <10, &/OR RBBR = <10 |
|---|---|---|---|---|
| BENZO-DIAZEPINE | | | | |
| BETA BLOCKER | | | | |
| WELLBUTRIN | | | | |
| CARBAMAZE-PINE | | | | |
| CLONIDINE | | | | |
| LITHIUM | | | LITHIUM | |
| MAOI | | MAOI | | MAOI |
| SNRI | SNRI | | SNRI | |
| SSRI | SSRI | | SSRI | |
| STIMULANT | | STIMULANT | | STIMULANT |
| TCA | TCA | | TCA | |
| VALPROATE | | | | |
| PROZAC | PROZAC | | PROZAC | |
| EFFEXOR | EFFEXOR | | EFFEXOR | |
| LAMICTAL | | | | |
| ADDERALL | | ADDERALL | | ADDERALL |

APPENDIX II

| | GABA 64 | GLUTA-MINE 67 | PHENYL-ALANINE 68 | TYRO-SINE 63 | AMITRIP-TYLINE 47 | BUPROPRION (LONG ACTING) 85 | BUPROPRION (REGULAR TABS) 87 | BUS-PIRONE 38 | CITALO-PRAM 82 |
|---|---|---|---|---|---|---|---|---|---|
| 300.00 Anxiety Disorder NOS | N | N | N | N | C | N | N | C | N |
| 300.02 Generalized Anxiety Disorder | N | N | N | N | | N | N | C | N |
| 300.22 Agoraphobia Without History of Panic Disorder | N | N | N | N | C | N | N | C | N |
| 300.23 Social Phobia | N | N | N | N | C | N | N | C | |
| 300.29 Specific Phobia | N | N | N | N | | N | N | C | |
| 300.3 Obsessive-Compulsive Disorder | N | N | N | N | | N | N | | |
| 309.81 Posttraumatic Stress Disorder | N | N | N | N | C | N | N | C | C |
| Panic Disorder | N | N | N | N | | N | N | C | C |
| 299.00 Autistic Disorder | | N | N | N | | | | | |
| 299.80 Pervasive Developmental Disorder NOS | | | | | | N | N | | |
| 307.20 Tic Disorder NOS | | | | | | | | | |
| 307.22 Chronic Motor or Vocal Tic Disorder | N | | | | | | | | |
| 307.23 Tourette's Disorder | | | | | | | | | |
| 307.9 Communication Disorder NOS | | | | | | N | N | | |
| 309.21 Separation Anxiety Disorder | N | N | N | N | | N | N | | N |
| 312.8 Conduct Disorder | | N | N | N | | N | N | | |
| 313.81 Oppositional Defiant Disorder | N | N | N | N | | N | N | | N |
| 315.9 Learning Disorder NOS | | N | N | N | | N | N | | |
| Attention-Deficit/Hyperactivity Disorder | | N | N | N | | N | N | | |
| 294.8 Amnestic Disorder | | N | N | N | | N | N | C | |
| 294.9 Cognitive Disorder NOS | | N | N | N | | N | N | | |
| Dementia of the Alzheimer's Type | | N | N | N | | | | | |
| 307.1 Anorexia Nervosa | N | N | N | N | C | N | N | C | C |
| 307.50 Eating Disorder NOS | N | N | N | N | | N | N | C | C |
| 307.51 Bulimia Nervosa | N | N | N | N | | N | N | C | C |
| 312.30 Impulse-Control Disorder NOS | | | | | | N | N | | |
| 312.31 Pathological Gambling | | | | | | N | N | | |
| 312.34 Intermittent Explosive Disorder | | N | N | N | | N | N | C | N |
| 312.39 Trichotillomania | | N | N | N | | N | N | C | |
| 296.89 Bipolar II Disorder | | N | N | N | | N | N | | |
| 296.90 Mood Disorder NOS | | N | N | N | C | C | C | | |
| 300.4 Dysthymic Disorder | | | | | C | C | C | C | C |
| 301.13 Cyclothymic Disorder | | N | N | N | | N | N | | |
| 311 Depressive Disorder NOS | | N | N | N | | N | N | | |
| Bipolar I Disorder | | | | | | N | N | | |
| Major Depressive Disorder, Recurrent | | N | N | N | C | C | C | | C |
| Major Depressive Disorder, Single Episode | | N | N | N | C | C | C | | C |
| 316 Psychological Factors Affecting Medical Condition, Irritable Bowel Syndrome | | | | | C | | | C | N |
| 316 Psychological Factors Affecting Medical Condition, Atypical Asthma | | N | N | N | | N | N | | |
| 316 Psychological Factors Affecting Medical Condition, Hypertensive Disorder NOS | | | | | | | | | |
| 316 Psychological Factors Affecting Medical Condition, Neurodermatitis | N | | | | C | N | N | C | N |
| 301.20 Schizoid Personality Disorder | | N | N | N | | N | N | | |
| 301.22 Schizotypal Personality Disorder | | N | N | N | | N | N | | |
| 301.4 Obsessive-Compulsive Personality Disorder | N | N | N | N | | N | N | | |
| 301.50 Histrionic Personality Disorder | | N | N | N | | N | N | C | |
| 301.6 Dependent Personality Disorder | | N | N | N | | N | N | | |

APPENDIX II-continued

| | | | | | | | | | |
|---|---|---|---|---|---|---|---|---|---|
| 301.7 Antisocial Personality Disorder | N | N | N | N | | N | N | | |
| 301.82 Avoidant Personality Disorder | N | N | N | N | | N | N | | |
| 301.83 Borderline Personality Disorder | N | N | N | N | | N | N | | |
| 302.71 Hypoactive Sexual Desire Disorder | | | | | | N | N | | |
| 307.42 Primary Insomnia | N | | | | C | N | N | N | N |
| 307.44 Hypersomnia related to . . . [Indicate the Axis I or Axis II Disorder] | | N | N | N | | N | N | | |
| 307.44 Primary Hypersomnia | | N | N | N | | N | N | | |
| 307.45 Circadian Rhythm Sleep Disorder | N | | | | C | N | N | | |
| 307.47 Dyssomnia NOS | N | | | | C | N | N | N | N |
| 307.47 Parasomnia NOS | | | | | C | N | N | | N |
| 780.59 Breathing-Related Sleep Disorder | | N | N | N | | N | N | | |
| 300.7 Body Dysmorphic Disorder | N | N | N | N | | N | N | | |
| 300.7 Hypochondriasis | | N | N | N | | N | N | | N |
| 300.81 Somatization Disorder | N | N | N | N | C | N | N | C | |
| 300.81 Somatoform Disorder NOS | N | N | N | N | | N | N | C | |
| Pain Disorder 307.89 Pain Associated With Both Psychological Factors and a General Medical Condition | | | | | C | N | N | | N |
| Alcohol Abuse & Dependence | N | N | N | N | C | N | N | C | C |
| Amphetamine Abuse & Dependence | | N | N | N | C | N | N | C | C |
| Cannabis Abuse & Dependence | N | N | N | N | | N | N | | |
| Cocaine Abuse & Dependence | | N | N | N | | N | N | | |
| Inhalant Abuse & Dependence | | | | | | | | | |
| Nicotine Dependence | | N | N | N | | C | C | | |
| Opioid Abuse & Dependence | | | | | | N | N | | |
| Sedative, Hypnotic or Anxiolytic Abuse & Dependence | N | N | N | N | C | N | N | | N |

| | CLOMIP-RAMINE 42 | DESIP-RAMINE 25 | DOXEPIN 24 | FLUOX-ETINE 15 | FLUVOX-AMINE 69 | IMIP-RAMINE 6 | MIRTA-ZAPINE 77 | MOCLOB-EMIDE 72 | NEFA-ZODONE 54 |
|---|---|---|---|---|---|---|---|---|---|
| 300.00 Anxiety Disorder NOS | C | C | C | C | N | C | | N | N |
| 300.02 Generalized Anxiety Disorder | | | C | C | | C | | N | |
| 300.22 Agoraphobia Without History of Panic Disorder | | N | | C | N | N | | N | |
| 300.23 Social Phobia | | C | C | C | | | | N | |
| 300.29 Specific Phobia | | C | C | C | | | | N | |
| 300.3 Obsessive-Compulsive Disorder | C | | | C | C | | | N | |
| 309.81 Posttraumatic Stress Disorder | | C | C | C | C | C | | N | |
| Panic Disorder | | C | C | C | C | C | | N | |
| 299.00 Autistic Disorder | | | | | | | | | |
| 299.80 Pervasive Developmental Disorder NOS | | N | | N | N | C | | N | |
| 307.20 Tic Disorder NOS | | N | | | | C | | | |
| 307.22 Chronic Motor or Vocal Tic Disorder | | N | | | N | | | | |
| 307.23 Tourette's Disorder | | N | | | | | | | |
| 307.9 Communication Disorder NOS | | | | | | | | | |
| 309.21 Separation Anxiety Disorder | | C | | N | | C | | N | |
| 312.8 Conduct Disorder | | | | N | | C | | N | |
| 313.81 Oppositional Defiant Disorder | | C | | N | | C | | N | |
| 315.9 Learning Disorder NOS | | N | | N | | C | | N | |
| Attention-Deficit/Hyperactivity Disorder | | C | | N | | C | | N | |
| 294.8 Amnestic Disorder | | | | | | | | N | |
| 294.9 Cognitive Disorder NOS | | | | | | | | | |

APPENDIX II-continued

| Disorder | 1 | 2 | 3 | 4 | 5 | 6 | 7 | 8 | 9 |
|---|---|---|---|---|---|---|---|---|---|
| Dementia of the Alzheimer's Type | | | | | | | | | |
| 307.1 Anorexia Nervosa | C | C | C | C | C | C | C | N | C |
| 307.50 Eating Disorder NOS | N | N | C | C | C | C | C | N | |
| 307.51 Bulimia Nervosa | N | N | C | C | C | C | C | N | C |
| 312.30 Impulse-Control Disorder NOS | | | C | | | | | N | |
| 312.31 Pathological Gambling | | | C | C | C | | | N | |
| 312.34 Intermittent Explosive Disorder | | N | C | N | | C | | N | N |
| 312.39 Trichotillomania | | | C | C | | C | | N | |
| 296.89 Bipolar II Disorder | | N | | N | N | | C | N | |
| 296.90 Mood Disorder NOS | | C | C | C | N | C | C | N | C |
| 300.4 Dysthymic Disorder | C | C | C | C | C | C | C | N | C |
| 301.13 Cyclothymic Disorder | | | | N | N | | | N | |
| 311 Depressive Disorder NOS | | | C | N | | C | C | N | C |
| Bipolar I Disorder | | N | | N | N | | | N | C |
| Major Depressive Disorder, Recurrent | | C | C | C | N | C | C | N | C |
| Major Depressive Disorder, Single Episode | | C | C | C | N | C | C | N | C |
| 316 Psychological Factors Affecting Medical Condition, Irritable Bowel Syndrome | N | | C | C | | C | | N | |
| 316 Psychological Factors Affecting Medical Condition, Atypical Asthma | | | | | | | | N | |
| 316 PsychologIcal Factors Affecting Medical Condition, Hypertensive Disorder NOS | | | C | N | | | | N | |
| 316 Psychological Factors Affecting Medical Condition, Neurodermatitis | N | C | C | N | N | N | | N | |
| 301.20 Schizoid Personality Disorder | | C | | N | | | | N | |
| 301.22 Schizotypal Personality Disorder | | C | | | | | | | |
| 301.4 Obsessive-Compulsive Personality Disorder | C | | | C | C | | | N | |
| 301.50 Histrionic Personality Disorder | | | C | | | | | N | |
| 301.6 Dependent Personality Disorder | | N | | N | | | | N | |
| 301.7 Antisocial Personality Disorder | | C | C | | | C | | N | |
| 301.82 Avoidant Personality Disorder | | N | | N | | C | | N | |
| 301.83 Borderline Personality Disorder | | N | C | C | | | | N | |
| 302.71 Hypoactive Sexual Desire Disorder | | | | | | | | N | |
| 307.42 Primary insomnia | N | | C | N | N | C | | N | |
| 307.44 Hypersomnia related to . . . [Indicate the Axis I or Axis II Disorder] | | | | | | | | N | |
| 307.44 Primary Hypersomnia | | | | | | | | N | |
| 307.45 Circadian Rhythm Sleep Disorder | | | C | | N | | | N | |
| 307.47 Dyssomnia NOS | | | C | N | | | C | N | |
| 307.47 Parasomnia NOS | | | | N | | | C | N | |
| 780.59 Breathing-Related Sleep Disorder | | N | | | | | | N | |
| 300.7 Body Dysmorphic Disorder | C | | | C | N | | | N | |
| 300.7 Hypochondriasis | | | C | C | N | | | N | |
| 300.81 Somatization Disorder | | C | C | C | | | | N | |
| 300.81 Somatoform Disorder NOS | | C | C | C | | | | N | |
| Pain Disorder 307.89 Pain Associated With Both Psychological Factors and a General Medical Condition | | C | C | C | | C | | N | |
| Alcohol Abuse & Dependence | C | C | C | N | N | C | | N | C |
| Amphetamine Abuse & Dependence | | C | C | C | | C | | N | |
| Cannabis Abuse & Dependence | | N | | N | N | | | N | |
| Cocaine Abuse & Dependence | | | | | | | | | |

APPENDIX II-continued

| | NOR-TRIP-TYLINE 30 | PAR-NATE 41 | PAROX-ETINE 9 | PHENAL-ZINE 48 | SELIG-ELINE 83 | SERTRA-LINE 12 | TRAZO-DONE 18 | VENLA-FAXINE 8 | VENLA-FAXINE TABLETS 93 | CARBA-MAZE-PINE 7 |
|---|---|---|---|---|---|---|---|---|---|---|
| Inhalant Abuse & Dependence | | | | | | | | | | |
| Nicotine Dependence | | | | | | | | | N | |
| Opioid Abuse & Dependence | | | | | | | | | N | |
| Sedative, Hypnotic or Anxiolytic Abuse & Dependence | C | C | C | C | N | C | | | N | |

| | NOR-TRIP-TYLINE 30 | PAR-NATE 41 | PAROX-ETINE 9 | PHENAL-ZINE 48 | SELIG-ELINE 83 | SERTRA-LINE 12 | TRAZO-DONE 18 | VENLA-FAXINE 8 | VENLA-FAXINE TABLETS 93 | CARBA-MAZE-PINE 7 |
|---|---|---|---|---|---|---|---|---|---|---|
| 300.00 Anxiety Disorder NOS | | N | C | N | N | C | C | N | N | N |
| 300.02 Generalized Anxiety Disorder | C | N | C | | | | C | C | C | |
| 300.22 Agoraphobia Without History of Panic Disorder | C | N | C | N | N | C | | N | N | N |
| 300.23 Social Phobia | C | N | C | N | N | C | C | N | N | N |
| 300.29 Specific Phobia | C | N | C | N | N | C | C | N | N | N |
| 300.3 Obsessive-Compulsive Disorder | | N | | N | N | N | | N | N | N |
| 309.81 Posttraumatic Stress Disorder | C | N | C | N | N | C | C | N | N | N |
| Panic Disorder | C | N | C | N | N | C | C | N | N | N |
| 299.00 Autistic Disorder | | | | | | | | | | N |
| 299.80 Pervasive Developmental Disorder NOS | | N | | N | N | | | | | N |
| 307.20 Tic Disorder NOS | | | | | | | | | | N |
| 307.22 Chronic Motor or Vocal Tic Disorder | | | | | | | | | | N |
| 307.23 Tourette's Disorder | | | | | | | | | | N |
| 307.9 Communication Disorder NOS | | | | | | | | | N | N |
| 309.21 Separation Anxiety Disorder | C | N | C | N | N | N | | N | N | N |
| 312.8 Conduct Disorder | C | N | | N | N | N | | N | N | N |
| 313.81 Oppositional Defiant Disorder | N | N | N | N | N | N | | N | N | N |
| 315.9 Learning Disorder NOS | C | N | | N | | | | N | N | N |
| Attention-Deficit/Hyperactivity Disorder | C | N | | N | | | | N | N | N |
| 294.8 Amnestic Disorder | | | | | | | | | | |
| 294.9 Cognitive Disorder NOS | | N | | N | N | | | N | N | N |
| Dementia of the Alzheimer's Type | | | | | | | | | | |
| 307.1 Anorexia Nervosa | C | N | C | N | N | C | C | N | N | N |
| 307.50 Eating Disorder NOS | C | N | C | N | N | C | C | N | N | N |
| 307.51 Bulimia Nervosa | | N | C | N | N | C | C | N | N | N |
| 312.30 Impulse-Control Disorder NOS | | N | | | | | | | | |
| 312.31 Pathological Gambling | | N | C | N | N | C | C | N | N | N |
| 312.34 Intermittent Explosive Disorder | C | N | | N | N | | | N | N | N |
| 312.39 Trichotillomania | | N | C | N | N | C | | | | N |
| 296.89 Bipolar II Disorder | N | N | N | N | N | | | N | N | C |
| 296.90 Mood Disorder NOS | C | N | C | N | N | C | C | C | C | N |
| 300.4 Dysthymic Disorder | C | N | C | N | N | C | C | C | C | N |
| 301.13 Cyclothymic Disorder | | N | | N | N | N | | N | N | N |
| 311 Depressive Disorder NOS | | N | | N | N | | | N | N | N |
| Bipolar I Disorder | N | N | N | N | N | | | N | N | C |
| Major Depressive Disorder, Recurrent | C | N | C | N | N | C | C | C | C | N |
| Major Depressive Disorder, Single Episode | C | N | C | N | N | C | C | C | C | N |
| 316 Psychological Factors Affecting Medical Condition, Irritable Bowel Syndrome | | | C | | | C | | N | N | N |
| 316 Psychological Factors Affecting Medical Condition, Atypical Asthma | | N | | N | N | | | N | N | N |
| 316 Psychological Factors Affecting Medical Condition, Hypertensive Disorder NOS | | | | | | | | | | |
| 316 Psychological Factors Affecting Medical Condition, Neurodermatitis | N | N | N | N | N | N | | N | N | N |
| 301.20 Schizoid Personality Disorder | | N | | N | N | N | | N | N | N |

APPENDIX II-continued

| | | | | | | | | | |
|---|---|---|---|---|---|---|---|---|---|
| 301.22 Schizotypal Personality Disorder | | | | | | | | | |
| 301.4 Obsessive-Compulsive Personality Disorder | | N | | N | N | N | | N | N | N |
| 301.50 Histrionic Personality Disorder | C | N | C | N | N | | | | | N |
| 301.6 Dependent Personality Disorder | N | N | | N | N | | | N | N | N |
| 301.7 Antisocial Personality Disorder | | N | | N | N | | | N | N | N |
| 301.82 Avoidant Personality Disorder | | N | | N | N | | | N | N | N |
| 301.83 Borderline Personality Disorder | | N | | N | N | C | | N | N | N |
| 302.71 Hypoactive Sexual Desire Disorder | | N | | N | N | | | | | |
| 307.42 Primary Insomnia | | N | | N | N | N | | N | N | N |
| 307.44 Hypersomnia related to . . . [Indicate the Axis I or Axis II Disorder] | C | N | | N | N | | | | | |
| 307.44 Primary Hypersomnia | | N | | N | N | | | N | N | |
| 307.45 Circadian Rhythm Sleep Disorder | | N | | N | N | | | | | N |
| 307.47 Dyssomnia NOS | | N | | N | N | | C | N | N | N |
| 307.47 Parasomnia NOS | | N | | N | N | | | | | |
| 780.59 Breathing-Related Sleep Disorder | | N | | | | | | | | |
| 300.7 Body Dysmorphic Disorder | | N | C | N | N | C | | N | N | N |
| 300.7 Hypochondriasis | C | N | C | N | N | | | C | C | N |
| 300.81 Somatization Disorder | C | N | C | N | N | C | C | N | N | N |
| 300.81 Somatoform Disorder NOS | C | N | C | N | N | C | C | N | N | N |
| Pain Disorder 307.89 Pain Associated With Both Psychological Factors and a General Medical Condition | | N | C | N | N | C | | N | N | N |
| Alcohol Abuse & Dependence | | N | C | N | N | | C | N | N | N |
| Amphetamine Abuse & Dependence | | N | | N | N | | | N | N | N |
| Cannabis Abuse & Dependence | | N | | N | N | | | | | N |
| Cocaine Abuse & Dependence | | N | | N | N | | | N | N | N |
| Inhalant Abuse & Dependence | | | | | | | | | | N |
| Nicotine Dependence | | | | | | | | | | |
| Opioid Abuse & Dependence | | N | | N | N | | | | | N |
| Sedative, Hypnotic or Anxiolytic Abuse & Dependence | | N | C | N | N | C | C | | | N |

| | DI-PHENYL-HYDAN-TOIN 27 | DIVAL-PROEX 2 | GABA-PENTIN 79 | LAMOT-RIGINE 76 | GUAN-FACINE HCL 13 | CLONI-DINE 17 | ALPRA-ZOLAM 20 | CLONA-ZEPAM 23 | CLORA-ZEPATE 35 | DIAZE-PAM 57 |
|---|---|---|---|---|---|---|---|---|---|---|
| 300.00 Anxiety Disorder NOS | | N | N | N | | | C | C | C | N |
| 300.02 Generalized Anxiety Disorder | | N | N | N | N | N | C | C | C | C |
| 300.22 Agoraphobia Without History of Panic Disorder | | N | N | N | | | C | C | C | C |
| 300.23 Social Phobia | | N | N | N | | | C | C | C | C |
| 300.29 Specific Phobia | | N | N | N | | | C | C | C | C |
| 300.3 Obsessive-Compulsive Disorder | | N | N | N | | | | N | | N |
| 309.81 Posttraumatic Stress Disorder | N | N | N | N | | | C | C | | C |
| Panic Disorder | | N | N | N | | | C | C | | C |
| 299.00 Autistic Disorder | N | N | N | N | | | | | | |
| 299.80 Pervasive Developmental Disorder NOS | N | N | N | N | N | N | | | | |
| 307.20 Tic Disorder NOS | N | N | N | N | | | C | C | | N |
| 307.22 Chronic Motor or Vocal Tic Disorder | N | N | N | N | N | C | N | N | N | N |
| 307.23 Tourette's Disorder | N | N | N | N | | | C | C | | N |
| 307.9 Communication Disorder NOS | | N | | N | | | | | | N |

APPENDIX II-continued

| Disorder | 1 | 2 | 3 | 4 | 5 | 6 | 7 | 8 | 9 |
|---|---|---|---|---|---|---|---|---|---|
| 309.21 Separation Anxiety Disorder | | N | N | N | | | C | C | N |
| 312.8 Conduct Disorder | | N | N | N | N | N | | | |
| 313.81 Oppositional Defiant Disorder | N | N | N | N | N | N | | | |
| 315.9 Learning Disorder NOS | | N | | N | | | | | |
| Attention-Deficit/Hyperactivity Disorder | | N | N | N | C | C | | | |
| 294.8 Amnestic Disorder | | | | | | | C | C | C |
| 294.9 Cognitive Disorder NOS | | N | | N | | | | | |
| Dementia of the Alzheimer's Type | | | | N | | | | | |
| 307.1 Anorexia Nervosa | | N | N | N | | | C | C | C | N |
| 307.50 Eating Disorder NOS | N | N | N | N | | | C | C | N | N |
| 307.51 Bulimia Nervosa | | N | N | N | | | N | N | | N |
| 312.30 Impulse-Control Disorder NOS | N | N | N | N | N | N | C | C | | N |
| 312.31 Pathological Gambling | N | N | N | N | | | N | N | | N |
| 312.34 Intermittent Explosive Disorder | N | N | N | N | N | N | C | C | | C |
| 312.39 Trichotillomania | | N | N | N | | | C | C | | C |
| 296.89 Bipolar II Disorder | N | C | C | N | | | C | C | | N |
| 296.90 Mood Disorder NOS | N | N | N | N | | | C | C | | C |
| 300.4 Dysthymic Disorder | N | N | | N | N | N | | | N | |
| 301.13 Cyclothymic Disorder | | N | N | N | N | N | C | C | C | N |
| 311 Depressive Disorder NOS | N | N | N | N | N | N | N | N | N | N |
| Bipolar I Disorder | N | C | C | N | | | C | C | | |
| Major Depressive Disorder, Recurrent | N | N | N | N | | | C | C | | C |
| Major Depressive Disorder, Single Episode | N | N | N | N | | | C | C | | C |
| 316 Psychological Factors Affecting Medical Condition, Irritable Bowel Syndrome | | N | N | N | | | C | C | C | C |
| 316 Psychological Factors Affecting Medical Condition, Atypical Asthma | | N | N | N | | | | | | |
| 316 Psychological Factors Affecting Medical Condition, Hypertensive Disorder NOS | | | | | N | N | | | | |
| 316 Psychological Factors Affecting Medical Condition, Neurodermatitis | | N | N | N | N | N | C | C | C | C |
| 301.20 Schizoid Personality Disorder | | N | N | N | | | C | C | | |
| 301.22 Schizotypal Personality Disorder | | | | | | | | | | |
| 301.4 Obsessive-Compulsive Personality Disorder | | N | N | N | | | | N | | N |
| 301.50 Histrionic Personality Disorder | | N | N | N | | | C | C | | |
| 301.6 Dependent Personality Disorder | | N | N | N | | | N | N | N | N |
| 301.7 Antisocial Personality Disorder | N | N | N | N | | | C | C | C | |
| 301.82 Avoidant Personality Disorder | | N | N | N | | | C | C | | |
| 301.83 Borderline Personality Disorder | N | N | N | N | | | C | N | | N |
| 302.71 Hypoactive Sexual Desire Disorder | | | | | | | | | | |
| 307.42 Primary Insomnia | | N | N | N | N | N | C | C | | C |
| 307.44 Hypersomnia related to . . . [Indicate the Axis I or Axis II Disorder] | | | | | | | | | | |
| 307.44 Primary Hypersomnia | | | | | | | | | | |
| 307.45 Circadian Rhythm Sleep Disorder | N | N | N | N | N | N | C | C | C | |
| 307.47 Dyssomnia NOS | N | N | N | N | N | N | C | C | N | C |
| 307.47 Parasomnia NOS | | N | N | N | | | | | | C |
| 780.59 Breathing-Related Sleep Disorder | | | | | | | | | | |
| 300.7 Body Dysmorphic Disorder | | N | N | N | | | | N | | N |
| 300.7 Hypochondriasis | | N | N | N | | | C | C | | N |
| 300.81 Somatization Disorder | | N | N | N | | | C | C | C | C |
| 300.81 Somatoform Disorder NOS | | N | N | N | | | C | C | C | C |

APPENDIX II-continued

| | | | | | | | | | | |
|---|---|---|---|---|---|---|---|---|---|---|
| Pain Disorder 307.89 Pain Associated With Both Psychological Factors and a General Medical Condition | N | N | N | N | | | N | N | | N |
| Alcohol Abuse & Dependence | N | N | N | N | | C | C | C | C | C |
| Amphetamine Abuse & Dependence | | N | N | N | | | C | C | C | C |
| Cannabis Abuse & Dependence | N | N | N | N | N | N | N | N | N | N |
| Cocaine Abuse & Dependence | | N | N | N | | | N | C | C | N |
| Inhalant Abuse & Dependence | N | N | N | N | | | | | | N |
| Nicotine Dependence | | N | N | N | | | | | | |
| Opioid Abuse & Dependence | | N | N | N | | | | | | |
| Sedative, Hypnotic or Anxiolytic Abuse & Dependence | N | N | N | N | | | C | C | | C |

| | FLURA-ZEPAM 51 | LORA-ZEPAM 1 | OXA-ZEPAM 50 | QUA-ZEPAM 32 | TEMA-ZEPAM 37 | TRIA-ZOLAM 46 | ATEN-OLOL 75 | METO-POLO 74 | PROPRA-NOLOL 31 | LITHIUM 14 |
|---|---|---|---|---|---|---|---|---|---|---|
| 300.00 Anxiety Disorder NOS | | C | C | C | | | N | N | N | N |
| 300.02 Generalized Anxiety Disorder | | C | C | C | | | N | N | N | |
| 300.22 Agoraphobia Without History of Panic Disorder | | C | C | C | | | N | N | N | N |
| 300.23 Social Phobia | | C | C | C | | | N | N | N | |
| 300.29 Specific Phobia | | C | C | C | | | | | | |
| 300.3 Obsessive-Compulsive Disorder | | | | | | | N | N | N | N |
| 309.81 Posttraumatic Stress Disorder | | C | C | | | C | N | N | N | N |
| Panic Disorder | | C | C | C | | | N | N | N | N |
| 299.00 Autistic Disorder | | | | | | | N | N | N | |
| 299.80 Pervasive Developmental Disorder NOS | | | | | | | N | N | N | N |
| 307.20 Tic Disorder NOS | | C | | | | | N | N | N | |
| 307.22 Chronic Motor or Vocal Tic Disorder | | N | N | N | | | N | N | N | N |
| 307.23 Tourette's Disorder | | C | | | | | N | N | N | |
| 307.9 Communication Disorder NOS | | N | | | | | | | | |
| 309.21 Separation Anxiety Disorder | | | | | | | N | N | N | N |
| 312.8 Conduct Disorder | | | | | | | N | N | N | N |
| 313.81 Oppositional Defiant Disorder | | | | | | | N | N | N | N |
| 315.9 Learning Disorder NOS | | | | | | | N | N | N | |
| Attention-Deficit/Hyperactivity Disorder | | | | | | | N | N | N | |
| 294.8 Amnestic Disorder | | C | | | | | | | | |
| 294.9 Cognitive Disorder NOS Dementia of the Alzheimer's Type | | N | | | | | N | N | N | |
| 307.1 Anorexia Nervosa | | | | C | | | N | N | N | N |
| 307.50 Eating Disorder NOS | | | | | | | N | N | N | N |
| 307.51 Bulimia Nervosa | | N | | | | | N | N | N | N |
| 312.30 Impulse-Control Disorder NOS | | C | | | | | N | N | N | N |
| 312.31 Pathological Gambling | | N | | | | | N | N | N | C |
| 312.34 Intermittent Explosive Disorder | | C | C | | | | N | N | N | N |
| 312.39 Trichotillomania | | | | | | | N | N | N | |
| 296.89 Bipolar II Disorder | | N | | | | | N | N | N | C |
| 296.90 Mood Disorder NOS | | | | | | | N | N | N | N |
| 300.4 Dysthymic Disorder | | | | | | | N | | | N |
| 301.13 Cyclothymic Disorder | | | | | | | N | N | N | C |
| 311 Depressive Disorder NOS | | | | | | | N | N | N | N |
| Bipolar I Disorder | | N | | | | | N | N | N | C |
| Major Depressive Disorder, Recurrent | | | | | | | N | N | N | N |
| Major Depressive Disorder, Single Episode | | | | | | | N | N | N | N |
| 316 Psychological Factors Affecting Medical Condition, Irritable Bowel Syndrome | | C | C | | | | N | N | N | |

APPENDIX II-continued

| Disorder | 1 | 2 | 3 | 4 | 5 | 6 | 7 | 8 | 9 | 10 |
|---|---|---|---|---|---|---|---|---|---|---|
| 316 Psychological Factors Affecting Medical Condition, Atypical Asthma | | | | | | | N | N | N | |
| 316 Psychological Factors Affecting Medical Condition, Hypertensive Disorder NOS | | | | | | | N | N | N | |
| 316 Psychological Factors Affecting Medical Condition, Neurodermatitis | | C | C | C | | | N | N | N | |
| 301.20 Schizoid Personality Disorder | | C | C | | | | N | N | N | N |
| 301.22 Schizotypal Personality Disorder | | | | | | | N | N | N | N |
| 301.4 Obsessive-Compulsive Personality Disorder | | | | | | | N | N | N | N |
| 301.50 Histrionic Personality Disorder | | | | | | | N | N | N | N |
| 301.6 Dependent Personality Disorder | | | | | | | N | N | N | |
| 301.7 Antisocial Personality Disorder | | | | | | | N | N | N | N |
| 301.82 Avoidant Personality Disorder | | | | | | | N | N | N | |
| 301.83 Borderline Personality Disorder | | | | | | | N | N | N | N |
| 302.71 Hypoactive Sexual Desire Disorder | | | | | | | | | | |
| 307.42 Primary Insomnia | C | C | C | C | C | C | N | N | N | N |
| 307.44 Hypersomnia related to . . . [Indicate the Axis I or Axis II Disorder] | | | | | | | | | | |
| 307.44 Primary Hypersomnia | | | | | | | | | | |
| 307.45 Circadian Rhythm Sleep Disorder | C | C | C | C | C | C | N | N | N | N |
| 307.47 Dyssomnia NOS | C | C | C | C | C | C | N | N | N | N |
| 307.47 Parasomnia NOS | C | | C | | | C | | | | |
| 780.59 Breathing-Related Sleep Disorder | | | | | | | | | | |
| 300.7 Body Dysmorphic Disorder | | N | | | | | N | N | N | |
| 300.7 Hypochondriasis | | | | | | | N | N | N | |
| 300.81 Somatization Disorder | | C | C | C | | | N | N | N | |
| 300.81 Somatoform Disorder NOS | | C | C | C | | | N | N | N | |
| Pain Disorder 307.89 Pain Associated With Both Psychological Factors and a General Medical Condition | | N | N | N | | | N | N | N | |
| Alcohol Abuse & Dependence | | C | C | C | C | | N | N | N | C |
| Amphetamine Abuse & Dependence | | C | | C | C | | N | N | N | |
| Cannabis Abuse & Dependence | | N | N | N | | | N | N | N | N |
| Cocaine Abuse & Dependence | | N | | | | | | | | |
| Inhalant Abuse & Dependence | | | | | | | N | N | N | N |
| Nicotine Dependence | | | | | | | N | N | N | |
| Opioid Abuse & Dependence | | | | | | | N | N | N | |
| Sedative, Hypnotic or Anxiolytic Abuse & Dependence | | C | | | | | N | N | N | N |

| | GINKGO BILOBA 84 | KAVA KAVA 97 | ST JOHNSWORT 73 | FLUPHEN-AZINE 43 | HALPE-RIDOL 34 | LOXAPINE 3 | OLANZA-PINE 78 |
|---|---|---|---|---|---|---|---|
| 300.00 Anxiety Disorder NOS | N | N | N | | | | |
| 300.02 Generalized Anxiety Disorder | N | N | N | | | | |
| 300.22 Agoraphobia Without History of Panic Disorder | N | N | N | | | | |
| 300.23 Social Phobia | N | N | N | | | | |
| 300.29 Specific Phobia. | N | N | N | | | | |
| 300.3 Obsessive-Compulsive Disorder | N | | N | | | | |
| 309.81 Posttraumatic Stress Disorder | N | N | N | | | | |
| Panic Disorder | | N | | | | | |

APPENDIX II-continued

| Disorder | 1 | 2 | 3 | 4 | 5 | 6 | 7 |
|---|---|---|---|---|---|---|---|
| 299.00 Autistic Disorder | N | | | | | | |
| 299.80 Pervasive Developmental Disorder NOS | N | | | | | | |
| 307.20 Tic Disorder NOS | | N | | | | | |
| 307.22 Chronic Motor or Vocal Tic Disorder | | N | | | | | |
| 307.23 Tourette's Disorder | | N | | | | | |
| 307.9 Communication Disorder NOS | N | | | | | | |
| 309.21 Separation Anxiety Disorder | N | N | N | | | | |
| 312.8 Conduct Disorder | N | | | | | | |
| 313.81 Oppositional Defiant Disorder | N | N | N | | | | |
| 315.9 Learning Disorder NOS | N | | | | | | |
| Attention-Deficit/Hyperactivity Disorder | N | | | | | | |
| 294.8 Amnestic Disorder | N | | | | | | |
| 294.9 Cognitive Disorder NOS | N | | | | | | |
| Dementia of the Alzheimer's Type | N | | | | | | |
| 307.1 Anorexia Nervosa | N | N | N | | | | |
| 307.50 Eating Disorder NOS | N | | N | | | | C |
| 307.51 Bulimia Nervosa | N | N | N | | | | C |
| 312.30 Impulse-Control Disorder NOS | | | | | | | |
| 312.31 Pathological Gambling | | | | | | | |
| 312.34 Intermittent Explosive Disorder | N | | | C | C | C | C |
| 312.39 Trichotillomania | | N | | | | | |
| 296.89 Bipolar II Disorder | N | N | | C | C | | C |
| 296.90 Mood Disorder NOS | | | N | | | | |
| 300.4 Dysthymic Disorder | | | N | | | | |
| 301.13 Cyclothymic Disorder | | | | | | | |
| 311 Depressive Disorder NOS | N | | N | | | | |
| Bipolar I Disorder | N | N | | C | C | | C |
| Major Depressive Disorder, Recurrent | | | N | | | | |
| Major Depressive Disorder, Single Episode | | | N | | | | |
| 316 Psychological Factors Affecting Medical Condition, Irritable Bowel Syndrome | | N | N | | | | |
| 316 Psychological Factors Affecting Medical Condition, Atypical Asthma | N | N | | | | | |
| 316 Psychological Factors Affecting Medical Condition, Hypertensive Disorder NOS | | | | | | | |
| 316 Psychological Factors Affecting Medical Condition, Neurodermatitis | N | N | N | | | | |
| 301.20 Schizoid Personality Disorder | N | N | N | | C | C | C |
| 301.22 Schizotypal Personality Disorder | | | N | | C | C | C |
| 301.4 Obsessive-Compulsive Personality Disorder | N | | N | | | | |
| 301.50 Histrionic Personality Disorder | | | | | | | |
| 301.6 Dependent Personality Disorder | N | | | | | | |
| 301.7 Antisocial Personality Disorder | N | | | | | | |
| 301.82 Avoidant Personality Disorder | N | N | N | | | | |
| 301.83 Borderline Personality Disorder | N | | N | C | C | | C |
| 302.71 Hypoactive Sexual Desire Disorder | | | | | | | |
| 307.42 Primary Insomnia | | N | N | | | | |
| 307.44 Hypersomnia related to . . . [Indicate the Axis I or Axis II Disorder] | | | | | | | |
| 307.44 Primary Hypersomnia | N | | | | | | |
| 307.45 Circadian Rhythm Sleep Disorder | | N | | | | | |
| 307.47 Dyssomnia NOS | | N | N | | | | |
| 307.47 Parasomnia NOS | | | | | | | |

APPENDIX II-continued

| | | | | | | | | | |
|---|---|---|---|---|---|---|---|---|---|
| 780.59 Breathing-Related Sleep Disorder | N | | | | | | | | |
| 300.7 Body Dysmorphic Disorder | N | | N | | C | | C | | |
| 300.7 Hypochondriasis | | | N | | | | | | |
| 300.81 Somatization Disorder | N | N | N | | | | | | |
| 300.81 Somatoform Disorder NOS | N | N | N | | | | | | |
| Pain Disorder 307.89 Pain Associated With Both Psychological Factors and a General Medical Condition | N | N | | | | | | | |
| Alcohol Abuse & Dependence | N | N | | | | | | | |
| Amphetamine Abuse & Dependence | N | N | | | | | | | |
| Cannabis Abuse & Dependence | | | N | | | | | | |
| Cocaine Abuse & Dependence | N | | | | | | | | |
| Inhalant Abuse & Dependence | | | | | | | | | |
| Nicotine Dependence | | | | | | | | | |
| Opioid Abuse & Dependence | | | | | | | | | |
| Sedative, Hypnotic or Anxiolytic Abuse & Dependence | N | N | N | | | | | | |

| | PIMOZIDE 19 | RISPER-DONE 33 | SEROQUEL 92 | THIORI-DAZINE 16 | THIO-THIXINE 44 | TRIFLUO-PERAZINE 28 | HYDROX-YZINE 52 | SILB-TRMIN 80 | AMAN-TADINE 5 |
|---|---|---|---|---|---|---|---|---|---|
| 300.00 Anxiety Disorder NOS | | C | | | | | | | N |
| 300.02 Generalized Anxiety Disorder | | | | | | | | | |
| 300.22 Agoraphobia Without History of Panic Disorder | | N | | | | | | | |
| 300.23 Social Phobia | | | | | | | | | |
| 300.29 Specific Phobia | | | | | | | | | |
| 300.3 Obsessive-Compulsive Disorder | | | | | | | | | |
| 309.81 Posttraumatic Stress Disorder | | | | | | | | | N |
| Panic Disorder | | | | | | | | | N |
| 299.00 Autistic Disorder | | | | | | | | | |
| 299.80 Pervasive Developmental Disorder NOS | | | | | | | | | |
| 307.20 Tic Disorder NOS | | | | | | | | | N |
| 307.22 Chronic Motor or Vocal Tic Disorder | C | | | | | | | N | |
| 307.23 Tourette's Disorder | | | | | | | | | |
| 307.9 Communication Disorder NOS | | | | | | | | | |
| 309.21 Separation Anxiety Disorder | | | | | | | | | N |
| 312.8 Conduct Disorder | | | | | | | | | N |
| 313.81 Oppositional Defiant Disorder | | | | | | | | | N |
| 315.9 Learning Disorder NOS | | | | | | | | | N |
| Attention-Deficit/Hyperactivity Disorder | | | | | | | | | N |
| 294.8 Amnestic Disorder | | | | | | | | | |
| 294.9 Cognitive Disorder NOS | | | | | | | | | |
| Dementia of the Alzheimer's Type | | | | | | | | | |
| 307.1 Anorexia Nervosa | | C | | | | | | | |
| 307.50 Eating Disorder NOS | | | | | | | | | |
| 307.51 Bulimia Nervosa | | C | C | | | | | | |
| 312.30 Impulse-Control Disorder NOS | | | | | | | | | N |
| 312.31 Pathological Gambling | | | | | | | | | |
| 312.34 Intermittent Explosive Disorder | | C | C | C | C | C | | N | N |
| 312.39 Trichotillomania | | | | | | | | | |
| 296.89 Bipolar II Disorder | | C | | | | | | | |
| 296.90 Mood Disorder NOS | | | | | | | | | |
| 300.4 Dysthymic Disorder | | | | | | | | | |
| 301.13 Cyclothymic Disorder | | | | | | | | | |
| 311 Depressive Disorder NOS | | | | | | | | | |

APPENDIX II-continued

| Disorder | C1 | C2 | C3 | C4 | C5 | C6 | C7 | C8 |
|---|---|---|---|---|---|---|---|---|
| Bipolar I Disorder | C | | | | | | | |
| Major Depressive Disorder, Recurrent | | | | | | | | |
| Major Depressive Disorder, Single Episode | | | | | | | | |
| 316 Psychological Factors Affecting Medical Condition, Irritable Bowel Syndrome | | | | | | | | |
| 316 Psychological Factors Affecting Medical Condition, Atypical Asthma | | | | | | | | |
| 316 Psychological Factors Affecting Medical Condition, Hypertensive Disorder NOS | | | | | | | | |
| 316 Psychological Factors Affecting Medical Condition, Neurodermatitis | | | | | | | | N |
| 301.20 Schizoid Personality Disorder | C | | C | | | | | |
| 301.22 Schizotypal Personality Disorder | C | | C | | | | | |
| 301.4 Obsessive-Compulsive Personality Disorder | | | | | | | | |
| 301.50 Histrionic Personality Disorder | | | | | | | | |
| 301.6 Dependent Personality Disorder | | | | | | | | |
| 301.7 Antisocial Personality Disorder | C | | | | | | | |
| 301.82 Avoidant Personality Disorder | | | | | | | | |
| 301.83 Borderline Personality Disorder | C | C | | C | | | | |
| 302.71 Hypoactive Sexual Desire Disorder | | | | | | | | |
| 307.42 Primary Insomnia | | | | | | C | | |
| 307.44 Hypersomnia related to . . . [Indicate the Axis I or Axis II Disorder] | | | | | | | | |
| 307.44 Primary Hypersomnia | | | | | | | | |
| 307.45 Circadian Rhythm Sleep Disorder | | | | | | C | N | |
| 307.47 Dyssomnia NOS | | | | | | C | | |
| 307.47 Parasomnia NOS | | | | | | C | | |
| 780.59 Breathing-Related Sleep Disorder | | | | | | | | |
| 300.7 Body Dysmorphic Disorder | | | | | | | | |
| 300.7 Hypochondriasis | | | | | | | | |
| 300.81 Somatization Disorder | | | | | | | | |
| 300.81 Somatoform Disorder NOS | | | | | | | | |
| Pain Disorder 307.89 Pain Associated With Both Psychological Factors and a General Medical Condition | | | | | | | | N |
| Alcohol Abuse & Dependence | | | | | | | | |
| Amphetamine Abuse & Dependence | C | | | | | | | N |
| Cannabis Abuse & Dependence | | | | | | | N | |
| Cocaine Abuse & Dependence | | | | | | | | C |
| Inhalant Abuse & Dependence | | | | | | | | N |
| Nicotine Dependence | | | | | | | | |
| Opioid Abuse & Dependence | | | | | | | | |
| Sedative, Hypnotic or Anxiolytic Abuse & Dependence | | | | | | | | N |

| | PHOTO-THERAPY 10,000 LUX 86 | ZOLPIDEM 45 | ADDERALL 70 | DEXEDRINE 21 | METHAMPHETAMINE 71 | METHYLPHENIDATE 10 | MODAFINIL 95 | PEMOLINE 22 | PHENTERMINE 29 |
|---|---|---|---|---|---|---|---|---|---|
| 300.00 Anxiety Disorder NOS | N | | N | N | N | N | | N | |
| 300.02 Generalized Anxiety Disorder | | | | | | N | | N | |

APPENDIX II-continued

| Disorder | C1 | C2 | C3 | C4 | C5 | C6 | C7 | C8 |
|---|---|---|---|---|---|---|---|---|
| 300.22 Agoraphobia Without History of Panic Disorder | N | N | N | N | N | N | N | |
| 300.23 Social Phobia | N | N | N | N | N | | N | |
| 300.29 Specific Phobia | | N | N | N | N | | N | |
| 300.3 Obsessive-Compulsive Disorder | N | N | N | N | N | | N | |
| 309.81 Posttraumatic Stress Disorder | N | N | N | N | N | | N | |
| Panic Disorder | | N | N | N | N | | N | |
| 299.00 Autistic Disorder | | N | N | N | N | | N | |
| 299.80 Pervasive Developmental Disorder NOS | | N | N | N | N | | N | N |
| 307.20 Tic Disorder NOS | | | | | | | | |
| 307.22 Chronic Motor or Vocal Tic Disorder | | N | N | N | N | | N | N |
| 307.23 Tourette's Disorder | | | | | | | | |
| 307.9 Communication Disorder NOS | | | | | | | N | N |
| 309.21 Separation Anxiety Disorder | | N | N | N | N | | N | N |
| 312.8 Conduct Disorder | | N | N | N | N | | N | N |
| 313.81 Oppositional Defiant Disorder | N | N | N | N | N | | N | |
| 315.9 Learning Disorder NOS | | N | N | N | N | | N | |
| Attention-Deficit/Hyperactivity Disorder | | C | C | C | C | | C | |
| 294.8 Amnestic Disorder | N | | | | | N | N | |
| 294.9 Cognitive Disorder NOS | | N | N | N | N | | N | N |
| Dementia of the Alzheimer's Type | | | | | | | | |
| 307.1 Anorexia Nervosa | N | N | N | N | N | | N | |
| 307.50 Eating Disorder NOS | N | N | N | | N | | N | N |
| 307.51 Bulimia Nervosa | N | N | N | N | N | | N | |
| 312.30 Impulse-Control Disorder NOS | | N | N | N | N | | N | |
| 312.31 Pathological Gambling | | N | N | N | N | | N | |
| 312.34 Intermittent Explosive Disorder | | N | N | N | N | | N | |
| 312.39 Trichotillomania | N | N | N | N | N | | | |
| 296.89 Bipolar II Disorder | N | N | N | N | N | | N | |
| 296.90 Mood Disorder NOS | N | N | N | N | N | | N | |
| 300.4 Dysthymic Disorder | N | N | N | N | N | | N | N |
| 301.13 Cyclothymic Disorder | | N | N | N | N | | N | |
| 311 Depressive Disorder NOS | N | N | N | N | N | | N | N |
| Bipolar I Disorder | N | N | N | N | N | | N | |
| Major Depressive Disorder, Recurrent | N | N | N | N | N | | N | |
| Major Depressive Disorder, Single Episode | N | N | N | N | N | | N | |
| 316 Psychological Factors Affecting Medical Condition, Irritable Bowel Syndrome | | | | | | | N | |
| 316 Psychological Factors Affecting Medical Condition, Atypical Asthma | N | N | N | N | N | | N | N |
| 316 Psychological Factors Affecting Medical Condition, Hypertensive Disorder NOS | | N | N | | | | | |
| 316 Psychological Factors Affecting Medical Condition, Neurodermatitis | N | N | N | N | N | | | |
| 301.20 Schizoid Personality Disorder | N | N | N | N | N | | N | |
| 301.22 Schizotypal Personality Disorder | | | | | | | N | |
| 301.4 Obsessive-Compulsive Personality Disorder | N | N | N | N | N | | N | |
| 301.50 Histrionic Personality Disorder | | N | N | | N | | N | |
| 301.6 Dependent Personality Disorder | | N | N | | | | N | N |
| 301.7 Antisocial Personality Disorder | N | N | N | N | N | | N | |
| 301.82 Avoidant Personality Disorder | N | N | N | N | N | | N | |
| 301.83 Borderline Personality Disorder | N | N | N | N | N | | N | |
| 302.71 Hypoactive Sexual Desire Disorder | | | | | | | | |

APPENDIX II-continued

| | | | | | | | | |
|---|---|---|---|---|---|---|---|---|
| 307.42 Primary Insomnia | N | C | N | N | N | N | | N | |
| 307.44 Hypersomnia related to . . . [Indicate the Axis I or Axis II Disorder] | | | N | N | N | N | C | N | |
| 307.44 Primary Hypersomnia | N | | N | N | N | N | | N | N |
| 307.45 Circadian Rhythm Sleep Disorder | N | C | N | N | N | N | | N | N |
| 307.47 Dyssomnia NOS | N | C | | N | N | N | | N | |
| 307.47 Parasomnia NOS | N | C | N | N | N | N | | N | |
| 780.59 Breathing-Related Sleep Disorder | | | N | N | N | N | | N | N |
| 300.7 Body Dysmorphic Disorder | N | | N | N | N | N | | N | |
| 300.7 Hypochondriasis | | | N | N | N | N | | N | |
| 300.81 Somatization Disorder | N | | N | N | N | N | | N | |
| 300.81 Somatoform Disorder NOS | N | | N | N | N | N | | N | |
| Pain Disorder 307.89 Pain Associated With Both Psychological Factors and a General Medical Condition | N | | N | N | N | N | | N | |
| Alcohol Abuse & Dependence | N | C | N | N | N | N | | N | |
| Amphetamine Abuse & Dependence | N | C | N | N | N | N | | N | |
| Cannabis Abuse & Dependence | | | N | N | N | N | | N | N |
| Cocaine Abuse & Dependence | N | | N | N | N | N | | N | N |
| Inhalant Abuse & Dependence | | | | | | | | N | |
| Nicotine Dependence | | | N | N | N | N | | N | |
| Opioid Abuse & Dependence | N | | N | N | N | N | | N | |
| Sedative, Hypnotic or Anxiolytic Abuse & Dependence | N | | N | N | N | N | | N | C |

| | SR METHYLPHENIDATE 88 |
|---|---|
| 300.00 Anxiety Disorder NOS | N |
| 300.02 Generalized Anxiety Disorder | N |
| 300.22 Agoraphobia Without History of Panic Disorder | N |
| 300.23 Social Phobia | N |
| 300.29 Specific Phobia | N |
| 300.3 Obsessive-Compulsive Disorder | N |
| 309.81 Posttraumatic Stress Disorder | N |
| Panic Disorder | N |
| 299.00 Autistic Disorder | |
| 299.80 Pervasive Developmental Disorder NOS | N |
| 307.20 Tic Disorder NOS | |
| 307.22 Chronic Motor or Vocal Tic Disorder | N |
| 307.23 Tourette's Disorder | |
| 307.9 Communication Disorder NOS | N |
| 309.21 Separation Anxiety Disorder | N |
| 312.8 Conduct Disorder | N |
| 313.81 Oppositional Defiant Disorder | N |
| 315.9 Learning Disorder NOS | N |
| Attention-Deficit/Hyperactivity Disorder | |
| 294.8 Amnestic Disorder | N |
| 294.9 Cognitive Disorder NOS | N |
| Dementia of the Alzheimer's Type | N |
| 307.1 Anorexia Nervosa | N |
| 307.50 Eating Disorder NOS | N |
| 307.51 Bulimia Nervosa | N |
| 312.30 Impulse-Control Disorder NOS | N |
| 312.31 Pathological Gambling | N |
| 312.34 Intermittent Explosive Disorder | N |
| 312.39 Trichotillomania | N |
| 296.89 Bipolar II Disorder | N |
| 296.90 Mood Disorder NOS | N |
| 300.4 Dysthymic Disorder | N |
| 301.13 Cyclothymic Disorder | N |
| 311 Depressive Disorder NOS | N |
| Bipolar I Disorder | N |
| Major Depressive Disorder, Recurrent | N |
| Major Depressive Disorder, Single Episode | N |
| 316 Psychological Factors Affecting Medical Condition, Irritable Bowel Syndrome | |

APPENDIX II-continued

| | |
|---|---|
| 316 Psychological Factors Affecting Medical Condition, Atypical Asthma | N |
| 316 Psychological Factors Affecting Medical Condition, Hypertensive Disorder NOS | |
| 316 Psychological Factors Affecting Medical Condition, Neurodermatitis | N |
| 301.20 Schizoid Personality Disorder | N |
| 301.22 Schizotypal Personality Disorder | |
| 301.4 Obsessive-Compulsive Personality Disorder | N |
| 301.50 Histrionic Personality Disorder | N |
| 301.6 Dependent Personality Disorder | N |
| 301.7 Antisocial Personality Disorder | N |
| 301.82 Avoidant Personality Disorder | |
| 301.83 Borderline Personality Disorder | N |
| 302.71 Hypoactive Sexual Desire Disorder | |
| 307.42 Primary Insomnia | N |
| 307.44 Hypersomnia related to . . . [Indicate the Axis I or Axis II Disorder] | |
| 307.44 Primary Hypersomnia | N |
| 307.45 Circadian Rhythm Sleep Disorder | N |
| 307.47 Dyssomnia NOS | N |
| 307.47 Parasomnia NOS | N |
| 780.59 Breathing-Related Sleep Disorder | N |
| 300.7 Body Dysmorphic Disorder | N |
| 300.7 Hypochondriasis | N |
| 300.81 Somatization Disorder | N |
| 300.81 Somatoform Disorder NOS | N |
| Pain Disorder 307.89 Pain Associated With Both Psychological Factors and a General Medical Condition | N |
| Alcohol Abuse & Dependence | N |
| Amphetamine Abuse & Dependence | N |
| Cannabis Abuse & Dependence | N |
| Cocaine Abuse & Dependence | N |
| Inhalant Abuse & Dependence | N |
| Nicotine Dependence | N |
| Opioid Abuse & Dependence | |
| Sedative, Hypnotic or Anxiolytic Abuse & Dependence | N |

We claim:

1. A method of screening a therapeutic agent for therapeutic effectiveness, comprising:
   a. providing:
      i) at least one patient, wherein said patient has a first disorder associated with a first set of electroencephalographic information;
      ii) a plurality of reference patients comprising at least one second disorder associated with a second set of electroencephalographic information;
      iii) a therapeutic agent, wherein said agent has no known therapeutic effectiveness for said at least one second disorder; and
   b. treating said patient with said agent, wherein said agent is therapeutically effective for said first disorder;
   c. identifying, using a computer a similarity between said first set of electroencephalographic information and said second set of electroencephalographic information; and
   d. indicating said agent as having therapeutic effectiveness for said at least one second disorder based upon said similarity in said reference patients.

2. The method of claim 1, further comprising, before step (b) obtaining said first set of electroencephalographic information from said patient.

3. The method of claim 1, further comprising, before step (b) obtaining said second set of electroencephalographic information from said reference patients.

4. The method of claim 1, wherein said first and second sets of electroencephalographic information comprise at least one multivariate measurement.

5. The method of claim 4, wherein said at least one multivariate measurement further comprises at least one univariate measurement.

6. The method of claim 1, wherein said similarity comprises a responsivity profile.

7. The method of claim 1, wherein said similarity comprises a cluster.

8. The method of claim 1, wherein said second disorder is the same as said first disorder.

9. The method of claim 1, wherein said second disorder is different than said first disorder.

10. The method of claim 1, wherein said identifying comprises cluster analysis.

11. The method of claim 1, wherein said first disorder comprises a behaviorally diagnosed disorder defined by the Diagnostic and Statistical Manual of Mental Disorders classification.

12. The method of claim 7, wherein said second disorder comprises a behaviorally diagnosed disorder defined by the Diagnostic and Statistical Manual of Mental Disorders classification.

13. The method of claim 1, where said agent is selected from the group consisting of alprazolam, amantadine, amitriptyline, atenolol, bethanechol, bupropion, buspirone, carbamazepine, chlorpromazine, chlordiazepoxide, citalopram, clomipramine, clonidine, clonazepam, clozapine, cyproheptadine, dextroamphetamine, dexamethasone, divalproex, deprenyl, desipramine, dexamethasone, dextroamphetamine, diazepam, disulfram, divalproex, doxepin, ethchlorvynol, fluoxetine, fluvoxamine, felbamate, fluphenazine, gabapentin, haloperidol, imipramine, isocarboxazid, lamotrigine, levothyroxine, liothyronine, lithium carbonate, lithium citrate, lorazepam, loxapine, maprotiline, meprobamate, mesoridazine, methamphetamine, methylphenidate, midazolam, meprobamate, mirtazapine, molindone, moclobemide, molindone, naltrexone, phenelzine, nefazodone, nortriptyline, olanzapine, oxazepam, paroxetine, pemoline, perphenazine, phenelzine, pimozide, pindolol, prazepam, propranolol, protriptyline, quetiapine, reboxetine, risperidone, selegiline, sertraline, sertindole, trifluoperazine, trimipramine, temazepam, thioridazine, topiramate, tranylcypromine, trazodone, triazolam, trihexyphenidyl, trimipramine, valproic acid, venlafaxine, and any combination thereof.

* * * * *